(12) United States Patent
Zarins et al.

(10) Patent No.: US 11,793,564 B2
(45) Date of Patent: *Oct. 24, 2023

(54) METHODS AND SYSTEMS FOR THE TREATMENT OF POLYCYSTIC OVARY SYNDROME

(71) Applicant: May Health US Inc., Menlo Park, CA (US)

(72) Inventors: Denise Zarins, Saratoga, CA (US); Neil Barman, Menlo Park, CA (US); Garrett Schwab, Oakland, CA (US); Roger Osborne, La Honda, CA (US); Douglas Sutton, Pacifica, CA (US)

(73) Assignee: May Health US Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/161,725

(22) Filed: Jan. 30, 2023

(65) Prior Publication Data

US 2023/0233249 A1    Jul. 27, 2023

Related U.S. Application Data

(60) Continuation of application No. 17/192,870, filed on Mar. 4, 2021, which is a continuation of application
(Continued)

(51) Int. Cl.
*A61B 18/12* (2006.01)
*A61B 18/14* (2006.01)
(Continued)

(52) U.S. Cl.
CPC .......... *A61B 18/1485* (2013.01); *A61B 8/085* (2013.01); *A61B 8/0841* (2013.01);
(Continued)

(58) Field of Classification Search
CPC ............ A61B 18/1485; A61B 18/1206; A61B 2018/00577; A61B 2018/00273;
(Continued)

(56) References Cited

U.S. PATENT DOCUMENTS 4,838,506 A    6/1989 Cooper
4,877,033 A    10/1989 Seitz, Jr.
(Continued)

FOREIGN PATENT DOCUMENTS

CN    103385754 A    11/2013
CN    103458968 A    12/2013
(Continued)

OTHER PUBLICATIONS

Amer, et al., Ovulation Induction Using Laparoscopic Ovarian Drilling in Women with Polycycstic Ovarian Syndrome: Predictors of Success, Human Reproduction, 19(8):1719-1724 (2004).
(Continued)

*Primary Examiner* — Daniel W Fowler
(74) *Attorney, Agent, or Firm* — Eversheds Sutherland (US) LLP; Christopher C. Bolten; Albert K. Heng

(57) ABSTRACT

Described here are methods and systems for the manipulation of ovarian tissues. The methods and systems may be used in the treatment of polycystic ovary syndrome (PCOS). The systems and methods may be useful in the treatment of infertility associated with PCOS.

21 Claims, 32 Drawing Sheets

Related U.S. Application Data

No. 16/819,022, filed on Mar. 13, 2020, now Pat. No. 10,939,955, which is a division of application No. 15/494,188, filed on Apr. 21, 2017, now Pat. No. 10,595,936, which is a continuation of application No. 15/094,852, filed on Apr. 8, 2016, now abandoned, which is a continuation of application No. PCT/US2014/061159, filed on Oct. 17, 2014.

(60) Provisional application No. 61/969,042, filed on Mar. 21, 2014, provisional application No. 61/892,943, filed on Oct. 18, 2013.

(51) Int. Cl.

| | | |
|---|---|---|
| *A61B 8/08* | (2006.01) | |
| *A61F 6/20* | (2006.01) | |
| *A61B 8/12* | (2006.01) | |
| A61B 17/00 | (2006.01) | |
| A61B 17/34 | (2006.01) | |
| A61B 17/42 | (2006.01) | |
| A61B 18/22 | (2006.01) | |
| A61B 8/00 | (2006.01) | |
| A61B 17/22 | (2006.01) | |
| A61B 18/00 | (2006.01) | |
| A61B 18/06 | (2006.01) | |
| A61B 18/04 | (2006.01) | |
| A61N 7/02 | (2006.01) | |
| A61B 18/02 | (2006.01) | |
| A61B 90/00 | (2016.01) | |
| A61N 7/00 | (2006.01) | |
| A61B 18/16 | (2006.01) | |

(52) U.S. Cl.
CPC ............ *A61B 8/12* (2013.01); *A61B 18/1482* (2013.01); *A61F 6/20* (2013.01); *A61B 8/4427* (2013.01); *A61B 8/4433* (2013.01); *A61B 17/22004* (2013.01); *A61B 17/42* (2013.01); *A61B 18/06* (2013.01); *A61B 18/1206* (2013.01); *A61B 18/16* (2013.01); *A61B 18/22* (2013.01); *A61B 2017/003* (2013.01); *A61B 2017/00278* (2013.01); *A61B 2017/00455* (2013.01); *A61B 2017/3405* (2013.01); *A61B 2017/3413* (2013.01); *A61B 2017/4233* (2013.01); *A61B 2018/0072* (2013.01); *A61B 2018/00196* (2013.01); *A61B 2018/00273* (2013.01); *A61B 2018/00285* (2013.01); *A61B 2018/00291* (2013.01); *A61B 2018/00559* (2013.01); *A61B 2018/00577* (2013.01); *A61B 2018/00589* (2013.01); *A61B 2018/00595* (2013.01); *A61B 2018/00642* (2013.01); *A61B 2018/00702* (2013.01); *A61B 2018/00726* (2013.01); *A61B 2018/00732* (2013.01); *A61B 2018/00744* (2013.01); *A61B 2018/00767* (2013.01); *A61B 2018/00791* (2013.01); *A61B 2018/00875* (2013.01); *A61B 2018/00982* (2013.01); *A61B 2018/0293* (2013.01); *A61B 2018/048* (2013.01); *A61B 2018/143* (2013.01); *A61B 2018/1432* (2013.01); *A61B 2018/1475* (2013.01); *A61B 2090/378* (2016.02); *A61B 2090/3925* (2016.02); *A61B 2090/3966* (2016.02); *A61N 7/02* (2013.01); *A61N 7/022* (2013.01); *A61N 2007/0043* (2013.01)

(58) Field of Classification Search
CPC ........... A61B 2018/00982; A61B 2018/00291; A61B 2018/00559
See application file for complete search history.

(56) References Cited

U.S. PATENT DOCUMENTS

| | | |
|---|---|---|
| 5,366,490 A | 11/1994 | Edwards et al. |
| 5,395,363 A | 3/1995 | Billings et al. |
| 5,540,681 A | 7/1996 | Strul et al. |
| 5,558,673 A | 9/1996 | Edwards et al. |
| 5,810,804 A | 9/1998 | Gough et al. |
| 5,853,368 A | 12/1998 | Solomon et al. |
| 5,868,740 A | 2/1999 | LeVeen et al. |
| 5,931,787 A | 8/1999 | Dietz et al. |
| 5,979,453 A | 11/1999 | Savage et al. |
| 6,063,078 A | 5/2000 | Wittkampf |
| 6,095,981 A | 8/2000 | McGahan |
| 6,165,173 A | 12/2000 | Kamdar et al. |
| 6,200,313 B1 | 3/2001 | Abe et al. |
| 6,254,601 B1 | 7/2001 | Burbank et al. |
| 6,368,280 B1 | 4/2002 | Cermak et al. |
| 6,425,867 B1 | 7/2002 | Vaezy et al. |
| 6,575,969 B1 | 6/2003 | Rittman, III et al. |
| 6,602,251 B2 | 8/2003 | Burbank et al. |
| 6,716,184 B2 | 4/2004 | Vaezy et al. |
| 6,764,488 B1 | 7/2004 | Burbank et al. |
| 6,884,219 B1 | 4/2005 | Pruter |
| 6,936,048 B2 | 8/2005 | Hurst |
| 7,676,269 B2 | 3/2010 | Yun et al. |
| 7,691,086 B2 | 4/2010 | Tkebuchava |
| 7,771,357 B2 | 8/2010 | Burbank et al. |
| 7,815,571 B2 | 10/2010 | Deckman et al. |
| 7,874,986 B2 | 1/2011 | Deckman et al. |
| 7,918,795 B2 | 4/2011 | Grossman |
| 7,981,041 B2 | 7/2011 | McGahan |
| 8,025,656 B2 | 9/2011 | Gruber et al. |
| 8,080,009 B2 | 12/2011 | Lee et al. |
| 8,088,072 B2 | 1/2012 | Munrow et al. |
| 8,121,690 B2 | 2/2012 | Yun et al. |
| 8,206,300 B2 | 6/2012 | Deckman et al. |
| 8,262,574 B2 | 9/2012 | Placek et al. |
| 8,262,577 B2 | 9/2012 | Munrow et al. |
| 8,298,145 B2 | 10/2012 | Deckman et al. |
| 8,444,636 B2 | 5/2013 | Shadduck et al. |
| 8,506,485 B2 | 8/2013 | Deckman et al. |
| 8,512,330 B2 | 8/2013 | Epstein et al. |
| 8,512,333 B2 | 8/2013 | Epstein et al. |
| 8,528,563 B2 | 9/2013 | Gruber |
| 8,992,427 B2 | 3/2015 | Munrow et al. |
| 9,357,977 B2 | 6/2016 | Grossman |
| 9,510,898 B2 | 12/2016 | Epstein et al. |
| 9,517,047 B2 | 12/2016 | Grossman |
| 9,662,166 B2 | 5/2017 | Lee et al. |
| 9,750,568 B2 | 9/2017 | Sobotka |
| 9,861,336 B2 | 1/2018 | Munrow et al. |
| 9,861,426 B2 | 1/2018 | Epstein et al. |
| 10,595,936 B2 | 3/2020 | Zarins et al. |
| 2001/0020166 A1* | 9/2001 | Daly ................. A61B 18/1477 606/41 |
| 2002/0013571 A1 | 1/2002 | Goldfarb et al. |
| 2002/0120238 A1 | 8/2002 | McGuckin, Jr. et al. |
| 2003/0028111 A1 | 2/2003 | Vaezy et al. |
| 2003/0069572 A1 | 4/2003 | Wellman et al. |
| 2003/0130575 A1 | 7/2003 | Desai |
| 2003/0130598 A1 | 7/2003 | Manning et al. |
| 2004/0143252 A1 | 7/2004 | Hurst |
| 2004/0162554 A1 | 8/2004 | Lee et al. |
| 2005/0010206 A1* | 1/2005 | Nasab ................ A61B 18/1492 606/41 |
| 2005/0059964 A1 | 3/2005 | Fitz |
| 2005/0090741 A1 | 4/2005 | Kisen et al. |
| 2005/0203399 A1 | 9/2005 | Vaezy et al. |
| 2006/0178665 A1 | 8/2006 | Sloan et al. |
| 2006/0189972 A1 | 8/2006 | Grossman |
| 2007/0161905 A1 | 7/2007 | Munrow |

(56) References Cited

U.S. PATENT DOCUMENTS

| | | |
|---|---|---|
| 2007/0179380 A1 | 8/2007 | Grossman |
| 2007/0249936 A1 | 10/2007 | Deckman et al. |
| 2008/0009747 A1 | 1/2008 | Saadat et al. |
| 2008/0167649 A1 | 7/2008 | Edwards et al. |
| 2008/0245371 A1 | 10/2008 | Gruber |
| 2009/0118727 A1 | 5/2009 | Pearson et al. |
| 2009/0131790 A1 | 5/2009 | Munrow et al. |
| 2009/0171304 A1 | 7/2009 | Cao et al. |
| 2010/0069899 A1 | 3/2010 | Lonero et al. |
| 2010/0121319 A1 | 5/2010 | Chu et al. |
| 2010/0145325 A1 | 6/2010 | Hoey et al. |
| 2010/0168713 A1 | 7/2010 | Tkebuchava |
| 2010/0222668 A1 | 9/2010 | Dalke et al. |
| 2011/0077628 A1 | 3/2011 | Hoey et al. |
| 2011/0087100 A1 | 4/2011 | Grossman |
| 2011/0125108 A1 | 5/2011 | Deviere et al. |
| 2011/0144468 A1 | 6/2011 | Boggs et al. |
| 2011/0230874 A1 | 9/2011 | Epstein et al. |
| 2011/0288412 A1 | 11/2011 | Deckman et al. |
| 2011/0288540 A1 | 11/2011 | Wright et al. |
| 2012/0035474 A1 | 2/2012 | Deckman et al. |
| 2012/0245575 A1 | 9/2012 | Epstein et al. |
| 2012/0310236 A1 | 12/2012 | Placek et al. |
| 2012/0316440 A1 | 12/2012 | Munrow et al. |
| 2013/0096431 A1 | 4/2013 | Vaezy et al. |
| 2013/0137979 A1 | 5/2013 | Deckman et al. |
| 2013/0144283 A1 | 6/2013 | Barman |
| 2013/0296699 A1 | 11/2013 | Deckman et al. |
| 2013/0325052 A1 | 12/2013 | Chang et al. |
| 2014/0073910 A1 | 3/2014 | Munrow et al. |
| 2015/0051594 A1 | 2/2015 | Sobotka |
| 2015/0133911 A1 | 5/2015 | Batchelor et al. |
| 2016/0025055 A1 | 1/2016 | Aleker et al. |
| 2016/0113621 A1 | 4/2016 | Deckman et al. |
| 2016/0220302 A1 | 8/2016 | Zarins et al. |
| 2016/0338628 A1 | 11/2016 | Shah et al. |
| 2017/0065334 A1 | 3/2017 | Wright et al. |
| 2017/0215949 A1 | 8/2017 | Zarins et al. |
| 2017/0245838 A1 | 8/2017 | Munrow et al. |
| 2017/0245891 A1 | 8/2017 | Munrow et al. |
| 2017/0333116 A1 | 11/2017 | Lee et al. |
| 2018/0110554 A1 | 4/2018 | Zarins et al. |
| 2018/0116630 A1 | 5/2018 | Dykes et al. |
| 2018/0318026 A1 | 11/2018 | Placek |
| 2020/0237437 A1 | 7/2020 | Gasperment et al. |

FOREIGN PATENT DOCUMENTS

| | | |
|---|---|---|
| CN | 207245117 U | 4/2018 |
| EP | 1139899 B1 | 8/2006 |
| EP | 1967147 A2 | 9/2008 |
| EP | 1971266 A2 | 9/2008 |
| EP | 1971267 A2 | 9/2008 |
| EP | 2007284 A2 | 12/2008 |
| EP | 1583479 B1 | 3/2009 |
| EP | 2150180 A1 | 2/2010 |
| EP | 2209423 A1 | 7/2010 |
| EP | 2328479 A1 | 6/2011 |
| EP | 2400910 B1 | 6/2015 |
| EP | 3057545 A1 | 8/2016 |
| JP | S6343648 A | 2/1988 |
| JP | 2010118072 A | 5/2010 |
| JP | 6343648 B2 | 6/2018 |
| WO | WO-9734534 A1 | 9/1997 |
| WO | WO-9844857 A1 | 10/1998 |
| WO | WO-2010099481 A1 | 9/2010 |
| WO | WO-2013093924 A2 | 6/2013 |
| WO | WO-2015058096 A1 | 4/2015 |
| WO | WO-2016161011 A1 | 10/2016 |

OTHER PUBLICATIONS

Badawy, et al., Ultrasound-guided transvaginal ovarian needle drilling (UTND) for treatment of polycystic ovary syndrome: a randomized controlled trial, Fertility and Sterility, 91(4):1164-1167 (2009).

El-Edesy, et al., Harmonic Laparoscopic Ovarian Drilling in Polycystic Ovarian Syndrome, AAMJ, 11(3):146-158 (2013).

Extended European Search Report dated May 12, 2020 in EP Patent Appl. Serial No. 20157223.7 (0235).

Extended European Search Report dated Aug. 2, 2017 in EP Patent Appl. Serial No. 14853276.5 (0230).

Fernandez et al., Ovarian Drilling for Surgical Treatment of Polysystic Ovarian Syndrome: A Comprehensive Review; Reproductive BioMedicine Online, 22:556-568 (2011).

Flyckt, et al., Laparoscopic Ovarian Drilling for Clomiphene-Resistant Polycystic Ovary Syndrome, Seminars in Reproductive Medicine, 29(2):138-146 (2011).

Hashim, et al., Three Decades After Gjonnaess's Laparoscopic Ovarian Drilling for Treatment of PCOS; What We Know?, an Evidence-Based Approach, Arch Gynecol. Obstet, 288:409-422 (2013).

Hendriks, et al., Extensive Tissue Damage of Bovine Ovaries After Bipolar Ovarian Drilling Compared to Monopolar Electrocoagulation or Carbon Dioxide Laser, Fertility and Sterility, 93(3):969-975 (Feb. 2010).

International Search Report & Written Opinion dated Mar. 26, 2015 in Int'l PCT Patent Appl. Serial No. PCT/US14/61159 (0210).

International Search Report & Written Opinion dated Jul. 22, 2020 in Int'l PCT Patent Appl. Serial No. PCT/182020/050546 (0410-PCT).

International Search Report & Written Opinion dated Jul. 26, 2016 in Int'l PCT Patent Application Serial No. PCT/US2016/025055 (0310).

Moussatov, et al., A Possible Approach to the Treatment of Polycystic Ovarian Syndrome Using Focused Ultrasound, Ultrasonics, 36(8):893-900 (1998).

Pimentel, et al., Adequacy of Ovarian Diathermy Under Ultrasound Control: an Experimental Model, Journal of Ovarian Research, 6(11):1-7 (Dec. 2013).

Supplementary European Search Report dated Dec. 12, 2018 in EP Patent Appl. Serial No. 16774124.8. (0330).

Syritsa, A., Transvaginal Ultrasound-Guided Electrocautery of the Ovaries in Infertile Patients With Polycystic Ovarian Disease, Int'l J. Gynecology Obstetrics 63:293-294 (1998).

Zhang, et al., Ultrasound-guided transvaginal ovarian needle drilling for clomiphene-resistant polycystic ovarian syndrome in subfertile women, Cochrane Database of Systematic Reviews, Issue 11, Art. No. CD008583 (2021).

Businesswire, "May Health Announces Data From Feasibility Studies of its Novel Ovarian Rebalancing(tm) Treatment and Receives Approval From FDA for Pivotal Trial," Jun. 26, 2023, available at, https://www.businesswire.com/news/home/20230626514249/en/May-Health-Announces-Data-From-Feasibility-Studies-of-its-Novel-Ovarian-Rebalancing%E2%84%A2-Treatment-and-Receives-Approval-From-FDA-for-Pivotal-Trial.

Teede, et al., Recommendations from the international evidence-based guideline for the assessment and management of polycystic ovary syndrome, 33(9):1602-1618 (Sep. 2018).

\* cited by examiner

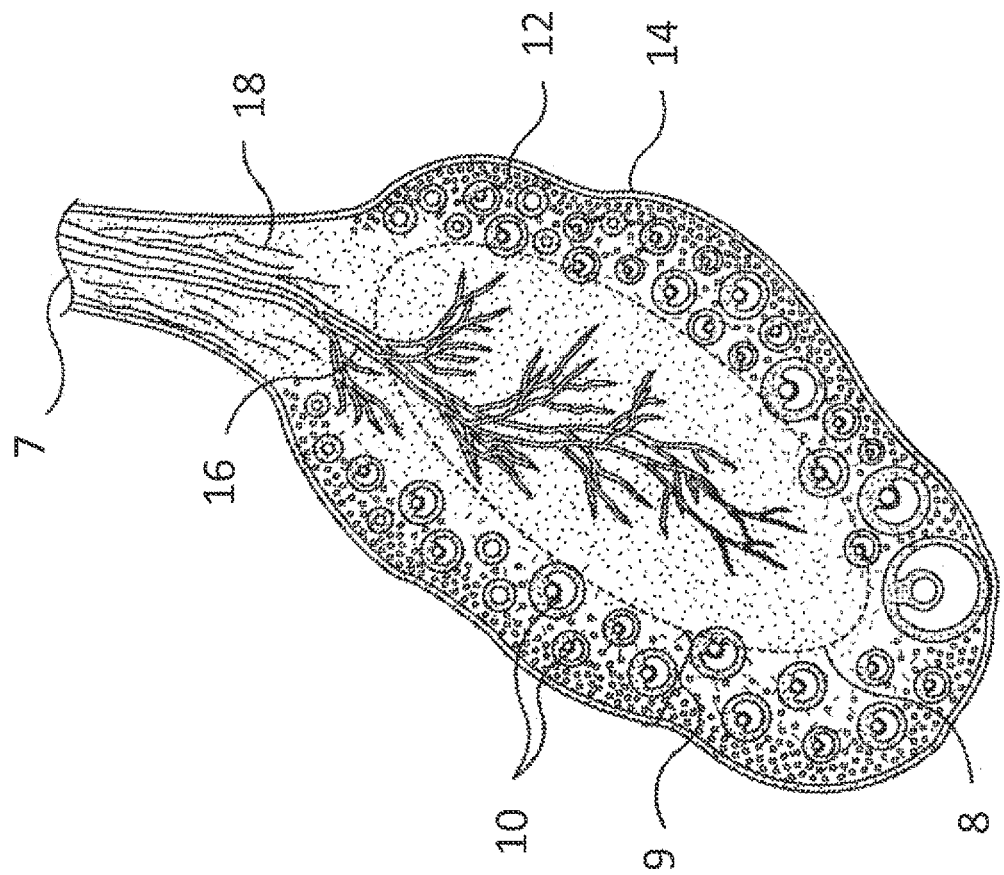
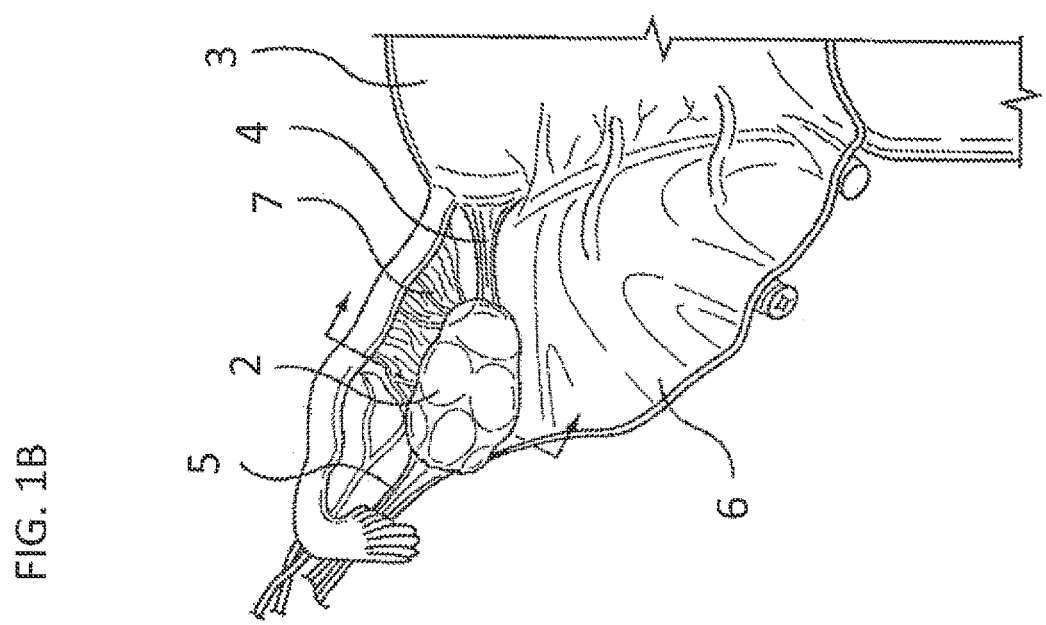
FIG. 1B

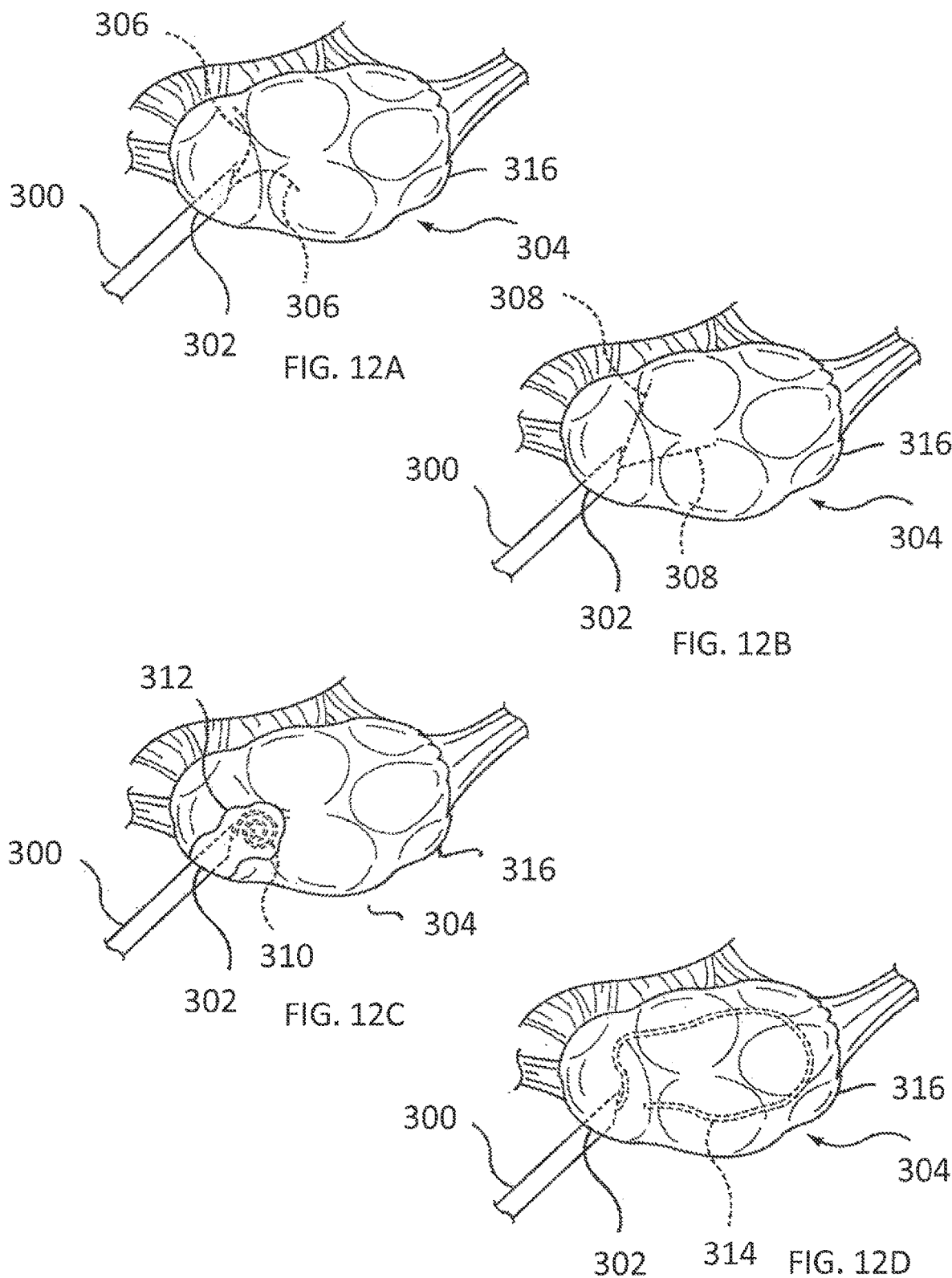

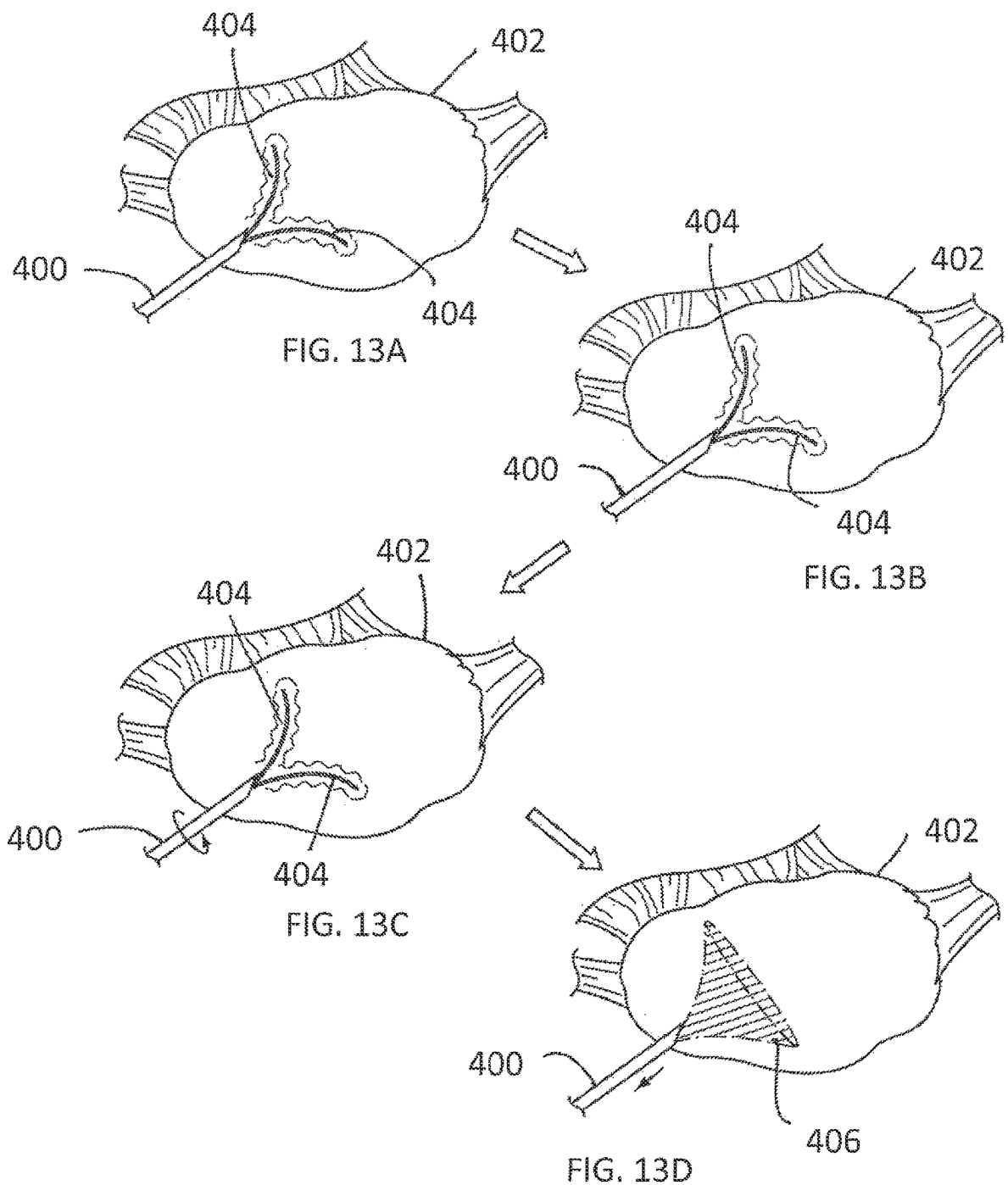

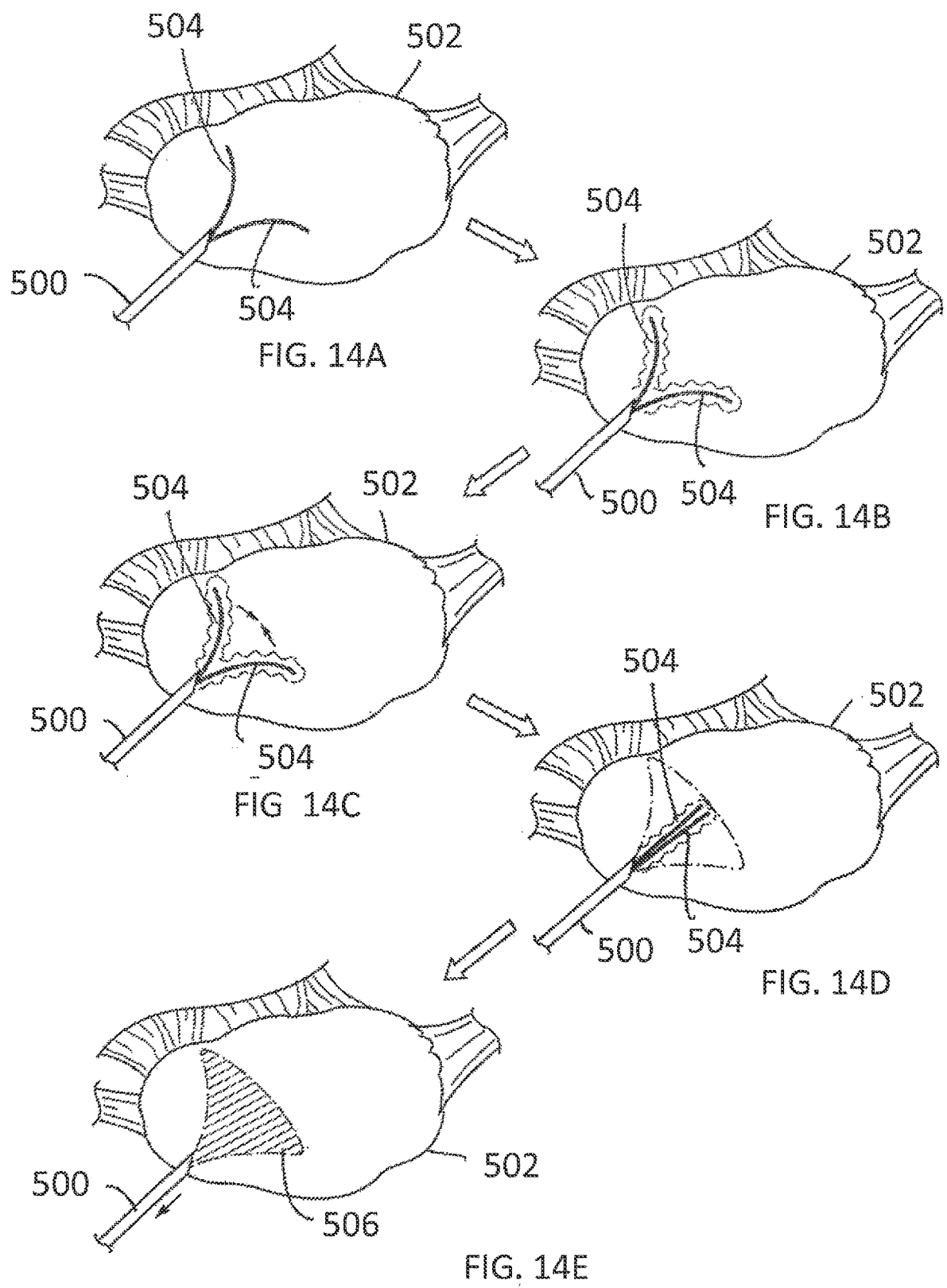

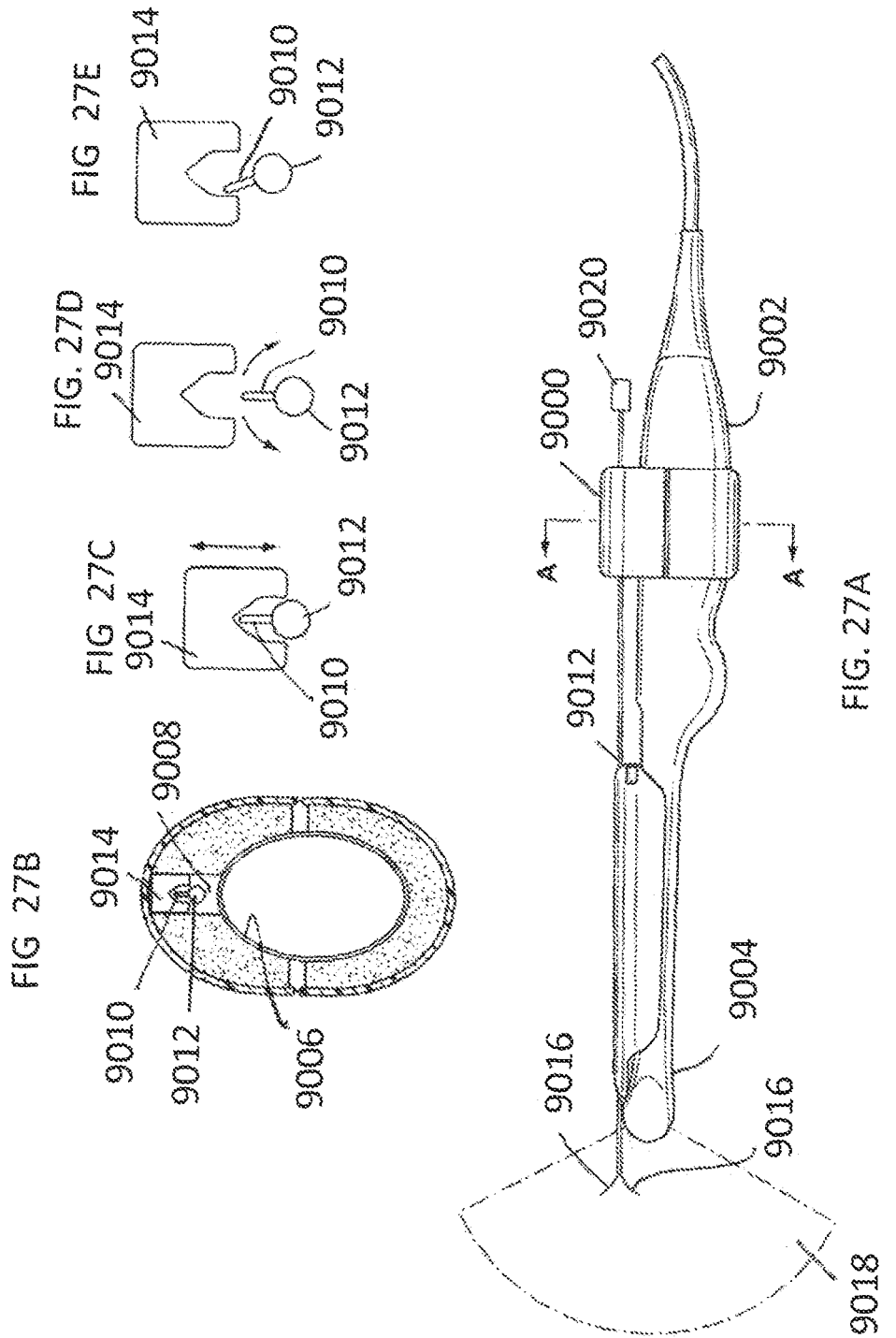

METHODS AND SYSTEMS FOR THE TREATMENT OF POLYCYSTIC OVARY SYNDROME

CROSS-REFERENCE TO RELATED APPLICATIONS

This application is a continuation of U.S. patent application Ser. No. 17/192,870, filed Mar. 4, 2021, which is a continuation of U.S. patent application Ser. No. 16/819,022, filed Mar. 13, 2020, now U.S. Pat. No. 10,939,955, which is a divisional of U.S. patent application Ser. No. 15/494,188, filed Apr. 21, 2017, now U.S. Pat. No. 10,595,936, which is a continuation of U.S. patent application Ser. No. 15/094,852, filed Apr. 8, 2016, which is a continuation of International Application Serial No. PCT/US2014/061169, filed Oct. 17, 2014, which claims priority to U.S. Provisional Patent Application Ser. No. 61/969,042, filed Mar. 21, 2014, and U.S. Provisional Patent Application Ser. No. 61/892,943, filed Oct. 18, 2013, the entire contents of each of which are incorporated herein by reference.

FIELD

Described here are methods and systems for the manipulation of ovalian tissues. The methods and systems may be used in the treatment of polycystic ovary syndrome (PCOS). The systems and methods may be useful in the treatment of infertility associated with PCOS.

BACKGROUND

Polycystic Ovary Syndrome (PCOS) was initially characterized in the 1930s by Stein & Leventhal. Features of the syndrome may include: oligo/amenorrhea, oligo/anovulation, hirsutism, acne, obesity, and characteristic polycystic appearance of the ovaries. PCOS generally has significant effects on reproductive health (e.g., oligo/amenorrhea and oligo/anovulation, bleeding, endometrial hyperplasia, infertility, and increased risk of endometrial cancers) as well as non-reproductive health (e.g., hyperandrogenism, carcinoma, insulin resistance, hypercholesterolemia, hypeltension, obesity, sleep apnea, and cardiovascular disease). PCOS has historically been considered in the context of hormonal dysregulation characterized by alterations in gonadotropin secretion, increased androgen production, increased insulin resistance, increased cortisol production, and obesity. It has also been shown that PCOS is often accompanied by increased activity of the sympathetic nervous system.

Treatment of PCOS can be costly to the health care system. Key non-infertility treatments include: oral contraceptives (for hormonal nonnalization), endometrial ablation (for anovulatory bleeding), insulin sensitizing agents, antihypertensive agents, statins, and treatments for severe acne and hirsutism.

Many women with PCOS may also require infertility treatment during their lifetime. Treatment for PCOS infertility typically follows a step-wise approach. For example, clomiphene citrate is generally the first-line treatment with second-line treatment being either gonadotropin administration or ovarian drilling (also sometimes referred to as ovarian diathermy). If these treatments are unsuccessful, in vitro fertilization (IVF) is attempted. However, multiple pregnancies and live births (e.g., twins) are common with clomiphene citrate, gonadotropin, and IVF treatments. In infertility treatment, multiple pregnancies and live births is often considered an undesirable result due to the associated perinatal and neonatal morbidity and the associated elevated costs. Furthermore, ovarian hyperstimulation syndrome (OHSS) may be more common in women with PCOS undergoing gonadotropin or IVF treatment. While OHSS is often mild and easily treated, more severe cases may require aggressive treatment.

Alternatively, and as mentioned above, ovarian drilling may be an option in treating PCOS, PCOS-associated symptoms/disorders, and PCOS related infertility. Prior to the development of ovarian drilling, many other types of surgery were performed on the ovaries for the treatment of infertility. Ovarian wedge resection, a well-established procedure first described in the late 1940s, involves surgically removing wedge-shaped pieces of ovarian tissue from polycystic ovaries. Despite the effectiveness of the procedure, ovarian wedge resection has generally been abandoned in favor of new techniques because of the frequent occurrence of adhesions with the wedge resection technique. Other ovarian surgeries for infertility in PCOS that have been performed are ovarian electrocautery, ovarian laser vaporization, multiple ovarian biopsies, and others.

Ovarian drilling/diathermy (OD) was developed in the 1970s and 1980s by Gjönnaess. Recently, OD has been the most frequently described ovarian surgery for infertility in women with PCOS. In this laparoscopic procedure, radiofrequency energy, or other techniques, is used to bore multiple holes in the ovary. The physiologic mechanism is not well documented, but there are common findings following the surgery including acute changes in ovarian and pituitary hormones followed by a prolonged reduction of circulating androgens. In randomized trials, rates of pregnancy and live birth have been shown to be similar to those associated with gonadotropin treatment, but with significantly reduced rates of multiple pregnancies and live births.

Despite this evidence, ovarian drilling is not used as frequently in clinical practice as other treatments for PCOS infertility. This may be due to: (1) the lack of standardized, consistent methods of targeting and performing surgeries on the ovary; (2) the invasive nature of current OD technologies; (3) the theoretical risk of adhesions from intervention on the ovaries; (4) the surgical route of access is not a good fit for the clinical practice patterns of fertility physicians; and (5) the uncertainty of the mechanism of action. Accordingly, it would be useful to have systems and methods that overcome the limitations of current surgical procedures. Such systems may be designed to consistently target ovarian tissues, reduce the level of invasiveness of the procedure, reduce the risk of adhesions, and potentially target specific tissue types to act more specifically tissues responsible for the disease. Moreover, given that the ovaries or elements therein may play an important role in governing other female health issues such as timing of menopause, hot-flushes, fibroids, hormonal dysregulation, endometriosis, adnexal pain, risk of endometrial cancer, disturbances in glucose metabolism, or cardiovascular health, it would be beneficial to have improved methods and systems for treating these conditions as well as targeting of structures within or nearby the ovaries that may enable treatment of these conditions.

SUMMARY

Described here are methods and systems for manipulating ovarian tissues within a patient. Exemplary ovarian tissues include without limitation, the ovaries (e.g., medulla/stroma and/or cortex), ovarian follicles/cysts, nerves associated with the ovaries, suspensory ligaments, ovarian ligaments, broad ligaments, the mesovarium, or a combination thereof. In this application, the terms medulla and stroma are used interchangeably. Stromal tissue generally comprises the middle or medullary region of the ovary. The cortex (or outer region) of the ovary is generally where follicles of different degrees of maturity tend to reside. These follicles are sometimes called "cysts" in the setting of PCOS, and in this application, follicle and cyst are used interchangeably. The methods and systems may be used to treat one or more symptoms of, or disorders associated with, polycystic ovary syndrome, including infertility.

In general, the methods and systems are configured to access ovarian tissue or a target region proximate the ovarian tissue transvaginally, laparoscopically, percutaneously, via a natural orifice route through the vagina-uterus-fallopian tubes, through an open surgical approach or via an entirely non-invasive approach. The methods and systems may treat ovarian tissues by mechanical manipulation and/or removal, by delivery of chemical, biologic, or pharmaceutical agents, by delivery of energy, or by applying cooling/cold to the tissues. Exemplary treatment modalities may include without limitation, delivery of one or more of the following: a radiofrequency energy element; a direct heating element; a cryoablation element; a cooling element; a mechanical disruption and/or removal element; laser; a microwave antenna; an unfocused ultrasound element; a partially-focused ultrasound element; a focused (HIFU) ultrasound element; and/or an element for delivering heated water/saline, steam, a chemical ablation agent, a biologic or pharmaceutical agent, implantable pulse generator, a passive or active (e.g., electronic drug delivery unit) drug-eluting implant, a radioisotope seed, or a mechanical implant, which may be either passive or active via application of remote energy (e.g., ultrasound to induce vibration).

The systems described here generally comprise an ovarian tissue apparatus capable of being advanced proximate to or within an ovary, and in the case of PCOS, an ovarian follicle/cyst or other target tissue (e.g., stroma). The ovarian tissue apparatus may also include an engagement device, e.g., a docking device, configured to engage ovarian tissue. The engagement device may be configured to engage the outside surface of the ovary (e.g., the capsule), the outer regions of tissue within the ovary (e.g., the cortex), or the tissue inside the ovary (e.g., medulla, one or more cysts). One or more therapeutic elements can be deployed via the devices to apply one treatment or multiple treatments to the ovarian cyst and/or ovarian tissue. The therapeutic elements may deliver energy, e.g., radiofrequency energy, to effect treatment. The devices and therapeutic elements may be advanced, deployed, or otherwise positioned under image guidance, (e.g., transvaginal ultrasound, transabdominal ultrasound, endoscopic visualization, direct visualization, computed tomography (CT), or magnetic resonance imaging (MRI), optical coherence tomography (OCT), an ultrasound element on the device, or virtual histology). Pre-treatment planning may also be completed prior to performance of the procedure on the target tissue. For example, one or more of the following may be obtained: the size, volume, and/or location of the ovary; the size, volume and/or location of one or more ovarian cysts; and the size, volume, and/or location of the medulla, hormone levels, etc.

According to some embodiments described herein, which may partially or as a whole combine with other embodiments, systems for performing an ovarian procedure may include an ovarian tissue apparatus, the ovarian tissue apparatus comprising a docking device and a therapeutic element, the docking device comprising an elongate body and having a proximal end, a distal end, and defining a lumen therethrough, and the therapeutic element being slidable within and deployable from the lumen of the docking device; a transvaginal probe comprising a handle and an ultrasound transducer; a mechanical lock or a visual identifier on a part of the system; and a generator configured to supply energy to the therapeutic element, where the mechanical lock or visual identifier is configured to maintain planar orientation of the therapeutic element relative to the ultrasound transducer and during a procedure on an ovary. In some instances a non-linear (e.g., curved) therapeutic element may be employed, which allows the therapeutic element to be fully visualized under 2-dimensional ultrasound during therapy delivery, thereby ensuring that non-target tissues are not treated. The curved structure may further aid in anchoring the device in the target tissue, limiting the risk of the device moving during treatment due to patient movement or user error. The curved structure may also be configured to match the contour of the ovary, allowing for improved positioning within a variety of sized or shaped ovaries. Additionally or alternatively, the curved structure may allow for longer or additional electrodes to be delivered and used simultaneously, allowing for larger ablation volumes per energy application. This feature may limit pain experienced by the patient and reduce procedure time. Anchoring either the docking device and/or the therapeutic element in the target tissue may help the user to move the ovary relative to surrounding non-ovary tissues to improve and/or confirm visualization. Moving the ovary may also allow the user to more easily reposition the device for subsequent treatments. Additionally or alternatively, the docking device may be configured to aid in anchoring the device in the target tissue.

According to embodiments described herein, which may partially or as a whole combine with other embodiments, systems for performing an ovarian procedure may include a docking device, the docking device comprising an elongate body and having a proximal end, a distal end, and defining a lumen therethrough; a radiofrequency energy element slidable within and deployable from the lumen of the docking device; a transvaginal probe comprising a handle and an ultrasound transducer; a mechanical lock for releasably coupling the docking device to the probe handle to maintain planar orientation of the radiofrequency energy element relative to the ultrasound transducer during the ovarian procedure; and a generator configured to supply radiofrequency energy to the radiofrequency energy element. In some instances a non-linear (e.g., curved) therapeutic element may be employed, which allows the therapeutic element to be fully visualized under 2-dimensional ultrasound during therapy delivery, thereby ensuring that non-target tissues are not treated. As previously stated, the curved structure may further aid in anchoring the device in the target tissue, limiting the risk of the device moving during treatment due to patient movement or user error. The curved structure may also be configured to match the contour of the ovary, allowing for improved positioning within a variety of sized or shaped[1]"' ovaries. Additionally or alternatively, the curved structure may allow for longer or additional electrodes to be delivered and used simultaneously, allowing for larger ablation volumes per energy application. This feature may limit pain experienced by the patient and reduce procedure time.

Instead of being releasably coupled to the docking device, in some embodiments the mechanical lock is fixedly attached to the docking device. This system embodiment may have a variety of effects therapy. This system embodiment, e.g., may allow for a minimally-invasive, transvaginal approach, wherein the ovary would be accessed using the docking device. By having the docking device resemble a sharp needle, the docking device may be used to puncture through the vaginal wall and into the ovary under transvaginal image guidance. In some cases, this may allow for a single entry point or fewer entry points into the ovary, reducing the risk of adhesions as compared to surgical and laparoscopic approaches with tissue dissection and entry points for each ablation in the ovary. Once in position, the radiofrequency energy element may be deployed into the tissue. In the case where a mechanical lock is used to maintain planar orientation of the radiofrequency element, the radiofrequency element may be non-linear (e.g., curved in a single plane). Here the releasably securable mechanical lock allows the therapeutic element to be flipped 180 degrees so in the case of an asymmetrically shaped therapeutic element, additional regions of the ovary could be accessed and treated without moving the delivery catheter. The non-releasable version of the lock simplifies the user experience when a therapeutic element does not need to be flipped 180 degrees. Since transvaginal ultrasound imaging provides a 2-dimensional image, it is important to maintain the orientation of the radiofrequency element to ensure that the user can see the entire structure. This allows the user to visually observe deployment and confirm position within the ovary or target tissue, adding to the safety and/or effectiveness of the procedure. The advantages of a transvaginal approach over-surgical or laparoscopic approaches generally include one or more of the following: (a) conscious sedation vs. general anesthesia which reduces cost and patient risk, (b) no external scars, (c) less tissue manipulation resulting in lower risk of adhesions, (d) fewer access points into the ovary resulting in lower risk of adhesions, (e) faster recovery time, and (f) it is a familiar access route for OB/GYN and fertility physicians, and fits within existing care pathways.

According to some embodiments described herein, which may partially or as a whole combine with other embodiments, systems described herein may comprise additionally or, alternatively an ultrasound imaging and/or therapeutic element configured to be placed in contact with the abdomen of a patient; an element(s) for operatively connecting the ultrasound imaging and/or therapeutic element to a console, comprised of a user interface, an element(s) for delivering ultrasound for imaging, an element(s) for targeting desired tissue, an element(s) for delivering energy (e.g., partially-focused ultrasound, HIFU), and an element(s) for a feedback control system.

Methods for manipulating ovarian tissue of a patient may include delivering pain management medications systemically and/or locally (e.g., the vaginal wall, the ovary, the mesovarium), accessing a target region proximate an ovarian tissue within the patient; advancing an ovarian tissue apparatus to the target region, the ovarian tissue apparatus comprising a docking device and one or more therapeutic elements, the docking device comprising a proximal end, a distal end, and a distal tip; moving the docking device proximate to or within the ovarian tissue; deploying the one or more therapeutic elements on or within the ovarian tissue; assessing intra-procedural success; and minimizing the occurrence of adhesions as seen with surgical approaches used in the past. The docking device may or may not require physical contact with ovarian tissues.

In some instances, it may be useful to employ methods that minimize the occurrence of adhesion such as performing the procedure via a single entry point or fewer entry points in the ovary (the severity of adhesions may correlate with the number and size of damage to the ovary surface); avoiding injury to the cortex or regions of the cortex closest to the surface (e.g., several millimeters) of the ovary; and leaving behind material anti-adhesive barriers to improve healing at the ovary surface and further reduce adhesion formation. It may also be beneficial to include features for visualizing various portions of the system using imaging as a guide. Depending upon the approach taken (e.g., transvaginal, percutaneous, laparoscopic), the apparatus may include various mechanisms for improving visualization of the portions of the system, e.g., the therapeutic elements.

Methods described herein for delivering energy to an ovary and for treating polycystic ovary syndrome may include advancing a probe comprising a handle, an ultrasound transducer, and a needle guide into the vaginal canal; advancing an ovarian tissue apparatus into the needle guide, the ovarian tissue apparatus comprising a docking device and a therapeutic element; advancing the docking device through a vaginal wall; penetrating an ovary at a single entry point with the docking device or the therapeutic element; advancing the therapeutic element from the docking device into the ovary; and delivering energy to affect a volume of tissue within the ovary using the therapeutic element to treat a symptom of polycystic ovary syndrome; retracting the therapeutic element into the docking device; and removing the ovarian tissue apparatus.

Alternative methods for treating polycystic ovary syndrome as described herein may include advancing an ovarian ablation system into the vaginal canal, the ovarian ablation system comprising a docking device, a radiofrequency energy element, and a transvaginal probe comprising a handle and an ultrasound transducer; advancing the docking device through a vaginal wall under image guidance using the ultrasound transducer; entering an ovary through a single entry point using the docking device or the radiofrequency energy element; advancing the radiofrequency energy element within the ovary; and delivering radiofrequency energy to ablate a volume of tissue within the ovary using the radiofrequency energy element to treat a symptom of polycystic ovary syndrome.

Methods that may be useful in treating polycystic ovary syndrome are also described herein. Such methods generally include advancing an ovarian tissue apparatus proximate a polycystic ovary within a patient, the ovarian tissue apparatus comprising a docking device and one or more therapeutic elements, the docking device comprising a proximal end, a distal end, and a distal tip; deploying the one or more therapeutic elements from the docking device proximate to or within a target tissue, e.g., an ovarian cyst; and manipulating the polycystic ovary to effect a change in the target tissue, one or more symptoms or physiological parameters indicative of polycystic ovary syndrome or its related symptoms, diseases, disorders, or a combination thereof.

Methods that may be useful in controlling pain associated with non-surgical procedures are also described herein. Such methods generally include delivering systemic pharmacologic sedation (e.g., monitored anesthesia care (MAC) or conscious sedation); delivering local anesthesia to the vaginal wall to reduce discomfort in a transvaginal procedure; delivering local anesthesia to the ovary, target tissue, mesovarium, or nerve tissue proximate to the ovary to minimize discomfort associated with application of the therapy; and delivering an epidural to minimize discomfort and patient movement during the procedure.

Methods that may be useful in determining the intra-procedural or post-procedural effect of the procedure are also described herein. Such methods generally include comparing pre-treatment planning parameters (e.g., the size, volume, and/or location of the ovary; the size, volume and/or location of one or more ovarian cysts; the size, volume, and/or location of the medulla; hormone levels) with intra-procedurally-measured parameters or post-procedurally-measured parameters. Examples include: a visible reduction in ovary size or volume, a reduction in the number of cysts, or a reduction in hormone levels, such as anti-mullerian hormone.

According to some embodiments described herein, and which may partially or as a whole combine with other embodiments, systems for manipulating ovarian tissues generally include an ovarian tissue apparatus configured for advancement through the vaginal wall and proximate an ovarian tissue; and an energy generator electrically coupled to the ovarian tissue apparatus, where the ovarian tissue apparatus comprises a docking device and one or more therapeutic elements, the docking device comprising an elongate body having a proximal end, a distal end, a lumen extending from the proximal end through the distal end, and a distal tip. In some instances a non-linear (e.g., curved) therapeutic element may be employed, which allows the therapeutic element to be fully visualized under 2-dimensional ultrasound during therapy delivery, thereby ensuring that non-target tissues are not treated. As previously stated, the curved structure may further aid in anchoring the device in the target tissue, limiting the risk of the device moving during treatment due to patient movement or user error. The curved structure may also be configured to match the contour of the ovary, allowing for improved positioning within a variety of sized or shaped ovaries. Additionally or alternatively, the curved structure may allow for longer or additional electrodes to be delivered and used simultaneously, allowing for larger ablation volumes per energy application. This feature may limit pain experienced by the patient and reduce procedure time. Anchoring either the docking device and/or the therapeutic element in the target tissue may help the user to move the ovary relative to surrounding non-ovary tissues to improve and/or confirm visualization. Moving the ovary may also allow the user to more easily reposition the device for subsequent treatments. Additionally or alternatively, the docking device may be configured to aid in anchoring the device in the target tissue. In some embodiments, a cooling or cryogenic console may be operatively coupled to the ovarian tissue apparatus instead of or in addition to an energy generator. Use of cooling or cryotherapy may limit the amount of pain the patient experiences and may be used in combination with energy to aid in controlling lesion size (e.g., limit conductive heating). Further, combining cooling or cryotherapy with energy may allow for thermally cycling target tissue from cold to hot, resulting in additional cellular injury.

According to some embodiments described herein, and which may partially or as a whole combine with other embodiments, the system may generally include an ovarian tissue apparatus configured for advancement through the vaginal wall and proximate an ovarian tissue; one or more mechanical disruption and/or removal elements; and means for removing target tissue from the body. Mechanical disruption elements may be manipulated manually or automatically (e.g., via a motor and/or drive system). Mechanical manipulations may include rotation, translation and/or vibration. Removal elements may include mechanical instruments for grasping or capturing tissue or a lumen of the apparatus coupled with aspiration or suction. The removed tissue may be used for diagnosis, or components of removed tissue (e.g. oocytes or cellular factors) may be useful in further care. In some embodiment, means for removing target tissue from the body may also include allowing the body's natural healing process to resorb destroyed tissue and/or produce a stable scar.

BRIEF DESCRIPTION OF THE DRAWINGS

FIG. 1B depicts a stylized anatomic view of the structural elements within the ovary.

FIGS. 12A-12F, 13A-13D, 14A-14E, 15A-15B, 16A-16D, 17, 18A-18D, 19, 20A-20C, 21A-21B, and 22 depict embodiments of therapeutic elements and methods for deploying the therapeutic elements for treatment of the ovaries.

FIGS. 27A-27F depict another exemplary method and device for providing planar orientation of therapeutic element(s) during transvaginal ultrasound-guided procedures.

DETAILED DESCRIPTION

Figure 1A:
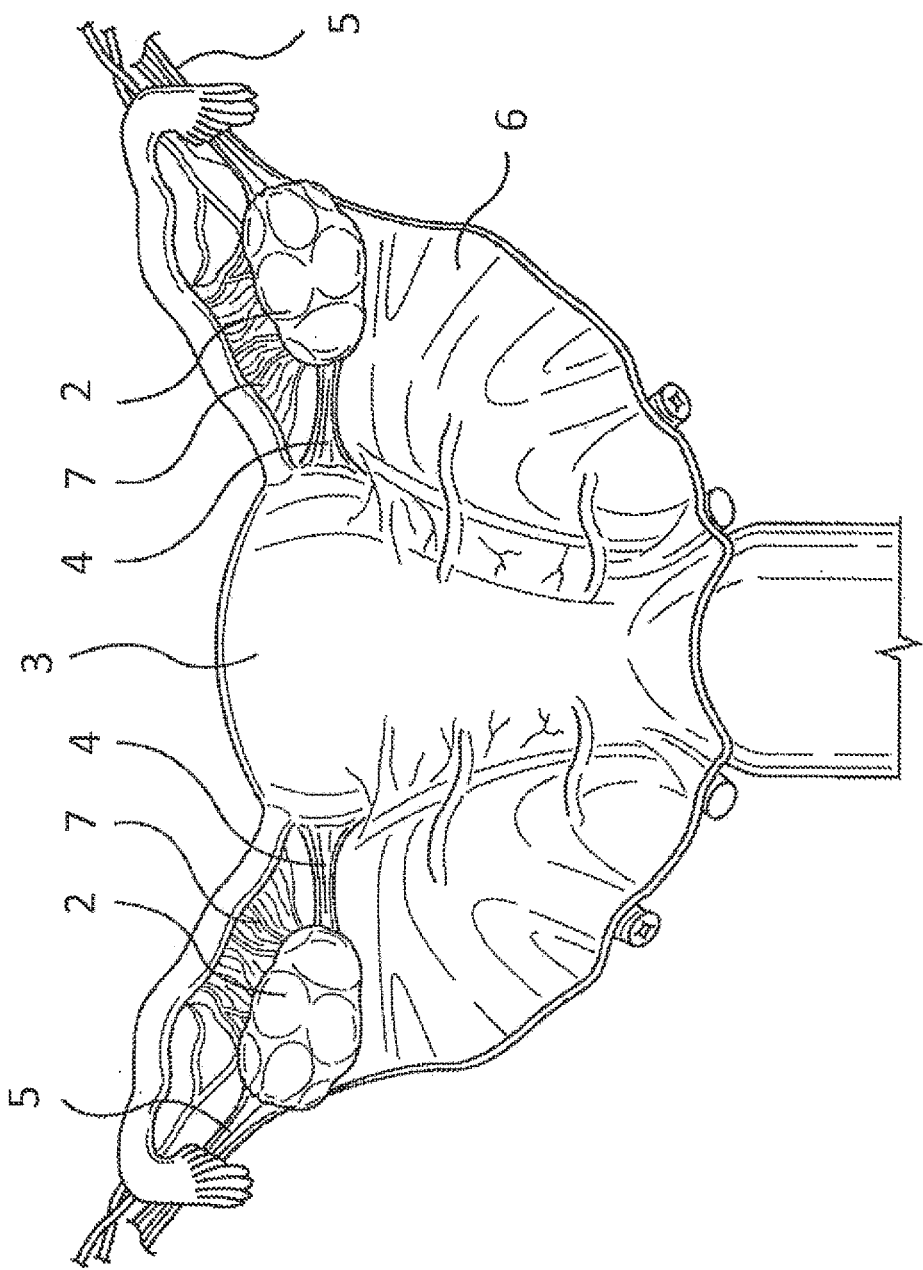
FIG. 1A depicts a stylized, anatomic view of the ovaries, adnexa, uterus, and other nearby structures.

Described here are methods and systems for manipulating ovarian tissues within a patient. The methods and systems may be used in the treatment of polycystic ovary syndrome (PCOS), and may be particularly useful in the treatment of infertility associated with PCOS. As previously stated, exemplary ovarian tissues include without limitation, the ovaries, ovarian cysts, nerves associated with the ovaries, suspensory ligaments, ovarian ligaments, broad ligaments, the mesovarium, or a combination thereof.

In general, the methods and systems are configured to access ovarian tissue or a target region proximate the ovarian tissue transvaginally, laparoscopically, percutaneously, via a natural orifice route through the vagina-uterus-fallopian tubes, through an open surgical approach, or via an entirely non-invasive approach. It may be beneficial to access the ovarian tissue or a target region proximate the ovarian tissue transvaginally. The advantages of a transvaginal approach over surgical or laparoscopic approaches may include one or more of the following: (a) conscious sedation vs. general anesthesia which reduces cost and patient risk, (b) no external scars, (c) less tissue manipulation resulting in lower risk of adhesions, (d) fewer access points into the ovary resulting in lower risk of adhesions, (e) faster recovery time, and (f) it is a familiar access route for OB/GYN and fertility physicians, and fits within existing care pathways. As used herein, the term "transvaginal" or "transvaginally" refers to access through the vagina and into the peritoneal space, through the vaginal wall. The methods and systems may treat ovarian tissues by delivery of one or more of the following: a radiofrequency energy element; a direct heating element; a cryoablation element; a cooling element; a mechanical disruption element; laser; a microwave antenna; an unfocused ultrasound element; a partially-focused ultrasound element; a focused (HIFU) ultrasound element: and/or an element for delivering heated water/saline, steam, a chemical ablation agent, a biologic or pharmaceutical agent, implantable pulse generator, a passive or active (e.g., electronic drug delivery unit) drug-eluting implant, or a mechanical implant, which may be either passive or active via application of remote energy (e.g., ultrasound to induce vibration).

When the methods and systems employ an image guided energy delivery element (therapeutic element), it may be useful to maintain planar orientation of the energy delivery element with an imaging plane of view, as further described below. In the case of a non-linear (e.g., curved) therapeutic element, this allows for the therapeutic element to be fully visualized under 2-dimensional imaging during therapy delivery, thereby ensuring that non-target tissues are not treated. Furthermore, when performing an ovarian procedure with the systems described herein, it may be beneficial to minimize the number of entry points into the ovary (the severity of adhesions may correlate with the number and size of damage to the ovary surface). After accessing the ovary through the single entry point, energy may be delivered from inside the ovary (instead of from outside the ovary) to affect a volume of tissue and/or treat polycystic ovary syndrome. For example, the number of ablations needed to affect the desired volume of tissue may vary, but could range from 1-10 ablations.

To further understand the methods and systems described herein, a brief overview of female reproductive anatomy is provided. Referring to FIG. 1A, the paired ovaries (2) lie within the pelvic cavity, on either side of the uterus (3), to which they are attached via a fibrous cord called the ovarian ligament (4). The ovaries (2) are uncovered in the peritoneal cavity but are tethered laterally to the body wall via the suspensory ligament (5) of the ovary, The part of the broad ligament (6) of the uterus that suspends the ovary is known as the mesovarium (7). FIG. 1B is an expanded, cross-sectional view of the ovary (2) and surrounding structures shown in FIG. 1A. Referring to FIG. 1B, the stroma or medulla (8) comprises the middle or medullary region of the ovary; the cortex (9) (or outer region) of the ovary tends to be where follicles (10) of different degrees of maturity reside; primordial follicles (12), which are very small and immature follicles, comprise a reserve of future follicles for ovulation; a capsule (14) encases the ovary (2), which is tethered to the broad ligament (6) by the mesovarium (7); small blood vessels (16) and nerves (18) enter the ovary (2) through the mesovarium (7), the ovarian ligament (4), and the suspensory ligament (5) of the ovary.

Figure 29:
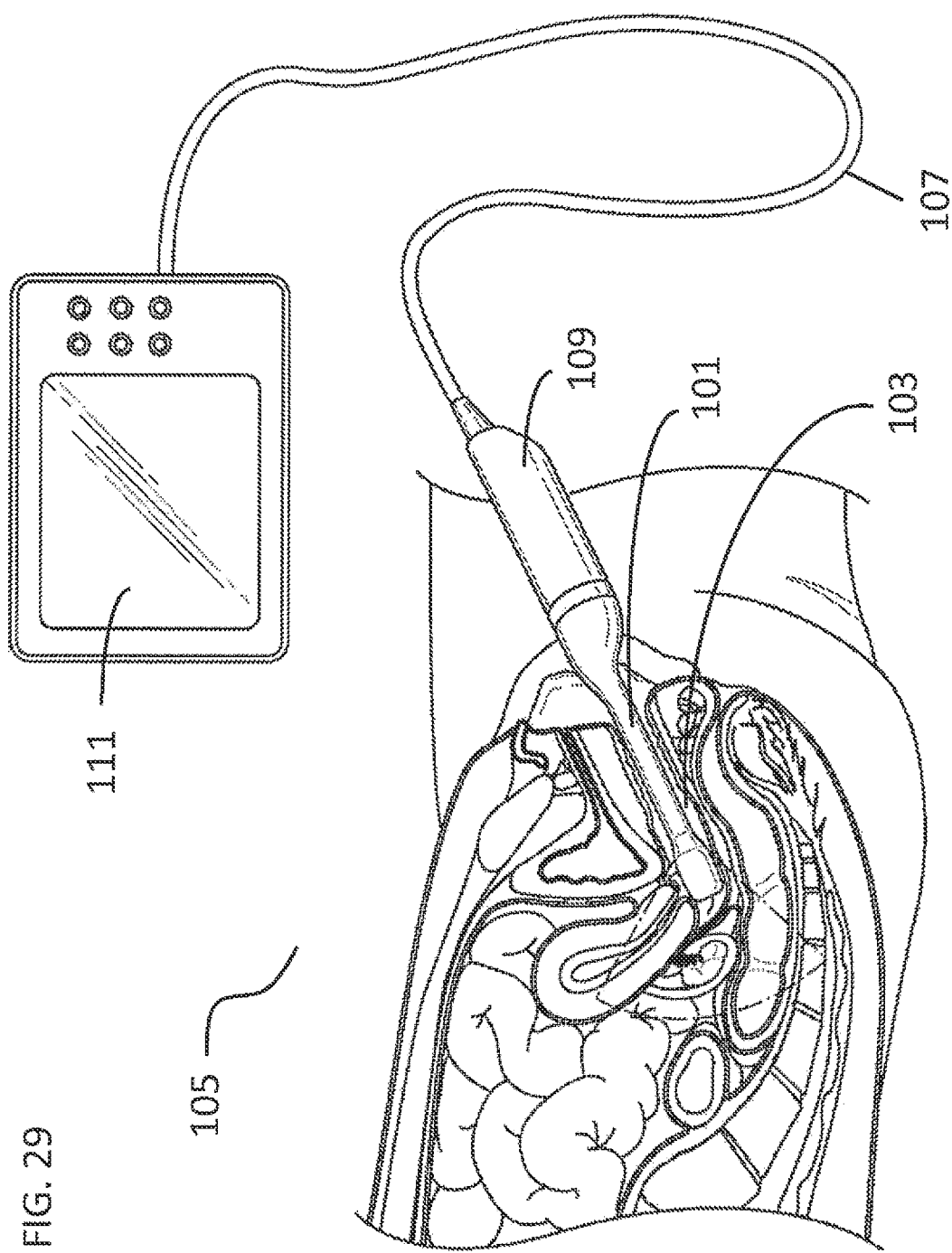
FIG. 29 illustrates an exemplary method of accessing ovarian tissue transvaginaily.
Figure 30:
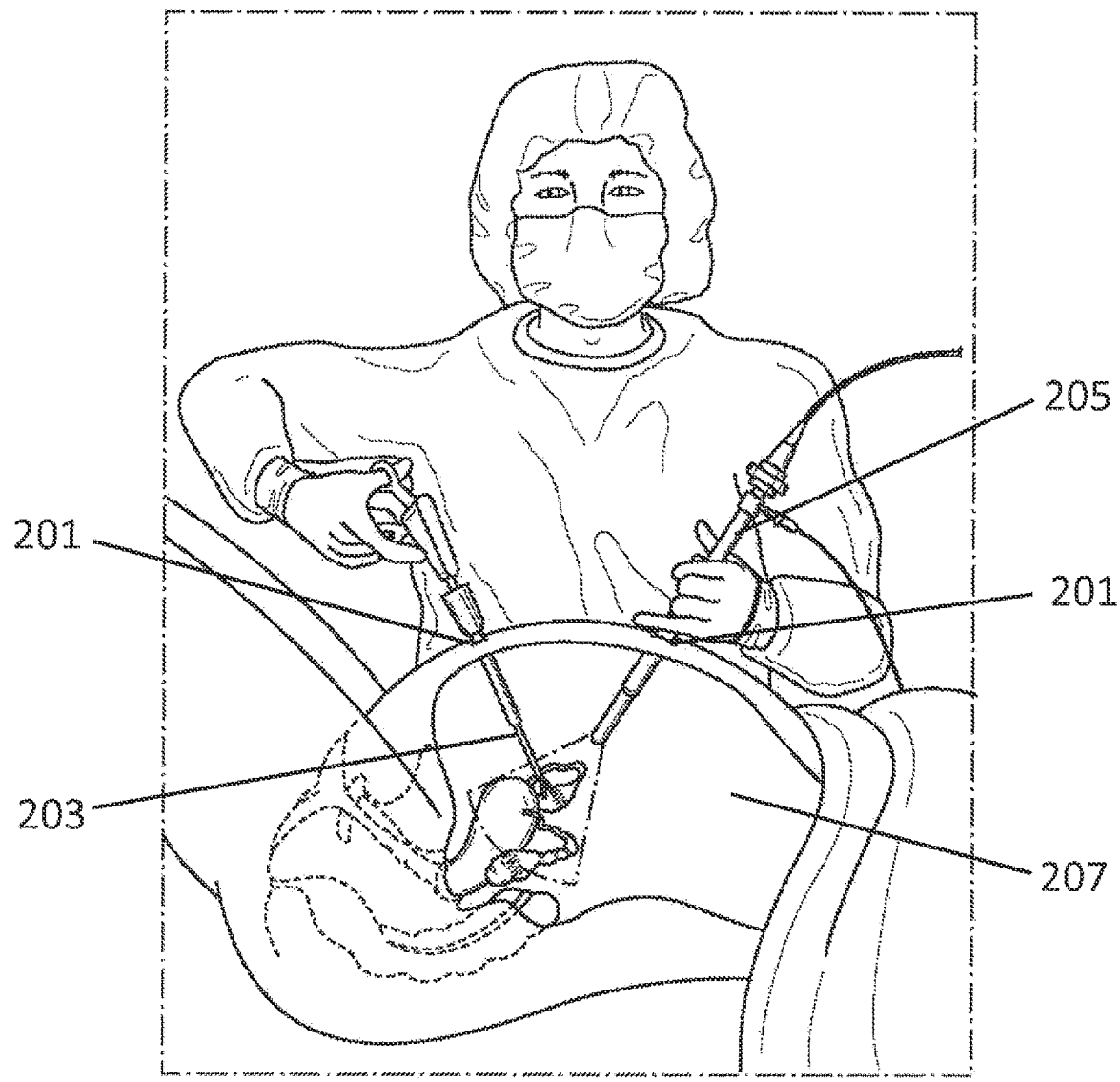
FIG. 30 illustrates an exemplary method of accessing ovarian tissue laparoscopically.

A brief overview of several approaches to accessing ovarian tissue is also provided, as depicted in FIG. 29. Referring to the figure, a system for performing transvaginal ultrasound is shown. An ultrasound probe (101) is placed inside the vagina (103) of the patient (105). A cable (107) connects the handle (109) of the probe to a monitor (111), allowing the user to visualize the ultrasound images. A typical laparoscopic procedure is illustrated in FIG. 30. The laparoscopic approach typically employs 2 or 3 small incisions (201), through which various imaging and surgical tools (203) can be introduced. Imaging is performed with a laparoscope (205), which allows for direct visualization of tissues. The abdominal cavity is filled with gas (207) to expand the field of view and allow for manipulation of tissues.

I. Methods

Disclosed herein are various methods for manipulating the ovarian tissues of a patient. Manipulation of the ovarian tissues may occur by mechanical manipulation of the tissues, by delivery of chemical, biologic or pharmaceutical agents, cooling/cryotherapy, or by delivery of energy to the tissues. Although the ovarian tissues may be accessed using any suitable approach, the methods described here generally use a transvaginal approach. The type of approach utilized may depend on factors such as a patient's age, comorbidities, need for other concomitant procedures, and prior surgical history. Furthermore, in some instances it may be desirable to provide protective elements and/or spacing devices configured to spare or separate non-target tissues, or to prevent excessive damage to the tissues. In some cases, for example thermal treatment, the protective element can be the use of a temperature sensor (e.g. a thermocouple or thermistor), and/or an active cooling member (e.g., internally cooled electrode, irrigated electrode, irrigated guide/docking device, etc., if heat is generated). Embodiments of spacing devices may include mechanical features incorporated into an apparatus and/or fluid infusion into the region proximate to the ovary (e.g., the peritoneal space). In some embodiments, the aspiration and irrigation functions are performed via the same lumen within the apparatus.

In one variation, the method includes accessing a target region proximate an ovarian tissue within the patient; advancing an ovarian tissue apparatus to the target region, the ovarian tissue apparatus comprising a docking device and one or more therapeutic elements, the docking device comprising a proximal end, a distal end, and a distal tip; contacting the ovarian tissue with the docking device; and deploying the one or more therapeutic elements on or within the ovarian tissue.

The docking device of the ovarian tissue apparatus may be advanced using image guidance. Image guidance may be accomplished using techniques such as but not limited to, transvaginal ultrasound, transabdominal ultrasound, endoscopic visualization, direct visualization, computed tomography (CT), or magnetic resonance imaging (MRI). optical coherence tomography (OCT), an ultrasound element on the device, virtual histology, or a combination thereof. In some embodiments, for example alternatively or in conjunction with image guidance, advancement and navigation of the docking device may be accomplished using a steering mechanism at least partially disposed within the distal end of the docking device. For example, one or more steerable wires may be disposed within the docking device running from the proximal end to the distal tip of the device. Actuation of the steerable wires may occur by manipulation of a mechanism on a handle at the proximal end of the docking device. In some embodiments, the docking device comprises a flexible distal end, or one or more flexible segments to aid with navigation to the target ovarian tissue. In other embodiments, the docking device comprises a rigid member, which may have a sharpened tip. Proximal portions of the docking device may be reinforced, e.g., with a braided shaft, material of increased durometer, to provide improved pushability and torque control.

The ovarian tissue may be engaged in various different ways. In some variations, the step of contacting comprises applying vacuum to the ovarian tissue using the distal tip of the docking device. In other variations, the step of contacting comprises releasably securing one or more attachment elements to the ovarian tissue. The attachment elements may comprise any suitable element capable of releasably securing ovarian tissue. Embodiments of such attachment elements include a hook, needle, barb, or combination thereof, When vacuum is used to help engage the docking device to a polycystic ovary, the vacuum may also be used to aspirate fluid from one or more cysts. Aspiration of cyst fluid may reduce the size of the cyst or reduce the total number of cysts on the ovary. By reducing the size of the cyst, the tissue may be drawn closer to or into contact with the therapeutic element(s), which may allow for improved targeting of tissue (e.g., thecal cells) and/or shorter treatments times. Aspiration of fluid may also aid in the assessment that bleeding has been controlled after delivery of the therapy.

According to some embodiments described herein, which may partially or as a whole combine with other embodiments, the distal end of the docking device comprises a tissue engagement element, and the ovarian tissue is contacted using the tissue engagement element. In some embodiments, the tissue engagement element comprises a preformed shape, e.g., a predetermined curvature. The preformed shape may conform to the shape of the ovarian tissue, and aid in the deployment of the treatment elements from the docking device. One or more therapeutic elements may be deployed from the docking device on, into, or proximate to the ovarian or mesovarian tissue. When the ovarian tissue is an ovary, the size of the ovary may range from about 3 to 7 cm in length, about 1 to 4 cm in width, and about 0.5 to 4 cm in thickness. Ovaries stimulated by pharmaceutical agents such as gonadotropins may often be larger.

According to embodiments described herein, which may partially or as a whole combine with other embodiments, the therapeutic element may comprise one or more of the following: a radiofrequency energy element; a direct heating element; a cryoablation element; a cooling element; a mechanical disruption element; laser; a microwave antenna; an unfocused ultrasound element; a partially-focused ultrasound element; a focused (HIFU) ultrasound element; and/or means for delivering heated water/saline, steam, a chemical ablation agent, a biologic, or pharmaceutical agent, implantable pulse generator, a passive or active (e.g., electronic drug delivery unit) drug-eluting implant, a radioisotope seed, or a mechanical implant, which may be either passive or active via application of remote energy (e.g., ultrasound to induce vibration). In some embodiments, the therapeutic element comprises a radiofrequency energy element, e.g., a radiofrequency electrode. In some embodiments, the therapeutic element may comprise one or more curved needle electrodes. Additionally or alternatively, the therapeutic element may comprise one or more straight or curved wire electrodes. According to embodiments described herein, which may partially or as a whole combine with other embodiments, the therapeutic element may comprise one or more active electrodes on an elongate body. Here a return electrode may be provided on the distal end of the docking device, or be deployable from the docking device. Alternatively, a return electrode may be placed on the outside of the patient. For example, in one variation, a return electrode may be affixed to the ultrasound probe proximate the transducer. In another variation, a return electrode may be incorporated into a needle guide. In the case of a plurality of electrodes, any pair may be activated in a bipolar manner or individually via a return electrode. With regards to the use of the various types of ultrasound, it could include variations that use ultrasound to create thermal heating or non-thermal ultrasound to induce acoustic cavitation.

Mechanical disruption elements could include mechanical disruption of one or more target tissues (e.g., medulla, cortex, nerves, cysts, etc.). The mechanical disruption may include morcellating, tearing, compressing, stretching or otherwise destroying tissue or causing it to alter its function (e.g., induce apoptosis, trigger increased blood flow, trigger a healing response, trigger maturation of oocytes, or trigger ovulation). Injured/destroyed tissue may be removed mechanically or left within the body, allowing the body's natural healing process to resorb the destroyed tissue. The morcellated tissue may also be retrieved in some instances if it can be used for diagnosis, or if components of the removed tissue (e.g., oocytes or cellular factors) may be useful in further care. Pharmacologic or biologic agents could be delivered either as a onetime delivery, part of a slow-release preparation, or implanted as a part of a biodegradable or non-biodegradable device. These agents could also be implanted within a casing (e.g., an electronic drug delivery unit) configured to remotely control delivery of the casing's contents using a controller external to the body. Exemplary biologic or pharmacologic agents that could be employed include without limitation: beta-blockers, antiandrogens (e.g., finasteride, flutamide, nilutamide, bicalutamide. spironolactone, cyproterone), follicular stimulating hormone, luteinizing hormone, other hormones, neurotoxins or tissue toxins (e.g., botox, guanethidine, ethanol), 5-alpha-reductase inhibitors (e.g., finasteride, dutasteride, izonsteride, turosteride, and episteride), insulin modulating agents, aromatase inhibitors (e.g., letrozole, exemestane, anastrozole), VEGF modulating agents, agents modulating inhibin, agents modulating interleukins, pluripotent or muldpotent stem cell preparations, or cellular components. Furthermore, an agent (e.g., radiopaque material, echogenic material, etc.) may be left behind to tag the location(s) in which the therapeutic agent(s) are delivered.

In one valuation, one or more therapeutic elements are advanced on or into an ovary. In another variation, the one or more therapeutic elements are advanced on or into an ovarian cyst. The one or more therapeutic elements may also be advanced from the mesovarium on or into an ovary or an ovarian cyst. In one variation, the one or more therapeutic elements are delivered to multiple, predetermined areas on or within the ovarian tissue. In other instances, a pattern of treatment is delivered on or into the ovarian tissue. These patterns of treatment within the tissue could be linear, curvilinear, helical, interrupted, continuous, arbor-like (e.g., with a trunk and multiple offshoots), or may comprise other suitable patterns. The therapeutic elements may be utilized such that multiple treatments may be delivered through a single outer entry point in the ovary. The therapeutic elements may be delivered to treat any suitable medical condition of the female reproductive anatomy, and may be particularly beneficial in the treatment of polycystic ovary syndrome.

Some variations of the method deliver thermal energy to the ovarian tissues. The thermal energy may increase the temperature of the ovarian tissue (e.g., by healing) and/or ablate/coagulate and/or desiccate/char the tissue. The thermal energy may also be delivered to reduce the temperature of the ovarian tissue (e.g. by cooling) or may cryoablate the tissue. Mechanically disrupting the ovarian tissues with the one or more therapeutic elements is also contemplated. For example, a steerable device could be used under image guidance to maximize the number of ovarian cysts that are ruptured as it was advanced in a path through the ovarian tissue, this could be done alone or in combination with some form of thermal energy. The mechanically disrupting portion of the device could rupture a cyst, then imaging could identify rupturing a subsequent cyst, and the process could be repeated.

Methods useful in treating PCOS may include advancing an ovarian tissue apparatus proximate a polycystic ovary within a patient, the ovarian tissue apparatus comprising a docking device and one or more therapeutic elements, the docking device comprising a proximal end, a distal end, and a distal tip; deploying the one or more therapeutic elements from the docking device proximate to or within an ovarian cyst; and manipulating the polycystic ovary or ovarian cyst to effect a change in the ovarian cyst, one or more symptoms or physiological parameters indicative of polycystic ovary syndrome, or a combination thereof. An implantable pulse generator could be used to apply periodic electric energy to modulate the neurohormonal environment of the ovary. The implantable pulse generator could be used to deliver energy proximate to various ovarian structures (e.g. cortex, stroma, nerves, mesovarium). In some variations of the method, the one or more therapeutic elements are deployed from the docking device proximate to or within an additional ovarian cyst. When the polycystic ovary or ovarian cyst is manipulated, symptoms such as infertility, anovulation, acne, obesity, abdominal pain, hirsutism, or psychological symptoms may be treated or improved. Physiological parameters of the patient that can be affected by manipulation of the polycystic ovary or ovarian cyst may include androgen levels, number or size of ovarian cysts, size of the ovary, levels of anti-müllerian hormone (AMH), sex hormone binding globulin, level of luteinizing hormone (LH), ratio of luteinizing hormone (LH) to follicular stimulating hormone (FSH), lipid levels, fasting blood glucose, fasting blood insulin levels, response to oral glucose tolerance testing, blood glucose level, or measures of sympathetic nervous system activity (e.g., microneurography, norepinephrine spillover testing, or heart rate variability). In one aspect of the PCOS treatment described herein, a test of physiologic parameters can be performed pre-procedurally, peri-procedurally or post-procedurally to guide therapy and/or confirm clinical success of the treatment.

The ovarian tissue apparatus, including the docking device, may be advanced transvaginally, laparoscopically, percutaneously, via a natural orifice route through the vagina-uterus-fallopian tubes, through an open surgical approach, or via an entirely non-invasive approach. The steps of advancing, deploying, and manipulating may be accomplished using image guidance, including but not limited to transvaginal ultrasound, transabdominal ultrasound, endoscopic visualization, direct visualization, computed tomography (CT), or magnetic resonance imaging (MRI), optical coherence tomography (OCT), an ultrasound element on the device, virtual histology, or a combination thereof. In the case of an entirely non-invasive approach, the steps may include positioning an imaging and/or therapeutic element on the abdomen of a patient, identifying target tissue, targeting said tissue, and applying energy (e.g., partially-focused or focused ultrasound). Hybrid approaches may also be utilized. For example, transvaginal ultrasound may be used for imaging and/or targeting, while an external therapeutic element could deliver energy. Further, having ultrasound visualization in both the vagina and on the abdomen may enhance targeting.

Alternatively, or in conjunction with image guidance, and as previously described, advancement and navigation of the docking device may be accomplished using a steering mechanism at least partially disposed within the distal end of the docking device. For example, one or more steerable wires may be disposed within the docking device running from the proximal end to the distal tip of the device. Actuation of the steerable wires may occur by manipulation of a mechanism on a handle at the proximal end of the docking device. In some embodiments, the docking device comprises a flexible distal end, or one or more flexible segments to aid with navigation to the target ovarian tissue. Proximal portions of the docking device may be reinforced, e.g., with a braided shaft, material of increased durometer, to provide improved pushability and torque control.

The docking device may use a docking mechanism such that a portion of the device arrives proximate to or to engages the polycystic ovary, an ovarian cyst, or the mesovarium. In some embodiments, the docking mechanism includes the application of vacuum to the ovarian tissue using the distal tip of the docking device. Alternatively or additionally, the docking mechanism comprises releasably securing one or more attachment elements to the polycystic ovary. The attachment elements may comprise any suitable element capable of releasably securing the polycystic ovary. Exemplary attachment elements include a hook, needle, barb, or combination thereof. When vacuum is used to help engage the docking device to a polycystic ovary, the vacuum may also be used to aspirate fluid from one or more cysts. Aspiration of cyst fluid may reduce the size of the cyst or reduce the total number of cysts on the ovary. Aspiration may be used prior to, during, or after delivery of the therapeutic element so that the therapeutic element is more proximate to target tissue. Aspiration of fluid may also aid in the assessment that bleeding has been controlled after delivery of the therapy. The aspirated fluid could also be collected and analyzed for another purpose.

In some embodiments, the distal end of the docking device comprises a tissue engagement element, and the polycystic ovary is contacted using the tissue engagement element. In some instances, the tissue engagement element comprises a preformed shape, e.g., a predetermined curvature. The preformed shape may conform to the shape of the ovary, and aid in the deployment of the treatment elements from the docking device.

In some embodiments, the guiding/docking device and the therapeutic element are combined into a single entity. In other embodiments, the guiding/docking device and the therapeutic element are different but the two are used in tandem to deliver therapy (e.g., the guiding/docking device has a therapeutic element such as an electrode that may be used in combination or separate from other deployed therapeutic elements. Alternatively, the electrode located on the guiding/docking device may be used as a neutral electrode with little/no therapeutic effect (e.g., heat).

Figure 31:
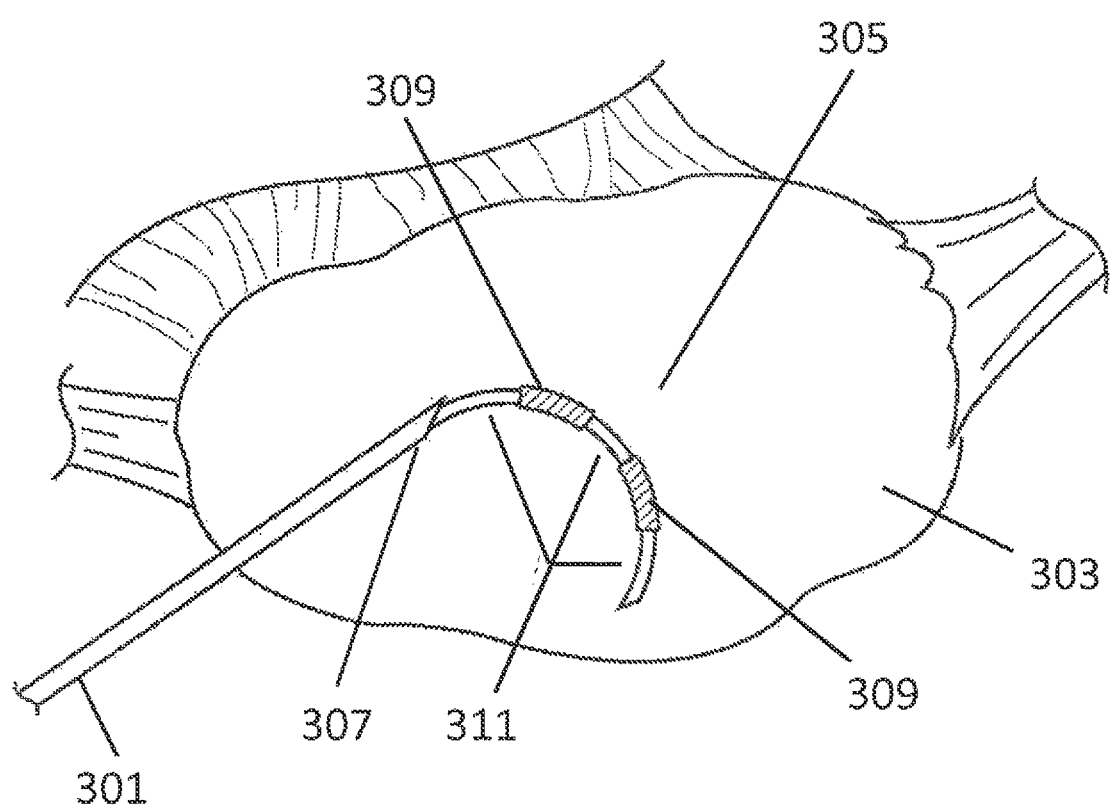
FIG. 31 depicts another embodiment of a system and method for ablating ovarian tissue.

In some aspects, the methods employed herein include using a docking/guiding device to penetrate the ovary and permit delivery of one or multiple therapeutic elements out of one or more apertures in the guiding/docking device. In some embodiments, the docking/guiding device may comprise, for example, a needle, and the therapeutic element may comprise, for example, a shaft one electrode or a plurality of electrodes. In some embodiments, the shaft may be straight, but in other embodiments, the distal portion of the shaft may be processed to have a pre-set shape. The therapeutic element may be insulated along the majority of its length or a discrete portion(s) of its length to electrically isolate it from the docking device. In some embodiments, the electrodes may wrap around the entire circumference of the shaft or may only cover a portion of the shaft circumference in other embodiments. In each of the embodiments described in the present disclosure, the electrodes could be electrically isolated from each other and deliver energy in a monopolar or bipolar fashion. Monopolar configurations may allow for simpler device configuration, but they require a neutral electrode. Bipolar configurations may allow for energy to be contained within a more limited field of tissues. When a bipolar method is used, one electrode would serve as the active electrode and another electrode would serve as the return electrode. In further embodiments, multiple electrodes could deliver energy and the energy would return to a neutral electrode located elsewhere, such as on the skin of the patient, on the docking/guiding device, or on the ultrasound probe. In some embodiments, the electrodes could also be electrically connected to each other and deliver energy where the return or neutral electrode is located elsewhere, such as on the skin of the patient, on the docking/guiding device, or on the ultrasound probe. Placing the neutral electrode on the outside of the patient (e.g., skin) may allow for a simpler device configuration. Placing the neutral electrode on the docking/guiding device or the ultrasound transducer may help confine the energy delivery to a smaller field and also change the diagnostic information collected by impedance measurements. As shown in FIG. 31, a docking/guiding device (301) can be used to penetrate into the ovary (303) and deliver a single therapeutic element (305) out of the distal end (307) of the docking/guiding device (301). Here the therapeutic element is delivered from the docking device at an angle away from the trajectory of the docking/guiding device but within the two-dimensional plane of an ultrasound field. Docking/guiding device (301) may comprise a needle and the therapeutic element (305) may include a curved shaft with two electrodes (309) disposed thereon. The electrodes (309) may be comprised of metallic bands, coils, wires (e.g., wound or braided), laser cut tubing, or slotted tubular structures. They may wrap entirely around the circumference of the therapeutic element shaft (305) and may be separated by discreet insulated areas (311). Additional detail relating to these devices and similar embodiments is provided below.

One or more therapeutic elements may be deployed from the docking device on or into the polycystic ovary, proximate to or into an ovarian cyst, proximate to or into the mesovarium, or other target structure. The one or more therapeutic elements may also be advanced from a single docking location or multiple docking locations on or within the polycystic' ovary or an ovarian cyst; or advanced from a single docking location or multiple docking locations proximate to an ovarian cyst, or proximate to the mesovarium.

The docking location(s) could be on the medial and/or inferior aspect of the ovary. The guiding/docking device could also penetrate into the ovary. In one aspect of the methods, there may be a single entry point on the outside of the ovary (by either the guiding/docking device or the treatment element or the combination thereof) through which multiple treatments could be delivered thereby causing less damage to the outside of the ovary and reducing the risk for adhesion formation. In another variation, the energy is delivered to multiple, areas on or within the polycystic ovary, an ovarian cyst, proximate to an ovarian cyst, proximate to the junction of the ovarian stroma and cortex, or proximate to the mesovarium allowing improved targeting or avoidance of certain tissues (e.g., nerves or vasculature). In other instances, a pattern of treatments is delivered on or within the polycystic ovary, an ovarian cyst, proximate to an ovarian cyst, proximate to the junction of the ovarian stroma and cortex, or proximate to the mesovarium.

Another aspect of the methods disclosed herein comprises orienting the therapeutic element(s) with the transvaginal ultrasonic probe, which is generally limited to 2-dimensional (or planar) imaging. When the therapeutic element has a non-linear geometry, e.g., if it is curved, it is desirable to maintain visualization of the therapeutic element via the transvaginal ultrasound probe. Here the method may include setting the orientation of the therapeutic element in plane with the ultrasonic probe such that as the therapeutic element is maneuvered or deployed, the operator can visualize it. This may be employed via the method of attaching the therapeutic device to the handle of the ultrasound probe and/or by employing a needle guide configured to attach to the ultrasound probe and provide a unique guiding interface with the guiding/docking device. The method may also involve a means to quickly decouple the orientation between the therapeutic element and the visualization plane of the probe. For example, the operator may choose to deploy the therapeutic element in one plane but then rotate the ultrasound probe into another plane (without changing plane of the therapeutic element) to verify placement or view other surrounding tissues. According to some embodiments, the coupling mechanism between the therapeutic element and probe could provide a means of sliding or rotating the probe into a new orientation but then quickly realigning the therapeutic element and probe (such that the deployed element is back in the visualization plane of the probe). In some instances, it may be desirable to reorient the therapeutic element by exactly 180 degrees to allow for it to reach different regions of tissue in the same imaging plane.

Another aspect of the methods disclosed herein comprises enhancing the visualization (i.e., echogenicity) of the guiding/docking device and/or therapeutic elements while using ultrasound for visualization. The method may include providing a region of increased echogenicity on the guiding/docking device and/or therapeutic elements. In some embodiments, the region of increased echogenicity is a region that traps gas. In some embodiments, the region of increased echogenicity includes a roughened surface covered by a polymer sheath, which traps gas between the grooves of the roughened surface and the polymer sheath. The trapped gas enhances the echogenicity beyond using merely a roughened surface. In other embodiments, gas may also be trapped by incorporating one or more lumens, pockets, or cavities within the therapeutic element and/or the docking device. It may be useful to have enhanced echogenicity only at the distal tip of the therapeutic element and/or docking device, which could aid in ensuring that it is within the desired target tissue. For example, enhanced echogenicity at the distal tip may help with visualization of the tip within the ovary, and indicate that a region proximal to the tip is contained within the ovary. It may also be useful to have differential echogenicity of different parts of therapeutic element and/or docking device to provide better assessment of device placement. In some instances it may be useful for the therapeutic element or a portion thereof to comprise an echogenic material having greater echogenicity than the echogenic material of the docking device or other portions of the therapeutic element.

Alternatively, the methods provided herein may include limited rotation and/or translation of the guiding/docking device and/or therapeutic elements while using ultrasound to enhance visualization. For example, rotation of plus or minus up to 20 degrees of rotation could significantly improve visualization. The limited rotation may be useful in maintaining the therapeutic elements within the ultrasound visualization plane (if so desired) while allowing the operator to quickly rotate the device back and forth to enhance visualization. In other variations of the method, translation plus or minus up to 0.25 mm may also significantly improve visualization. This subtle translation could be achieved, for example, by allowing the operator to easily shift the therapeutic elements a small distance distally and proximally, such as plus or minus up to 0.25 mm.

In another variation, the method may include enhancing the visualization of the treatment zone. The method may be to use energy delivery settings to ablate the tissue in a way that makes the ablated tissue appear differently on ultrasound. For example, it may be desirable to first ablate the tissue for approximately 5-15 seconds, followed by a short burst of higher power to then desiccate/char the tissue. The desiccated/charred tissue may be more echogenic, thus enhancing the visualization of the treatment zone. Additionally or alternatively, the method may also involve infusing air or other echogenic gas/material into a target zone to mark that area. This may be done after performing a treatment to mark the zone treated so that an overlapping treatment is not subsequently performed.

In another variation, the method may include affecting the target tissue in a fully non-invasive way. Here the method may include placement of an ultrasound imaging and/or therapeutic element onto the abdomen of a patient; operatively connecting the ultrasound imaging and/or therapeutic element to a console comprising a user interface, delivering ultrasound for imaging, targeting desired ovarian tissue, and delivering energy (e.g., partially-focused ultrasound, HIFU).

One aspect of the methods disclosed herein provides for pre-treatment planning prior to the manipulation of ovarian tissues. Fox-example, pre-treatment planning could be provided for the treatment of PCOS, including PCOS infertility. Here the method may include the step of performing non-invasive imaging to map the size, morphology and location of the ovary, the quantity and location of ovarian cysts, the location of ovarian cysts relative to other anatomical landmarks, and/or the volume of target tissue (e.g., stroma). Non-invasive imaging modalities may include magnetic resonance imaging (MRI), computed tomography (CT), transvaginal ultrasound, transabdominal ultrasound, or a combination thereof. The images and mapping performed may aid the care-giver in planning the therapeutic procedure and/or guide the care-giver while performing therapy. The mapping procedure may yield images, annotated images, and/or information related to the relationship between cysts or other target tissue and other anatomical landmarks.

Another aspect of the methods disclosed herein provides for harvesting available oocytes in conjunction with delivering therapy. In one variation, currently available tools and procedures may be used to first harvest available oocytes or tissue containing immature oocytes, which may then be stored for later use. For example, oocytes may be harvested using a transvaginal approach using transvaginal ultrasound and a needle. Alternatively, the therapy may be applied first. In yet another variation, the same tools utilized for providing the therapy may also be configured to also allow for oocyte harvesting. The therapy-providing tools may have improved features to aid in targeting, thus allowing for more oocytes to be harvested. These features may include methods for improved targeting, such as methods for steering, engaging the ovary and/or imaging.

II. Systems

Further described herein are embodiments of systems for manipulating ovarian tissues and/or heating PCOS, wherein one or more features from any of these embodiments may be combined with one or more features from one or more other embodiments to form a new embodiment within the scope of this disclosure. The systems may include an ovarian tissue apparatus configured for advancement through the vaginal wall (transvaginally), laparoscopically, percutaneously, via a natural orifice route through the vagina-uterus-fallopian tubes, or through an open surgical approach, and proximate an ovarian tissue; and an energy generator electrically coupled to the ovarian tissue apparatus, where the ovarian tissue apparatus typically comprises a docking device and one or more therapeutic elements, the docking device typically comprising an elongate body having a proximal end, a distal end, a lumen extending from the proximal end through the distal end, and a distal tip.

The ovarian tissue apparatus, docking device, therapeutic element, etc., may be made from polymeric materials (e.g., PEEK, polyester, AES, nylon), metals (e.g., stainless steel), metal alloys (e.g., platinum-iridium), and shape memory materials (e.g., nitinol, elgiloy) all of which are known in the art, and thus are not described in detail here. In some variations, the diameter of the elongate body of the docking device may range from about 3 Fr (1 mm) to about 15 Fr (5 mm). In other variations, the length of the elongate body of the docking device may range from about 15 cm to about 60 cm.

The docking device may be a relatively rigid member (e.g., needle, trocar) or flexible member (e.g., catheter, steerable catheter) with features configured to help with engagement of ovarian tissues. For example, the distal tip of the docking device may include one or more releasably securable attachment elements to aid in engaging the docking device to ovarian tissues. The releasably securable attachment elements may comprise one or more hooks, needles, or barbs. Alternatively or additionally, the docking device may be coupled to a vacuum source to enable vacuum-assisted engagement of the tip of the device to ovarian tissue. In some embodiments, the distal end of the docking device comprises a tissue engagement element. The tissue engagement element may have a preformed shape, e.g., a predetermined curvature.

In further variations, one or more therapeutic elements are delivered via the docking device. According to some embodiments, the therapeutic elements may be slidably disposed within the docking device. Here one or more ports may be disposed on the elongate body of the docking device through which the slidable therapeutic elements can be deployed into an ovarian tissue. Additionally or alternatively, the therapeutic element may comprise a lumen for delivering a thermal fluid, such as heated water or saline, or a biologic or pharmacological agent such as beta-blockers, anti-androgens (e.g., finasteride, flutamide, nilutamide, bicalutamide, spironolactone, cyproterone), follicular stimulating hormone, luteinizing hormone, other hormones, neurotoxins or tissue toxins (e.g., botox, guanethidine, ethanol), 5-alpha-reductase inhibitors (e.g., finasteride, dutasteride, izonsteride, turosteride, and epristeride), insulin modulating agents, or aromatase inhibitors (e.g., letrozole, exemestane, anastrozole), VEGF modulating agents, agents modulating inhibin, agents modulating interleukins, pluripotent or multipotent stem cell preparations, or cellular components. Furthermore, an agent (e.g., radiopaque material, echogenic material, etc.) may be left behind to tag the location(s) in which the therapeutic agent(s) are delivered. The one or more ports may also be disposed on the tissue engagement element. Additionally or alternatively, the one or more therapeutic elements may include an electrode, a cryoablation element, an ultrasound transducer, a laser, or a combination thereof. The therapeutic element, docking device, or separate device may also contain a lumen (or lumens) with suitable size to deliver a sufficient volume of fluid, such as saline or lactated ringers solution, to fill the abdominal cavity. This fluid could be used to help separate tissues (move non-ovarian tissues away from the ovary to reduce risk of injury when treating the ovary), improve ultrasonic visualization by surrounding tissues with fluid, shift tissues into new locations for improved visualization, provide cooling or other protection to the ovary or neighboring tissues while treating the ovary, or promote healing of the ovary after the procedure is completed. In some embodiments, the inner diameter of the docking device may range from 0.25 to 3.0 mm, from 0.25 to 2.5 mm, from 0.25 to 2.0 mm, from 0.25 to 1.5 mm, or from 0.25 to 1.0 mm to allow suitable flow rate while infusing or withdrawing fluid from the abdominal cavity. In other embodiments, the inner diameter of the docking device may range from 1.0 to 1.9 mm to allow suitable flow rate while infusing or withdrawing fluid from the abdominal cavity. In other variations, the docking device or therapeutic element could be used to aspirate fluid from within the ovary or retrieve sample fluid from the abdominal cavity to detect the presence of substances, such as blood, intestinal (e.g., fecal matter), or biomarkers, that provide information regarding the safety or success of the procedure.

According to some embodiments, the system may also comprise an energy generator so that energy can be delivered to ovarian tissue via the therapeutic elements. The energy generator may be configured to deliver one or more of the following: radiofrequency energy, direct heating, cryoablation, cooling, laser, microwave, unfocused ultrasound, partially-focused ultrasound, focused (HIFU) ultrasound, heated water/saline, or steam. In addition, the energy generator may be powered using a disposable battery, a re-chargeable battery, or via mains power.

Additionally or alternatively, the system may also comprise a mechanical drive system so that the therapeutic element rotates and/or translates in order to disrupt and/or remove target tissue. The mechanical drive system may incorporate a motor, a drive train, and means for operatively connecting to the therapeutic element. In some embodiments, only mechanical tissue manipulation may occur, but in others, mechanical manipulation may occur in series or in parallel with thermal energy as a means to cut and/or cauterize the tissue to minimize the risk of bleeding.

The system may further include a processor that has an algorithm operable to run a feedback control loop based on one or more measured system parameters, one or more measured tissue parameters, or a combination thereof. In any of the embodiments described herein, one or more sensors may be included in the system and may be used to measure the one or more system or tissue parameters. The sensors may be temperature sensors, impedance sensors, pressure sensors, or a combination thereof. The temperature sensor may be used to measure electrode temperature. The impedance sensor may be used to measure tissue impedance. When implemented, the feedback control loop may be configured to modify a parameter of energy delivery based on the measured one or more system or tissue parameters. For example, the parameter of energy delivery (or energy removal in the case of cooling/cryotherapy) that may be modified is duration of energy delivery, power, voltage, current, intensity, frequency, pulse, pulse width (e.g., duty cycle), temperature, type of energy delivery, flow rate, pressure, or a combination thereof.

Any of the systems disclosed herein may further comprise a user interface configured to allow user defined inputs. The user-defined inputs may include duration of energy delivery, power, target temperature, mode of operation, or a combination thereof. The mode of operation may be a coagulation mode, a heating mode, a cooling mode, a cryoablation mode, an ablation mode, a desiccate/char mode, an irrigation mode, an aspiration mode, mechanical disruption mode, tissue removal mode, or a combination thereof. Any of the systems disclosed herein may further comprise an automated treatment delivery algorithm that could dynamically respond and adjust and/or terminate treatment in response to inputs such as temperature, impedance, treatment duration, treatment power and/or system status.

According to embodiments described herein, which may partially or as a whole combine with other embodiments, the system and method may include a transvaginal ultrasound probe for placement in the vagina to aid with visualization of tissue and/or navigation of system components. A docking/guiding device (e.g., a docking catheter) may be coupled to the ultrasound probe and advanced through the wall of the vagina directly into the peritoneal space to engage the surface of the ovary (e.g., the medial aspect of the ovary), or be advanced into the ovary, under ultrasound guidance. Via this docking catheter, a treatment device could be deployed such that one or more radiofrequency energy treatment elements, e.g. electrodes, are delivered within the ovary through a single entry point on the surface of the ovary. Following delivery of the treatments, aspiration could be applied at the aperture created in the ovary. Aspiration could also be achieved via holes or slots in or near an electrode that are connected to a lumen in the docking catheter. In an alternative embodiment, aspiration may be applied prior to and/or during delivery the treatments.

Figure 2:
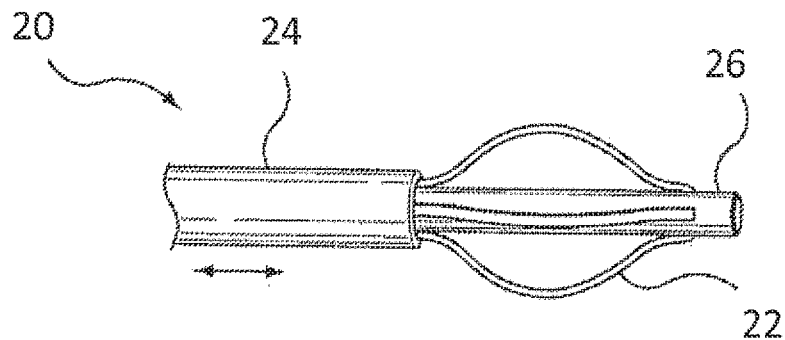
FIGS. 2-5 depict embodiments of devices for creating space in the area adjacent to the ovary for facilitating a procedure on the ovaries.

In some embodiments, e.g., prior to or after docking on/engaging the ovary, the system may include a spacing device that includes an expandable structure, or that is configured to infuse fluid for creating space around the ovarian tissues or for separating ovarian tissues. For example, the spacing device may contain scaffolding, one or more balloons, or at least one port for delivering fluid or gas into the space adjacent to the ovary, the purpose of which would be to aid in the separation of tissues such that the desired portion of the ovary could more optimally be accessed and such that therapeutic elements could be delivered in a way to minimize disruption of non-ovarian tissues. Referring to FIG. 2, in one embodiment the spacing device (20) may include scaffolding having an expanded configuration (22) and a collapsed configuration (not shown). Here the expanded configuration (22) is effected by movement of an outer shaft (24) relative to an inner shaft (26). Upon motion of the outer shaft (24) relative to the inner shaft (26), the scaffolding is able to transition from its collapsed configuration to its expanded configuration (22). Other expandable scaffolds may be constructed from self-expanding materials that are constrained for delivery then expanded via removing the constraint. The scaffold may be made from a polymer, metal, metal alloy, or combinations thereof. The scaffold may also comprise one or more wires, braid, a laser cut tube, or a slotted tube.

Figure 3:
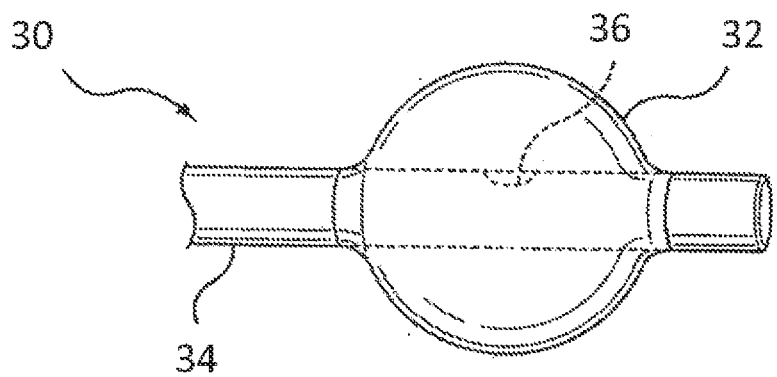

In the embodiment shown in FIG. 3, the spacing device (30) comprises a balloon (32) that is concentrically disposed about a shaft (34). The balloon (32) is inflated via fluid (e.g., a liquid or a gas) flowing through an infusion port (36) in the shaft (34).

Figure 4:
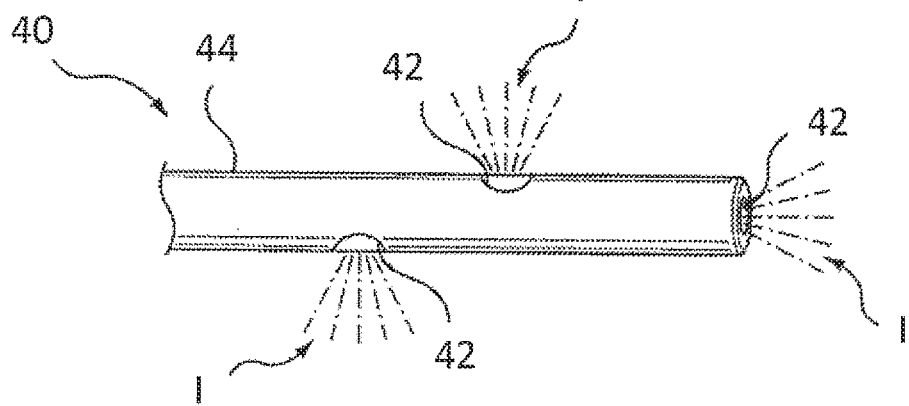

In another embodiment, as shown in FIG. 4, the spacing device (40) includes a plurality of infusion ports (42) that may be located at the distal end/or in one or more locations along the length of the shaft (44) for the delivery of infusate (I) to create space around target ovarian tissues or to separate ovarian tissues. In some variations, the spacing devices may be used to displace non-target tissues (e.g., bowel) during advancement of system components, e.g., docking devices, from the vagina to the ovary.

Figure 5:
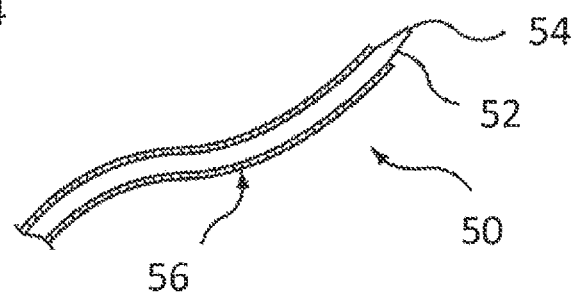

Furthermore, FIG. 5 shows an embodiment of an atraumatic or flexible sheath-like device (50) that may be delivered and potentially guided via a blunt dissection element (52) and guidewire (54) or steering mechanism (not shown) through the vaginal wall and proximate to the ovary. Once positioned, the optional blunt dissection element (52) and/or guidewire (54) may be removed and the guiding/docking device and or therapeutic element(s) may be delivered through the lumen of the outer sheath (56). The outer sheath (56) may serve as the guiding/docking device with optional aspiration used to engage the ovary or infusion to create additional space as described in association with FIG. 4. In some instances, the guidewire (54) may be sharpened and used to penetrate the ovary once the dissection element (52) is positioned proximate the ovary. In this configuration, the guidewire (54) may be positioned at a target location within the ovary. Once positioned, the dissection element (52) may be removed and replaced with therapeutic element(s) in an over-the-wire approach. The guidewire (54) may optionally be removed prior to applying therapy.

As previously stated, the guiding/docking device may be one component of the systems described herein, and could be utilized to facilitate access to tire ovaries from the selected approach. The guiding/docking device may have a preset shape that facilitates navigation to the ovary and it could be torqueable. Additionally or alternatively, it could have a steerable tip that could be actuated by the handle. The guiding/docking device and the therapeutic device could also be combined into a single device, e.g., an ovarian tissue apparatus. The docking device generally comprises an elongate body (e.g., a needle, trocar or catheter) having a proximal end, a distal end, a lumen extending from, the proximal end through the distal end, and a distal tip. This lumen may be used to deliver fluid and/or to aspirate.

Figure 6:
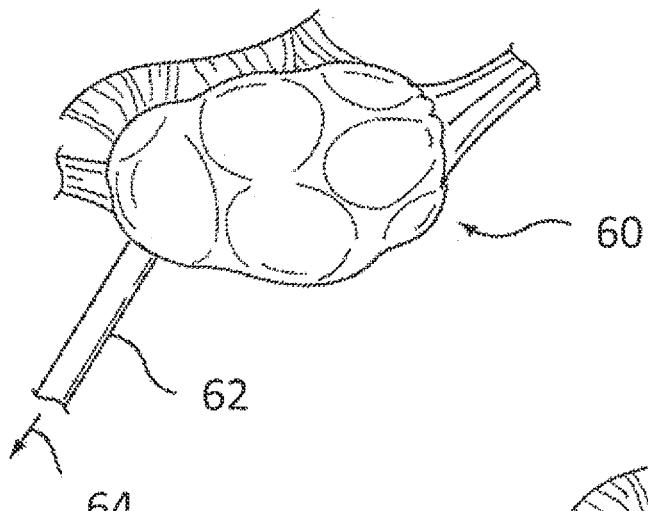
FIGS. 6-10 and 11A-11B depict embodiments of guide/docking device and associated methods for facilitating access to the ovaries.
Figure 7:
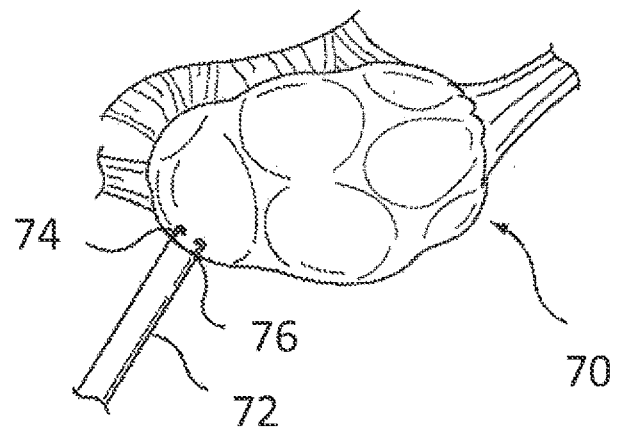
Figure 8:
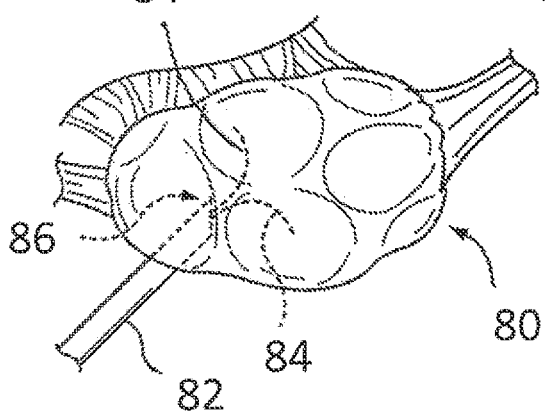

Docking to the ovary can be accomplished using various techniques. Referring to FIG. 6, docking to the ovary (60) can be accomplished by a docking device (62) that applies vacuum (64) through a lumen of the docking device (62). Alternatively, as shown in FIG. 7, docking to the outside of the ovary (70) may be accomplished by a docking device (72) via a concave surface or surface that was mildly abrasive on the docking device (not shown), or via one or more hooks (74) at the distal end (76) of the docking device (72) that are configured to secure to a desired section of the ovary (70). Instead of docking to the outside surface of the ovary, docking within the tissue of the ovary (80) can also be performed, as shown in FIG. 8. Here docking may be accomplished using a docking device (82) having one or more needles or wires (84) that are deployable through the distal end (86) of the docking device (82), and which are configured to anchor within the tissue of the ovary (80). The needles, wires, or hooks may also be configured to deliver therapy (e.g., they may be wire electrodes or may further incorporate electrodes for delivering energy and/or may have mechanical motion applied to mechanically disrupt tissue). In some instances, it may be useful to secure the ovary in a manner that allows for repositioning for further treatments. Anchoring either the docking device and/or the therapeutic element in the target tissue may help the user to move the ovary relative to surrounding non-ovary tissues to improve and/or confirm visualization. Moving the ovary may also allow the user to more easily reposition the device for subsequent treatments.

Figure 10:
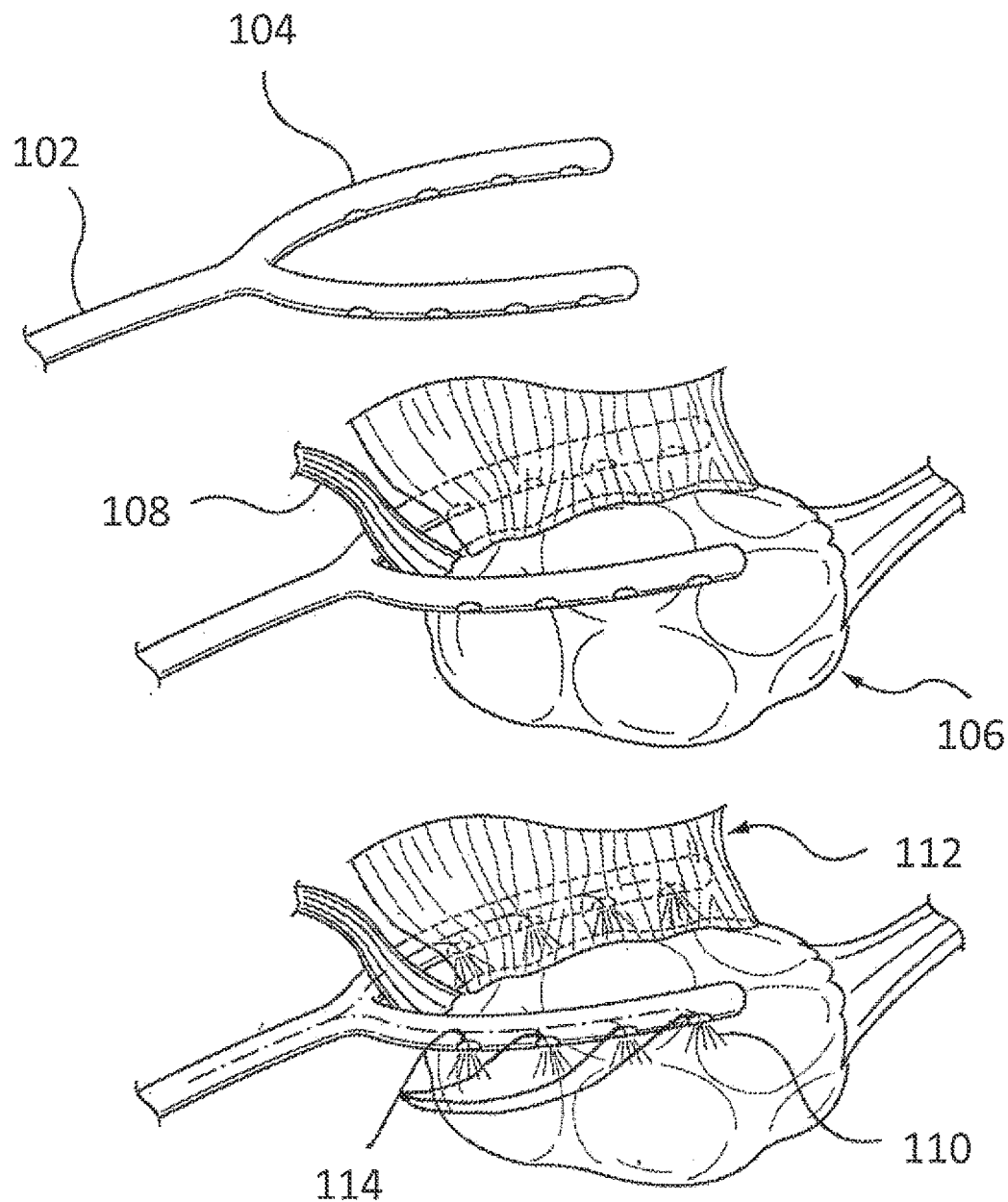

Docking could further be accomplished using a docking device having a preset shape that is configured to fit the shape of the ovary at a specific location. In this variation, the docking device could be configured to engage ovaries having a size ranging from about 3 to 7 cm in length, about 1 to 4 cm in width, and about 0.5 to 4 cm in thickness. For example, as shown in FIG. 10, docking device (102) has a shaped portion (104) at its distal end that is shaped to fit the junction of the ovary (106) and the broad ligament (108) (e.g., near the mesovarium), and which could allow therapeutic elements (110) disposed therein to be advanced/delivered into the ovary adjacent to the mesovarium (112). The multiple therapeutic elements (110) may be curved, but their structure is not so limited, and any suitable configuration may be employed, In one exemplary embodiment, the docking device may comprise a cup configured to engage at least a portion of the outer surface of an ovary. Here the cup may comprise a proximal end configured for communication with a vacuum source and a distal end for securing the ovary. The distal end of the cup can have an arcuate or annular surface configured to match the contours of the outer surface of the ovary. The distal end can also be sized to match the dimensions of a human ovary, wherein the distal end has a diameter of about 0.5 to 7.0 cm, about 0.5 to 6.0 cm, about 0.5 to 5.0 cm, about 0.5 to 4.0 cm, about 0.5 to 3.0 cm, about 0.5 to 2.0 cm, or about 0.5 to 1.0 cm. Additionally, the cup may comprise a conical geometry for accommodating a variety of ovary sizes.

Figure 9:
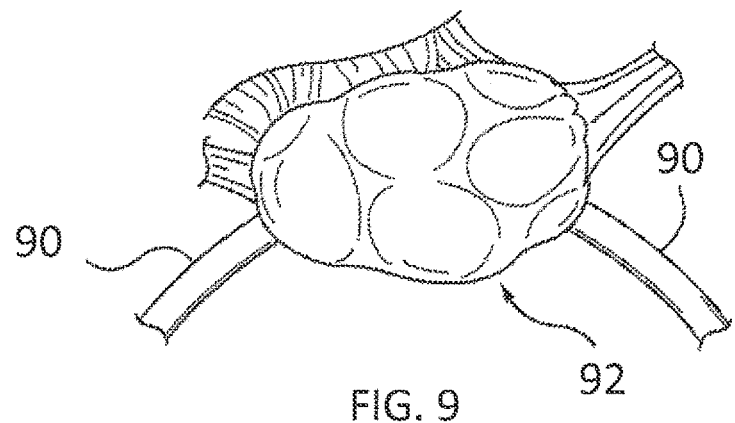

Further embodiments of the docking mechanism may include securing the ovary at more than one point with a docking device. With such a device (90) as shown in FIG. 9, docking could occur at opposite sides of the ovary (92), which could facilitate delivery of therapy across the entire ovary or between multiple points on and/or within the ovary in a way that either mechanically penetrates or does not mechanically penetrate the outer surface of the ovary. A docking/guiding device (90) that grasps at two or more places on the ovary (92) may have the ability to be actuated or adjusted to widen or narrow the amount of ovarian tissue captured between its contact points. Alternatively, therapeutic elements may be delivered through the docking devices (90) and into the ovary (92), facilitating independent control of positioning the therapeutic elements.

Figure 11A:
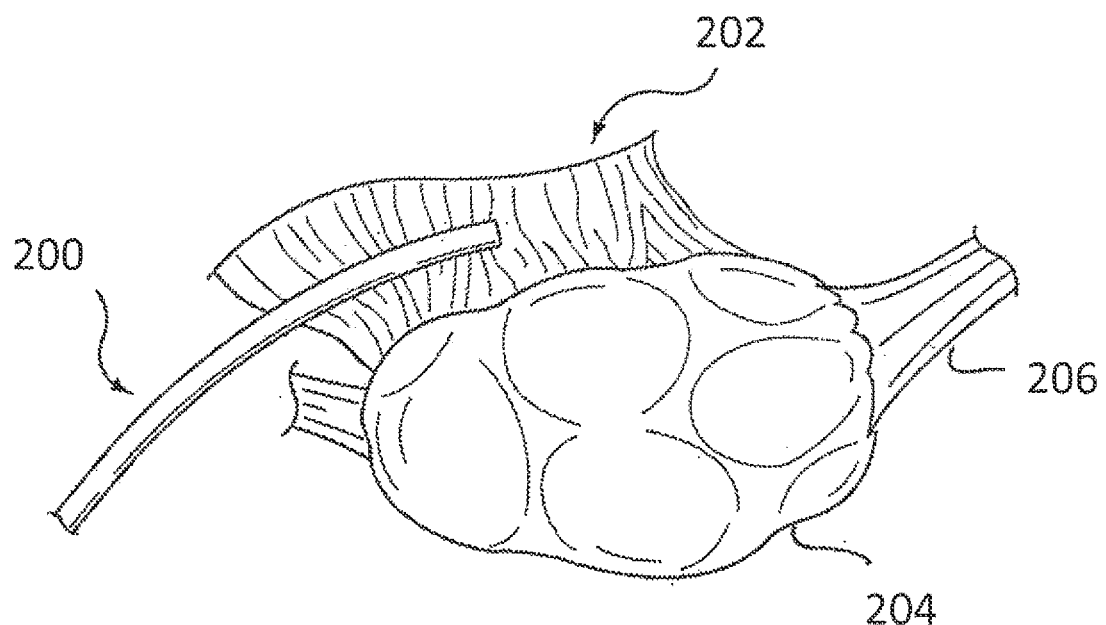
Figure 11B:
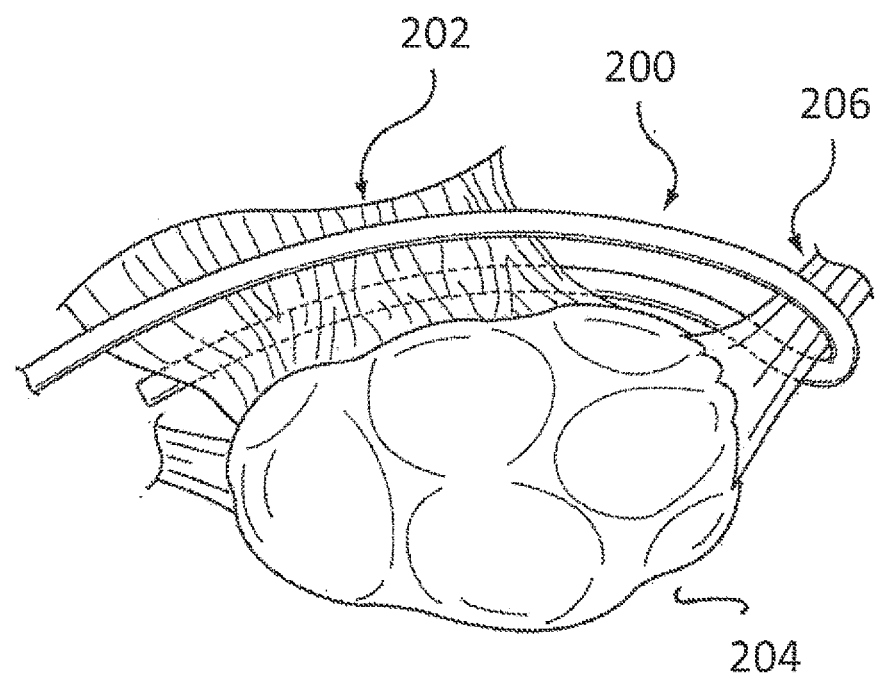

FIGS. 11A and 11B depict yet further variations where the docking/guiding device (200) could be used to target and/or capture the mesovarium (202) (e.g., by looping around the mesovarium as shown in FIG. 11B) to deliver therapy to the mesovarium (202) and/or the suspensory ligament (206) or ovarian ligaments. In this configuration, therapy may be delivered via electrodes incorporated into the docking/guiding device (200), or via a separate element.

The therapeutic elements may have any suitable configuration, e.g., they may have any suitable length, diameter, flexibility, geometry, shape memory, etc. suitable for the ovarian tissue procedures described herein. In some variations, the therapeutic elements include one or more curved structures that comprise one more electrodes. A therapeutic element such as those depicted in FIG. 12A-12F comprising one or more curved structures with electrodes may be useful for a variety of reasons. The curved structure may aid in anchoring the device in the target tissue, limiting the risk of the device moving during treatment due to patient movement or user error. The curved structure may also be configured to match the contour of the ovary, allowing for improved positioning within a variety of sized or shaped ovaries. Additionally or alternatively, the curved structure may allow for longer or additional electrodes to be delivered and used simultaneously, allowing for larger ablation volumes per energy application. This feature may limit pain experienced by the patient and reduce procedure time. The curved structures may have a straightened length and an unconstrained radius of curvature. The straightened length may range from about 5.0 to about 40 mm, from about 5.0 to about 35 mm, from about 5 0 to about 30 mm, from about 5.0 to about 25 mm, from about 5.0 to about 20 mm, from about 5.0 to about 15 mm, or from about 5.0 to about 10 mm. The unconstrained radius of curvature may range from about 3.0 to about 10 mm, from about 3.0 to about 9.0 mm, from about 3.0 mm to about 8.0 mm, from about 3.0 mm to about 7.0 mm, from about 3.0 mm to about 6.0 mm, from about 3.0 mm to about 5.0 mm, or from about 3.0 mm to about 4.0 mm. In some embodiments, the unconstrained radius of curvature ranges from about 4.0 mm to about 6.0 mm.

Figure 12E:
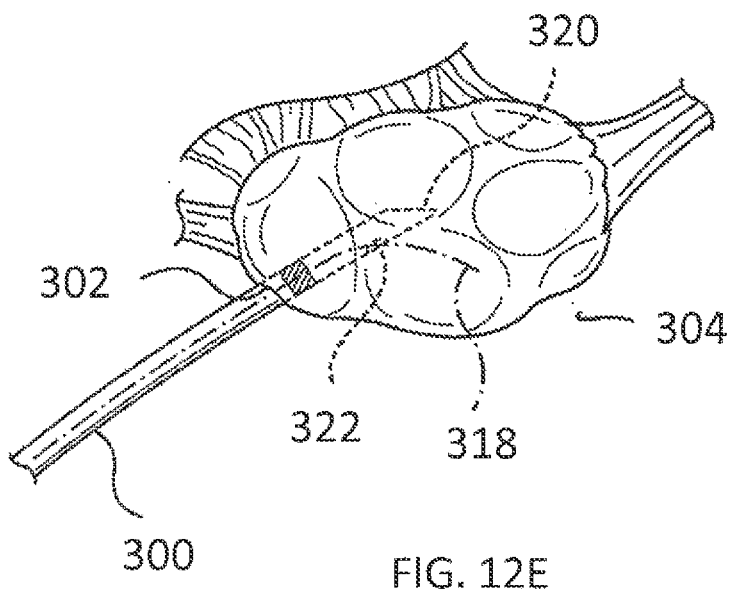

The therapeutic elements may be advanced into the ovary in various ways. For example, and as shown in FIGS. 12A-12E, upon advancement of the docking device (300) through the capsule (316) of the ovary (304), the therapeutic element(s) (306) are advanced from inside the ovary (304) to a target location(s) within the ovary (304). The therapeutic elements may be curved (FIG. 12A, 306) or straight (FIG. 12B, 308), or they may take a spiral or helical configuration (FIG. 12C, 310) or a random configuration (not shown) when deployed, e.g., within an ovarian cyst (312). Alternatively, and as shown in FIG. 12D, the therapeutic element (314) may be configured to track about at least a portion of the perimeter of the ovary (304) such that therapy targets tissue proximate the cortex or follicles of the ovary (304). Alternatively, the therapeutic element may be configured to track about at least a portion of the ovary at or near the junction of the stoma and cortex such that therapy may target tissue proximate to this junction. The therapeutic elements may be provided as a feature of the guiding/docking device. They may also be provided as elements that can be deployed from a lumen within the guiding/docking device or sheath-like device, as shown in FIG. 5. The therapeutic elements (306) may be shaped such that they releasably secure the device within the tissue when deployed, as shown in FIG. 12A.

The one or more therapeutic elements (306, 308, 310, 314) may be advanced from the docking device (300) into the ovary (304) one or multiple times and deployed within the ovary proximate to or within ovarian cysts or other target tissue. One benefit of this method may be that multiple therapies (e.g., multiple sequential therapies where a single therapeutic element is repositioned, or sequential/simultaneous deployment of multiple therapeutic elements) could be delivered through a single entry/access point (302) on the surface of the ovary, which may minimize the risk of adhesions.

FIG. 12E depicts a variation where the docking/guiding device (300) is used to penetrate into the ovary (304) and permit delivery of one or multiple therapeutic elements (318) out of the distal tip (320) or through one or more side ports (322). The docking/guiding device (300) may comprise, for example, a 14 to 18 gauge needle approximately 20 to 45 cm long, and the therapeutic element (318) may comprise, for example, one or more 0.020 cm to 0.076 cm diameter metal wire(s) that exit the side port (322), as shown, or the distal tip (320). However, the diameter of the metal wire may be as large as 0.140 cm. In some cases, the wire may simply be a straight wire, but in other variations, the distal portion of the therapeutic element (318) may be processed to have a pre-set shape (e.g., a curve), as shown in FIG. 12E. The therapeutic element may be insulated along the majority of its length to electrically isolate it from the docking device (e.g., via a polyimide sleeve, PET heat shrink), if it is constructed of metal. As such, only the distal portion of the wire(s) that extend beyond the distal end or side port would be electrically connected to the energy generator. When two wires are employed, they may be deployed in a geometry similar to that shown in FIG. 12A with a distance between the tips of the wires ranging from approximately 3 to 20 mm apart. However, in other instances the distance between the tips of the wires may range from about 7.0 to 10 mm apart, or up to about 15 mm apart.

Figure 12F:
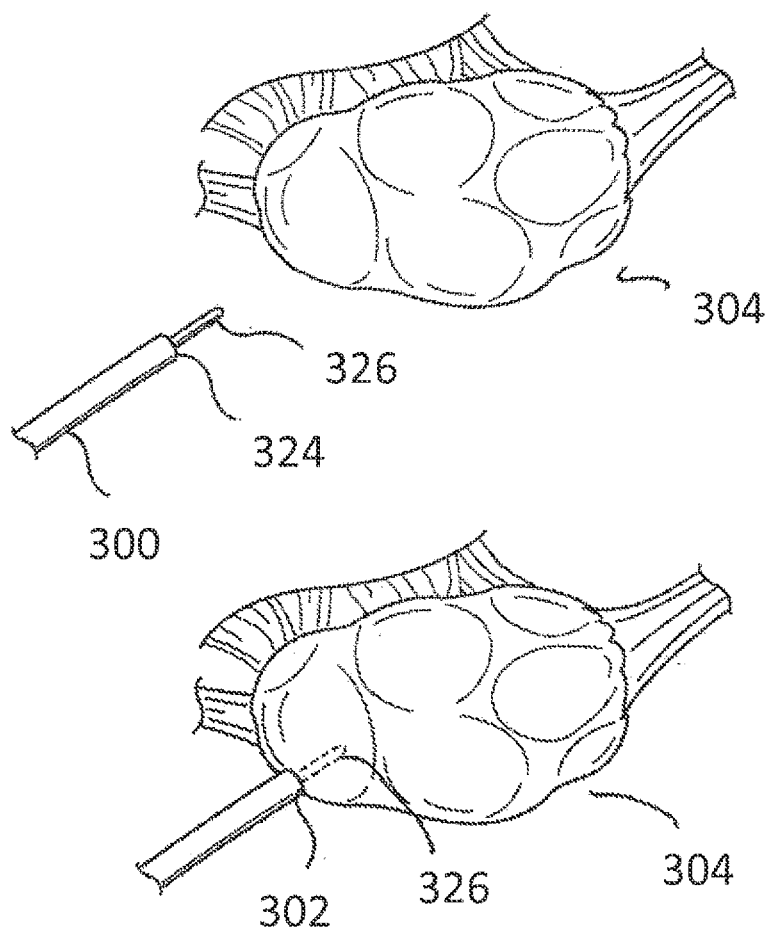

The docking/guiding device may also be configured to rest on the outer surface of the ovary (i.e., the distal tip of the docking device is not inserted into the ovary). For example, as illustrated in FIG. 12F, the docking device (300) may include a wider element or shelf (324) proximal to the therapeutic element (326) to act as a backstop and prevent it from penetrating deeper into the ovary than a preset distance. For example, the shelf may have a diameter greater than or equal to about 20% larger than the diameter of the element to be inserted into the ovary.

Referring back to FIG. 10, the side holes (114) of the guiding/docking device (102) could alternatively be used to facilitate delivery of the therapeutic elements (110) in a pre-specified consistent pattern of multiple entry points of the ovary. This could be done to allow consistent targeting of a preferential portion of the ovarian tissue or to deliver a preferential pattern of therapies.

The system may also provide features that are configured to rotate the one or more therapeutic elements during application of energy to facilitate driving the therapeutic elements through the tissue (e.g., cutting, removing, or ablating a volume of tissue), resulting in a larger treatment zone.

The total affected volume of tissue within a given ovary may range from about 240 $mm^3$ to about 3000 $mm^3$, with a single ablation volume ranging from about 30 $mm^3$ to about 3000 $mm^3$, In some instances, about 3% to about 20% of the ovarian volume is affected, e.g., by ablation. The system may be configured such that ablations do not extend beyond a certain distance from any edge of the electrode(s), e.g., 5 mm. The system may be further configured such that the ablations are non-spherical in shape, e.g., the in-plane longest dimension is greater than 2 times the perpendicular depth. The system may be further configured such that ablations can be delivered within the ovary in a way that spares tissue within 2 mm of the outer surface (capsule) of the ovary.

Referring to the exemplary stepwise illustration in FIGS. 13A to 13D, a guiding/docking device (400) is advanced into the ovary (402) and curvilinear therapeutic elements (404) deployed from a location inside the ovary to a target area(s) (FIGS. 13A and 13B). The curvilinear therapeutic elements (404) are then rotated in the direction of the arrow shown in FIG. 13C to affect, e.g., ablate, a volume of tissue (FIG. 13D, 406). A variety of the therapeutic elements described herein may be rotated and/or translated during the application of energy to reduce force required to traverse through tissue, cut, coagulate, desiccate/char, reduce treatment time and/or create a larger treatment zone. These techniques may be employed with other therapeutic elements as described herein and are not limited to those shown in FIGS. 13A to 13C.

The system may also provide features that are configured to move the therapeutic elements within a single 2-dimensional plane through the tissue during application of energy to facilitate driving the therapeutic elements through the tissue (e.g., cutting), resulting in a larger treatment zone, which is depicted in the stepwise illustration of FIGS. 14A to 14E. Referring to FIGS. 14A to 14E, a guiding/docking device (500) is advanced into the ovary (502) and curvilinear therapeutic elements (504) deployed from a location inside the ovary to a target area(s) (FIGS. 14A and 14B). The curvilinear therapeutic elements (504) are then actuated in the direction of the arrows to change from an open configuration (FIG. 14C) to a closed configuration (FIG. 14D) to affect, e.g., ablate, a volume of tissue (FIG. 14E, 506). Although curved therapeutic elements are depicted, therapeutic elements comprising any suitable geometry, e.g., straight therapeutic elements, may be employed. Further, it is understood that any suitable therapeutic element described herein may be translated in a 2-dimensional plane of tissue during the application of energy to reduce force required to traverse through tissue, cut, coagulate, desiccate/char, reduce treatment time and/or create a larger treatment zone.

Figure 15A:
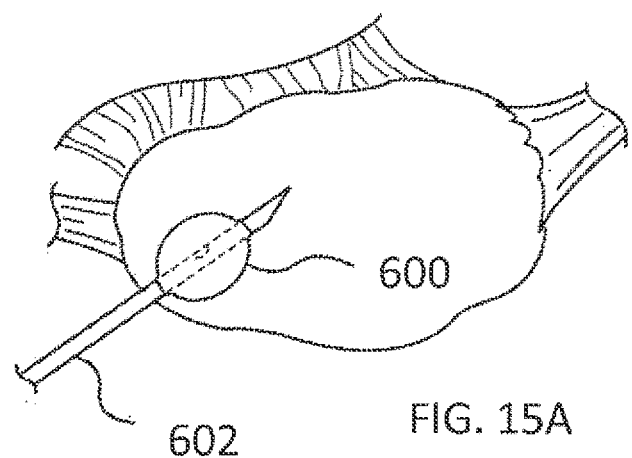

According to embodiments described herein, which may partially or as a whole combine with other embodiments, the therapeutic element may also comprise an expandable balloon that may be used to anchor the device within the tissue, mechanically disrupt tissue and/or deliver thermal energy (e.g., RF, microwave, ultrasound, direct heat) or cooling (e.g., cold saline, cryo). In one variation, as shown in FIG. 15A, a balloon (600) is mounted on the guiding/docking device (602). In another variation, as provided in FIG. 15B, the balloon (600) is delivered through the guiding/docking device (600) by pushing it out. In a further variation, the guiding/docking device may be advanced through the ovarian tissue to create a channel into which the balloon is delivered as the guiding/docking device is subsequently retracted. One or more electrodes, antennae, or ultrasound transducers may be positioned within the balloon or on the balloon surface to induce heating of tissue directly and/or indirectly. Alternatively, a cold or cryogenic material may be delivered and removed/outgassed via lumen(s) within the guiding/docking device to induce cooling or freezing of tissue.

FIG. 31 depicts another embodiment of a docking/guiding device having a single therapeutic element. Here the docking/guiding device (301) may comprise, for example, a 14 to 18 gauge needle approximately 20 to 45 cm long, and the therapeutic element (305) may comprise, for example, a curved shaft having a diameter of about 0.05 cm to about 0.13 cm and two electrodes disposed thereon, as shown. The shaft may have a pre-set shape (e.g., a curve with radius 0.38 cm to 1.6 cm). The therapeutic element may be insulated along the majority of its length to electrically isolate it from the docking device (e.g., via a polyimide sleeve, PET heat shrink, Parylene, nylon, Pebax), if it is constructed of metal. As such, the uninsulated portions would be electrically connected to the energy generator. In another variation, therapeutic element may be comprised of a non-electrically conductive shaft with one or more electrically conductive elements, e.g., electrodes. As previously described, the electrodes may wrap around the entire circumference of the shaft or may only cover a portion of the shaft circumference, in which case the electrodes may or may not be angularly offset from one another. The electrodes could be electrically isolated from each other and deliver energy in a monopolar or bipolar fashion. In a bipolar configuration, one electrode would serve as the active electrode and the other electrode would serve as the return electrode. In another variation, both electrodes could delivery energy and the energy would return to a neutral electrode located elsewhere, such as on the skin of the patient, on the docking/guiding device, or on the ultrasound probe. The electrodes could also be electrically connected to each other and deliver energy where the return or neutral electrode (not shown) is located elsewhere, such as on the skin of the patient, on the docking/guiding device, or on the ultrasound probe. The electrodes may have a length of about 0.10 cm to about 2.5 cm; a diameter of about 0.05 to about 0.4 cm, about 0.05 to about 0.3 cm, about 0.05 to about 0.2 cm, about 0.05 to about 0.1 cm, about 0.2 to 0.4 cm, or about 0.076 cm to 0.14 cm; and spacing of 0.050 cm to 0.64 cm.

Figure 15B:
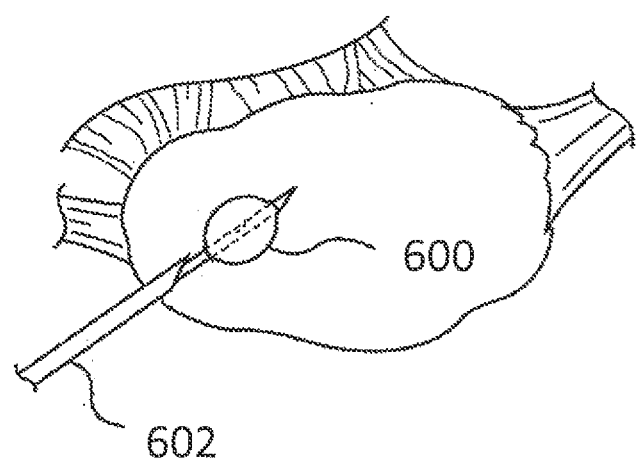
Figure 16A:
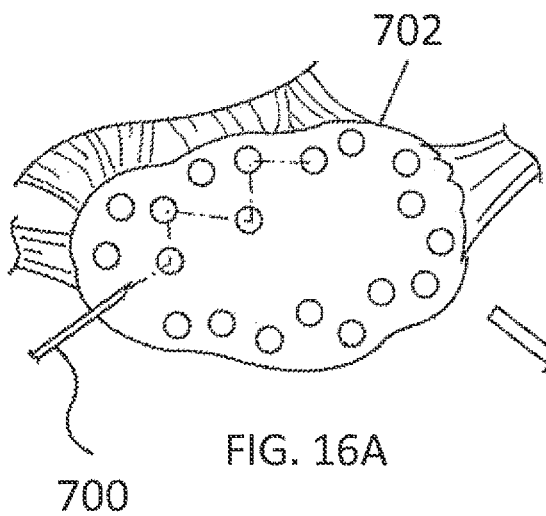
Figure 16B:
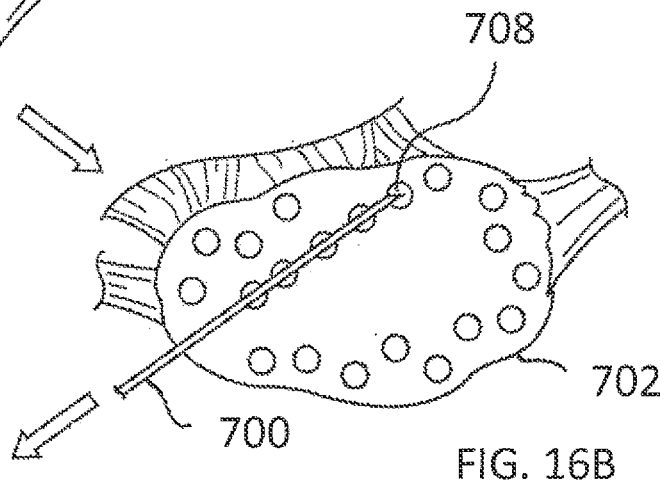
Figure 16C:
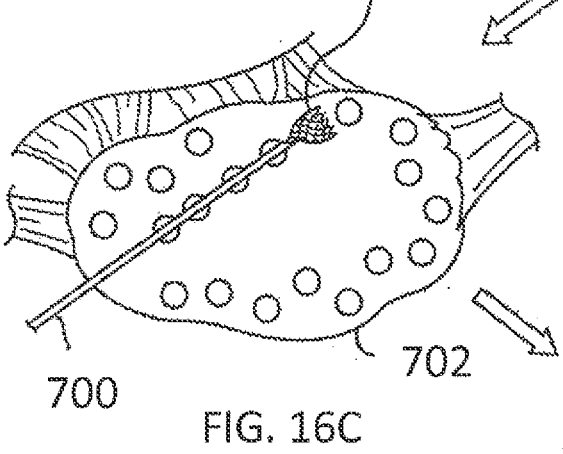
Figure 16D:
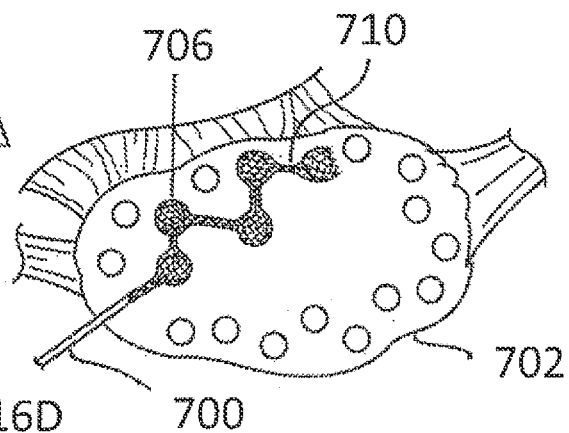
Figure 17:
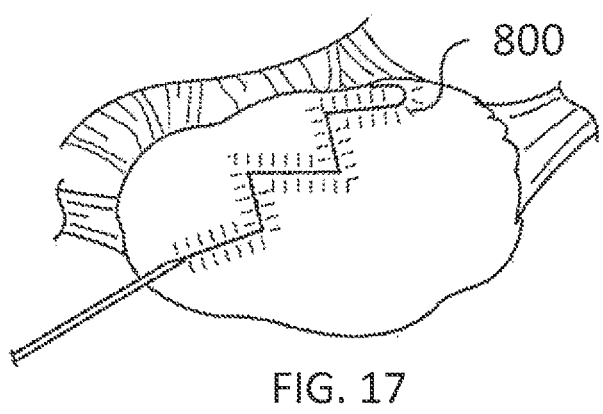
Figure 18:
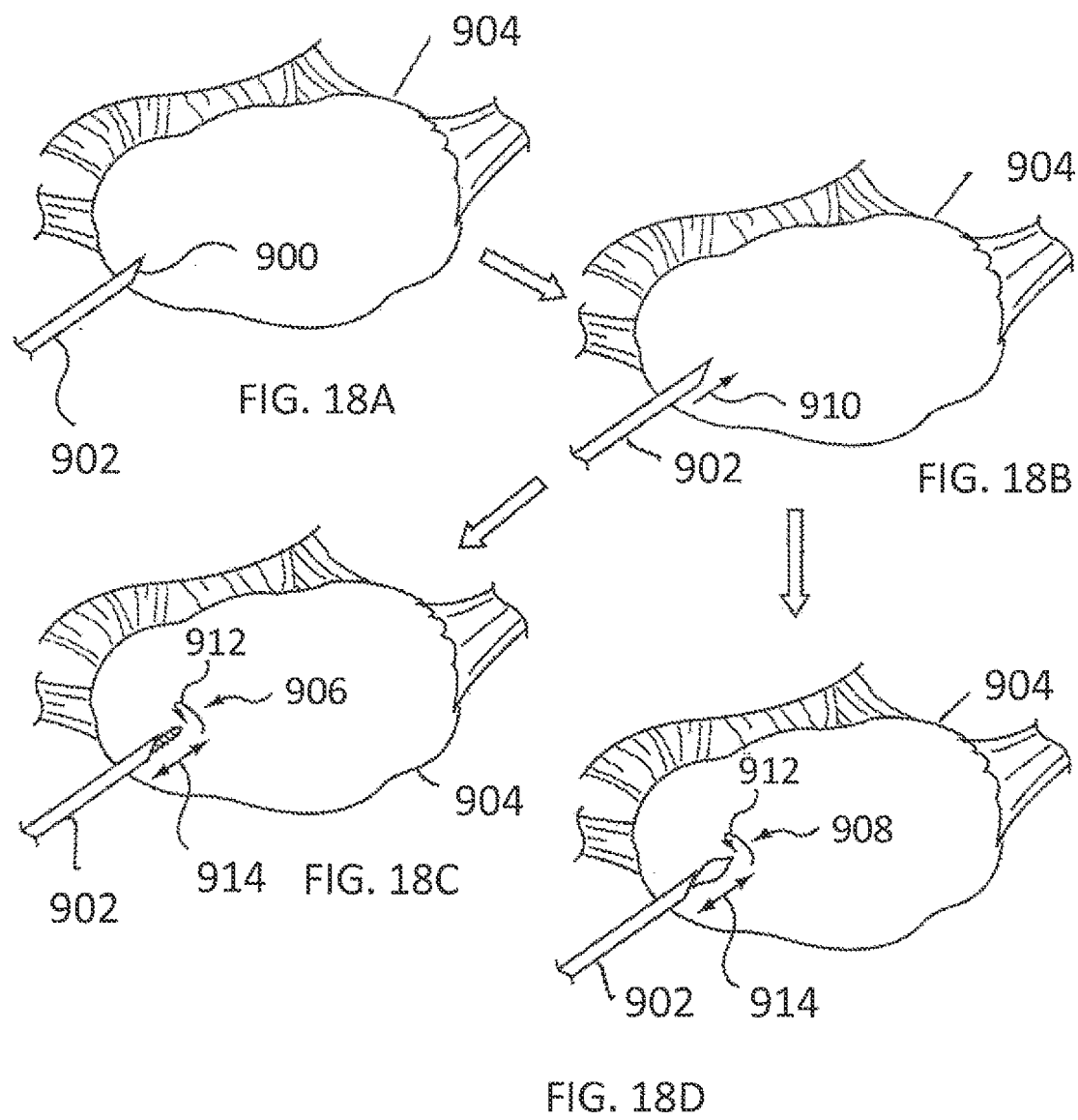

Other systems and methods may be employed for treating polycystic ovary syndrome, as illustrated in FIGS. 16A to 16D. For example, the guide/docking device (700) may be advanced thorough the ovary (702) in either a straight path (FIG. 16B) or in a meandering/directed path (FIG. 16A). This could be done under imaging to ensure that the guiding/docking device (700) was placed in a desirable location throughout the delivery. The therapeutic element (706) could then be delivered through a lumen on the guiding/docking device (700) and into a cyst (708) and/or channel (710) created by the guiding/docking device as it was retracted. Aspiration could be performed by the guiding/docking device (700) as it is being delivered or retracted. Alternatively, aspiration could also be performed through the therapeutic element (706). Alternatively, no aspiration could be performed. Once fully deployed, the position of the entire therapeutic element (706) can be confirmed in real-time using 2D or 3D imaging (e.g., transvaginal ultrasound), allowing for all planned treated areas to be assessed/confirmed prior to application of energy. If desired, the therapeutic element may be recaptured and re-deployed to optimize position. Then, energy may be applied via the therapeutic element, which is electrically coupled to an energy generator. Optionally, the guide/docking device (700) and therapeutic element (706) can be retracted to the next desired treatment location, and energy applied. This optional step may be repeated until all desired treatments are performed, resulting in a treated section. Alternatively, and as shown in FIG. 16D, a longer portion of the therapeutic element (706) can be exposed to multiple regions of the ovary by an extended retraction of the guiding/docking device (700). The treated section may be created by a single application of energy over the length of the therapeutic element, multiple applications of energy over portions of the therapeutic element, or by continuously applying energy while simultaneously retracting the guide/docking device (700) and/or therapeutic element (706). The exemplary therapeutic element (706) used in this instance could be an expandable mesh. FIG. 17 depicts an alternative therapeutic element comprised of a flexible wire, cable, or coil (800). The expandable mesh material may enhance or maximize contact with tissue, especially within a cyst. Another example of a therapeutic element that could be used in this setting is a balloon (e.g., as shown in FIGS. 15A and 15B). Any of the other therapeutic elements disclosed herein may also be utilized to administer treatment via this method. The therapeutic element may also have an atraumatic tip.

In the case of mechanical disruption, the therapeutic element may comprise a rotating or translating element capable of mechanically manipulating (e.g., destroying, stimulating) target tissue, as illustrated in FIG. 18A to 18D. Here the tip (900) of a guiding/docking device (902) may be used to facilitate access into the ovary (904). Once positioned in a desired location within the ovary (904), a mechanical disruption element (906, 908) may be advanced in the direction of arrow (910) into the tissue. Once deployed, the mechanical disruption elements (906, 908) may be rotated in the direction of arrows (912) and/or translated in the direction of arrows (914) to disrupt tissue. Motion of the therapeutic element may be performed manually via a handle at the proximal end of the device or via a motor and/or drive train (battery or mains powered). Mechanical disruption elements may take (he form of a solid screw-like component (906), an expandable wireform component (908), or other geometry that facilitates desired tissue disruption. The expandable wireform component (908) may be comprised of a self-expanding material (e.g., spring steel, nitinol, elgiloy) that expands as tissue is morcellated. The therapeutic element may also incorporate one or more electrodes used to delivery energy to heat target tissue, ablate target tissue, cauterize blood vessels, and/or cut tissue. The morcellated tissue may be retrieved in some instances if it can be used for diagnosis, or if it contains either oocytes or cellular components that may be useful in further care. Electrodes may be either separate elements mounted on the therapeutic element or the therapeutic element itself.

Figure 19:
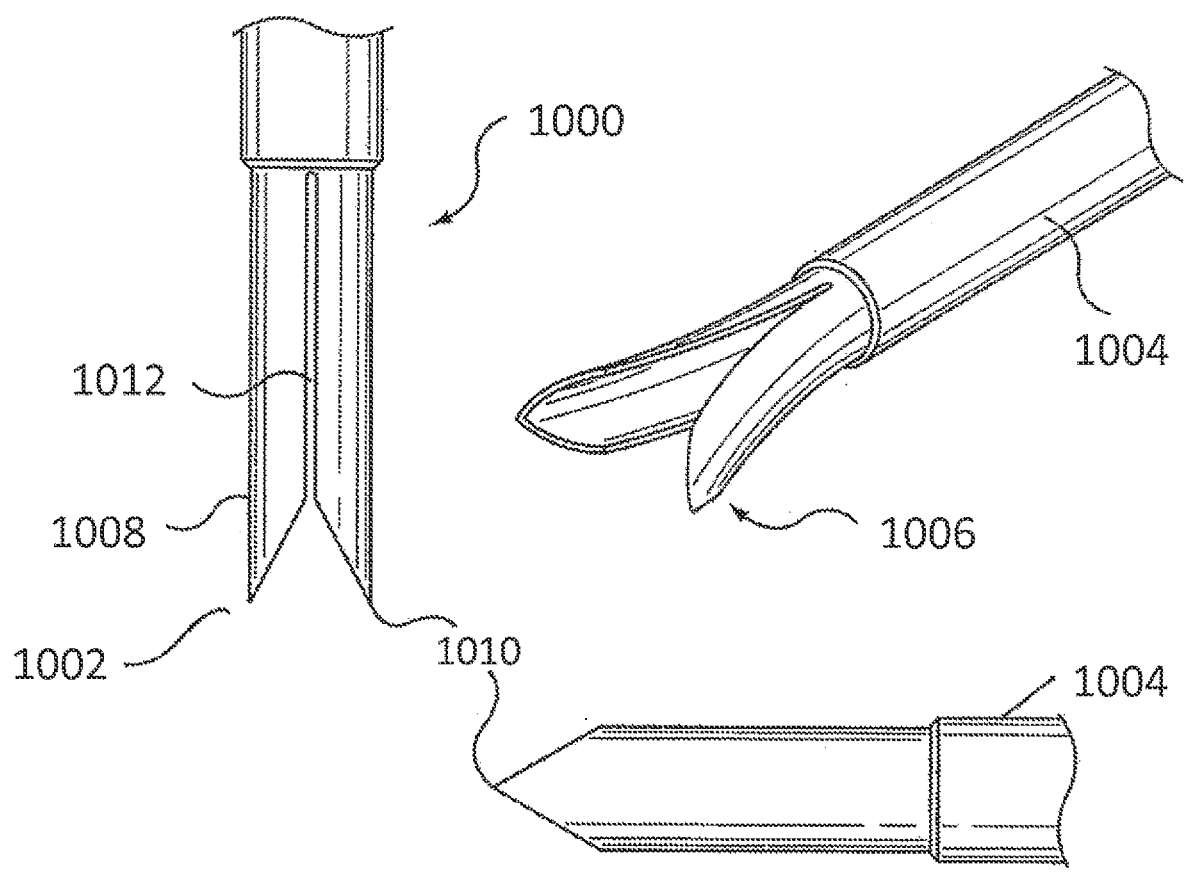

The therapeutic element(s) may be constructed from a variety of materials and in a variety of geometries. In its simplest form, the therapeutic element may be comprised of round wire. Alternatively, as shown in FIG. 19, the therapeutic element (1000) may be disposed at the distal end (1002) of a guiding/docking device in a manner such that it is capable of expanding upon deployment. In some embodiments, the therapeutic element (1000) may be constructed of a metal tube or wire (e.g., nitinol, elgiloy, spring steel) with characteristics that allow for it to be shaped into an expanded configuration (1006) and a collapsed configuration (1008), and to form a sharp end (1010). The metal tube or wire may be laser cut or otherwise processed to split the tube or wire in half along a defined length (1012), which may, for example, range from about 1-3 cm. The metal tube or wire may further be cut, ground or otherwise processed to form a sharp end (1010). Once cut, the two (as shown) or more therapeutic elements may be shape set or formed into an expanded configuration (1006). When constrained by a sheath (1004), the distal end is collapsed, and an exposed portion of the sharp end (1010) used to penetrate the tissue and position the device. Once in position, the therapeutic element (1000) may be advanced out of the sheath and expanded into the tissue. Alternatively, the outer sheath (1004) may be retracted to allow the therapeutic element (1000) to become exposed. In some instances, additional manipulation and/or application of energy may be required to facilitate expansion of the therapeutic element. Energy may simultaneously or sequentially be applied to affect the target tissue. These techniques may also be employed with the variety of therapeutic elements described elsewhere herein.

Figure 20A:
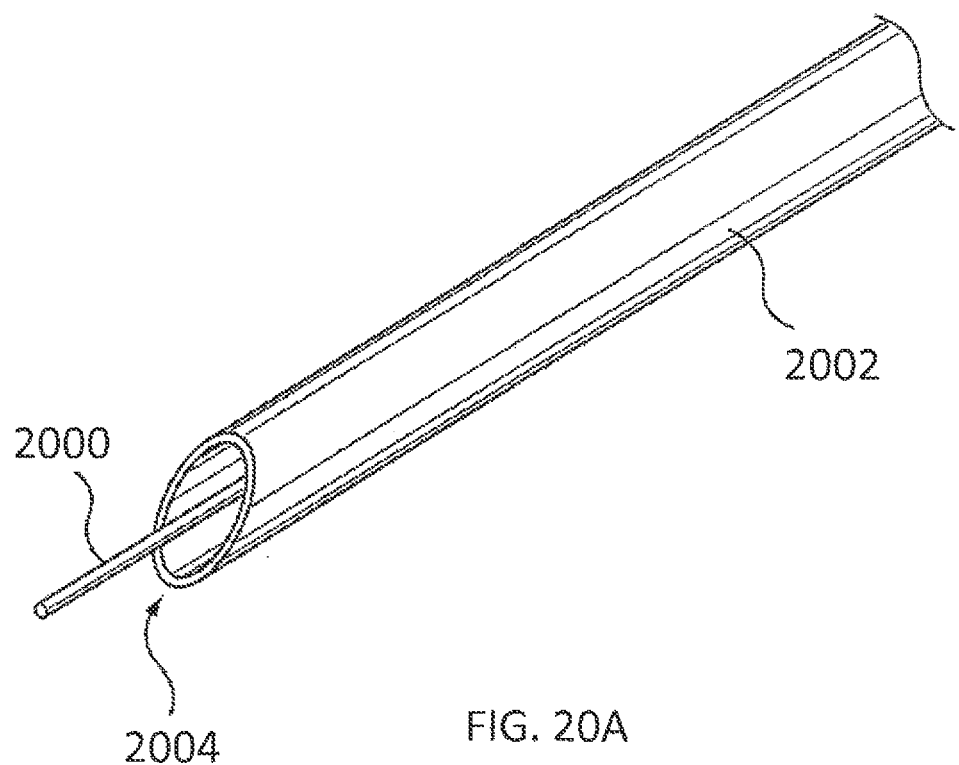
Figure 20B:
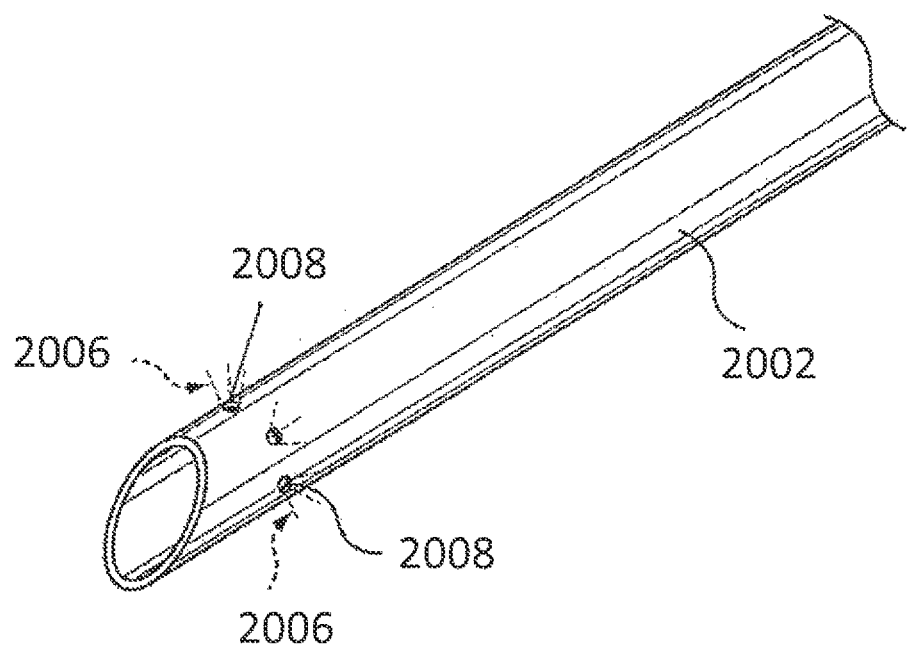
Figure 20C:
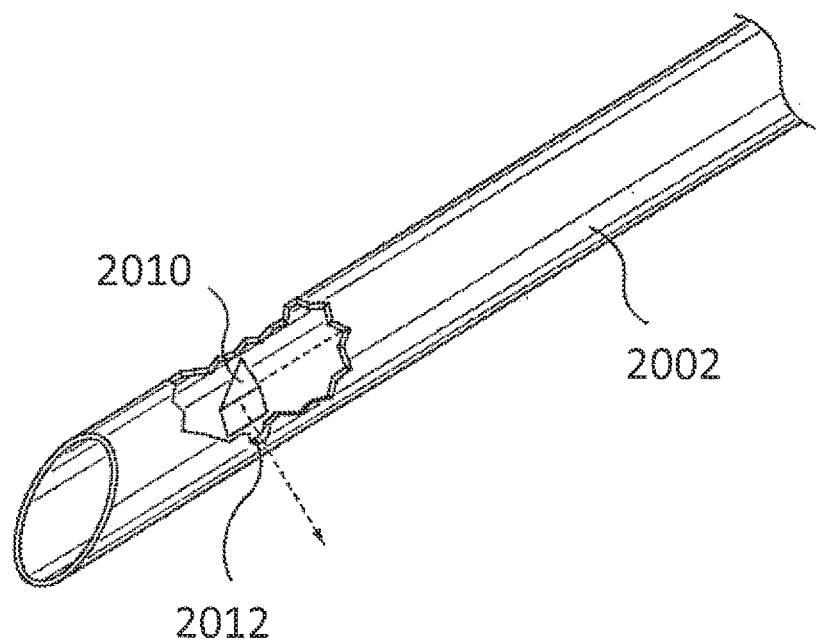

FIGS. 20A to 20C depict embodiments of exemplary light-based therapeutic elements that may be used to heat or ablate target tissue. FIG. 20A shows a fiber optic approach where a light fiber (2000) is deployed from the distal end of a guiding/docking device (2002), shown here as a needle. Once the light fiber (2000) is positioned proximate the distal end (2004) of the guiding/docking device (2002), it may be activated to generate heat within the target tissue. The light fiber (2000) may be repositioned and activated in multiple locations to complete the therapy. In some cases, it may be desirable to extend the light fiber (2000) beyond the distal end (2004) of the guiding/docking device (2002) up to about 1 cm, In other cases, it may be desirable to recess the light fiber (2000) proximal to the distal end (2004) up to about 5 mm.

FIG. 20B shows another variation where light (2006) from one or more light fibers (not shown) exits the side of the guiding/docking device (2002) via holes (2008). Once positioned, the individual light fibers may be activated one at a time, in pairs, in groups, or all simultaneously. Further, all fibers may activate at the same or different power levels. Depending on the configuration, the energy distribution around the circumference of the guiding/docking device (2002) may be symmetric/concentric or asymmetric/eccentric.

In some variations, the same light fiber(s) used to deliver energy may also be configured to measure temperature via operatively connecting the fiber to an IR temperature sensor. The light fiber may then switch back and forth or multiplex in order to intermittently monitor temperature during the treatment.

FIG. 20C shows an alternative light-based device where a laser diode (not shown) and prism (2010) are used to deliver energy to the target tissue. In this case, the laser diode may be located anywhere proximal to the prism (2010), which is located near the distal end of the guiding/docking device (2002), depicted as a needle, in this example. Once activated, the prism (2010) may direct the energy out one or more side holes (2012) to generate the desired heat within the target tissue. If the laser wave length were extended into the infra-red range (e.g., ≥800 nm), then light absorbing dyes could be used to increase the range or size of affected tissue. Such dyes may be injected at the site through a lumen in the guiding/docking device (2002) just prior to activating the laser.

Figure 21A:
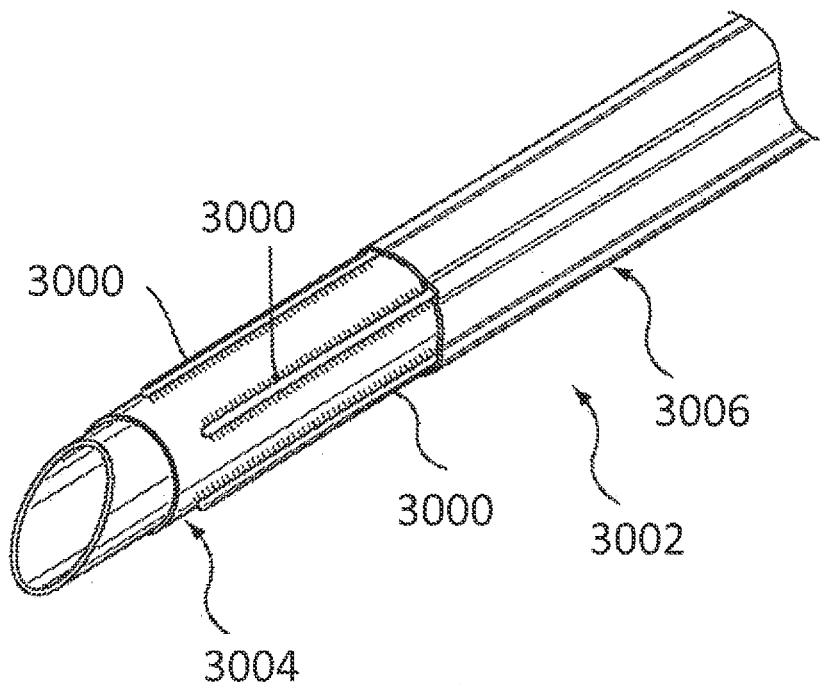
Figure 21B:
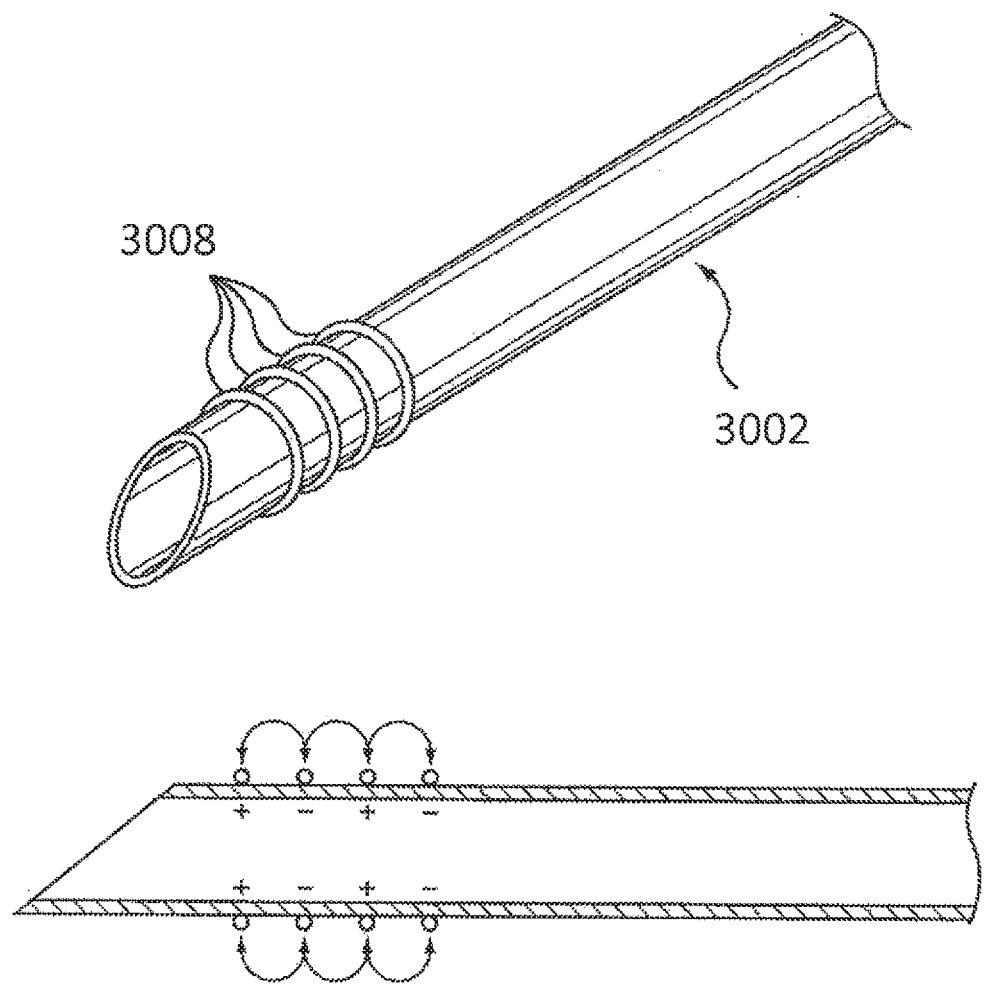

The therapeutic elements may also include multi-polar embodiments, as shown in FIGS. 21A to 21B. Multi-polar electrode approaches would have the effect of increased flexibility and/or control over lesion formation. Since each electrode can be controlled independently, each may also be capable of monitoring tissue characteristics (e.g., impedance or temperature). These characteristics may be used by the controller and/or user to adjust the application of energy to optimize therapy and/or provide safety shut-offs. For example, if the temperature of two electrodes is lower than a pre-specified target and the other two electrodes are at or above said pre-specified target, the controller may increase the. power level to those two electrodes to increase the tissue temperature at those two electrodes. FIG. 21A depicts a multi-filar configuration where multiple (e.g., four) electrodes (3000) are spaced around the circumference of a guiding/docking device (3002) with a layer of insulation or insulative jacket (3004) (e.g., PET heat shrink) between the electrodes (3000) and the guiding/docking device (3002). Herein the guiding/docking device (3002) is constructed from metal (e.g., a 14 to 18 gauge needle). The electrodes (3000) consist of individual conductive wires that are adhered to the insulative jacket (3004) and extend along the length of the guiding/docking device (3002) and are electrically isolated from one-another via an insulative jacket (3006) (e.g., PET heat shrink) along the proximal shaft. In this configuration, the active length of each electrode may range from, about 3 mm-15 mm, and the diameter of each electrode may range from about 0.012 cm-0.026 cm. In an alternative embodiment each conductive wire may be individually insulated along the proximal length with insulation removed along the distal portion to form the electrodes. These electrodes may be energized, for example, in a monopolar or bipolar' (e.g., 900° or 180° apart in a four electrode configuration) fashion.

In yet a further variation, as shown in FIG. 21B, multiple (e.g., four) circumferential electrodes (3008) are positioned around the guiding/docking device (3002) with insulative layers similar to those described in FIG. 21A. In this configuration, the electrodes may be comprised of metallic bands, coils, or wires and may be spaced apart by about 3 mm-5 mm. These electrodes may be energized, for example, in a monopolar or bipolar (e.g., adjacent or alternating pairs) fashion.

Figure 22:
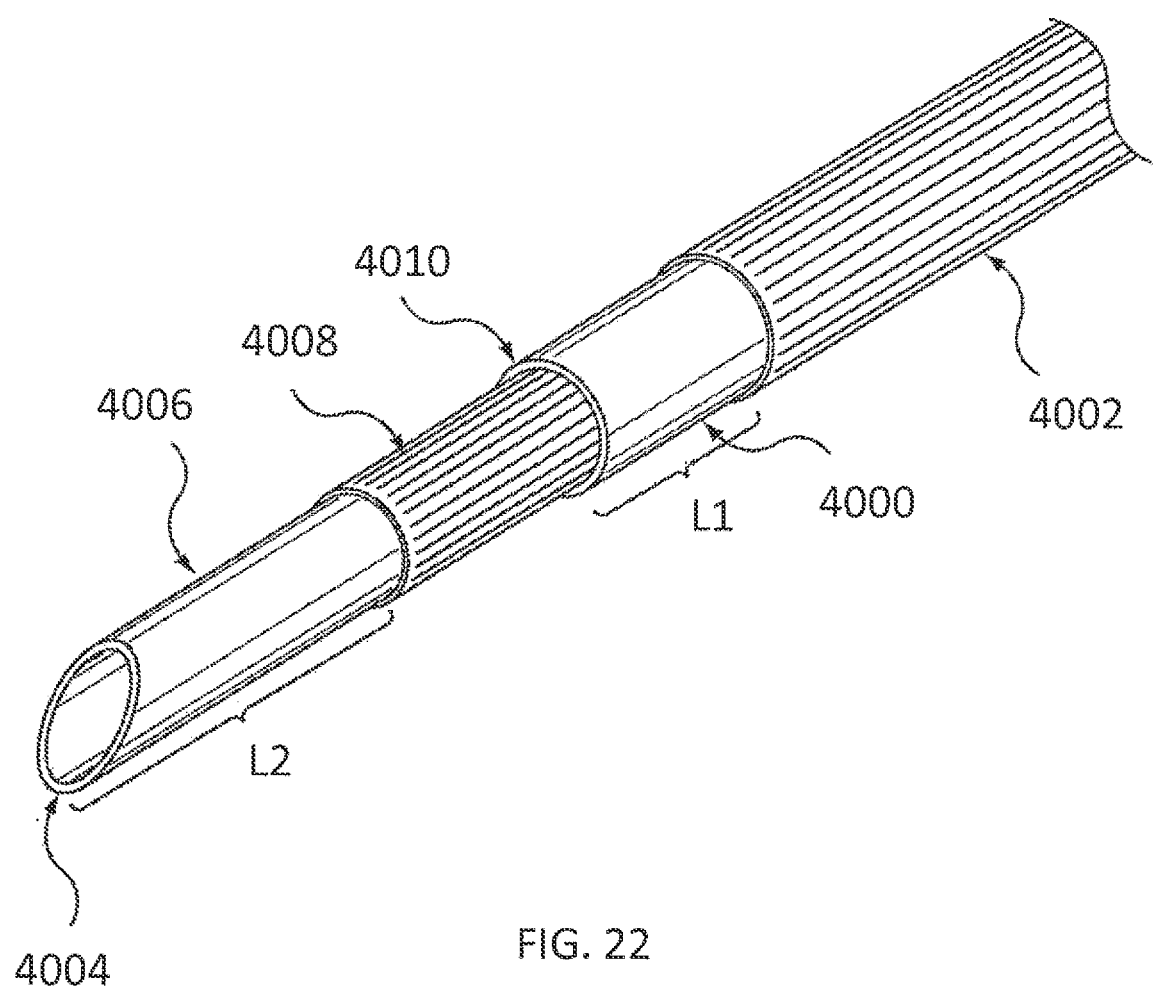

The energy delivery element may also comprise a bipolar coaxial needle device, as depicted in FIG. 22, where the outermost element is the return electrode (4000), which in this variation consists of a 16 to 18 Gauge hypodermic tube insulated on the outside with a layer of polyester shrink tubing or other non-conducting material (e.g., parylene) (4002). The insulating layer begins at a specified distance, L1, from the distal end (4010) and extends fully proximal. Inside the outermost element is the active electrode (4006), consisting of either a solid shaft or hollow tube, with an insulating layer (4008) beginning a specified distance, L2, from the distal tip (4004) and extending fully proximal. L1 and L2 may range from approximately 2 to 8 mm. In some instances, the distance between the two electrodes is fixed, but in others, it may be adjustable. If adjustable, the generator may be configured to detect changes in the distance and display recommended power settings or automatically adjust power settings based on detected distance. By way of example, should the distance increase, the power and/or time may be increased. Alternatively, there may be a mechanical indicator at or near the proximal end of the device (e.g., incorporated into the handle) that shows the distance along with the recommended power level. In this case, the operator would then manually set the power via the user interface on the generator. If the return electrode (4000) is significantly larger than the active electrode (4006), bipolar application of energy may result in substantial heating of the active electrode with minimal or no heating of the return electrode. This would allow for a single lesion to be generated proximate the active electrode without the need for a separate neutral electrode placed on the patient's skin. It would also allow for the neutral electrode to monitor tissue characteristics in contact with it, which may be used as an indicator of when to cease treatment. For example, the active electrode may heat tissue via resistive and/or conductive heating until the neutral electrode detects an increase in temperature or impedance. The system may then cease application of energy should a pre-set or user-controlled threshold be reached. If the distance between the electrodes is adjustable, it provides the advantage of user adjustability. For example, if the patient has a very large ovary, the user may choose to position the electrodes further away from each other to generate a larger lesion, thus reducing procedure time. In this instance, both electrodes may be approximately the same size, such that they both heat the tissue and potentially create a continuous lesion between them via resistive and/or conductive heating.

As previously stated, the therapeutic elements may consist of one or more of the following: a radiofrequency energy element; a direct heating element; a cryoablation element; a cooling element; a mechanical disruption element; a laser/light; a microwave antenna; an unfocused ultrasound element; a partially-focused ultrasound element; a focused (HIFU) ultrasound element; and/or means for delivering heated water/saline, steam, a chemical ablation agent, a biologic or pharmaceutical agent, a drag-eluting implant, a radioisotope seed, or a mechanical implant, which may be either passive or active via application of remote energy (e.g., ultrasound to induce vibration). There may be mechanical methods built into the device design to prevent the therapeutic element from being advanced more deeply than a predetermined depth.

If energy is being applied via one or more electrodes or elements, it may be applied in a monopolar, bipolar, or combined fashion; each element may fire simultaneously or sequentially; energy may be applied in a continuous or pulsed fashion, and the system may have a user interface (FIG. 23, 5010) that allows the user to choose which electrodes or elements are active to customize the therapy for each patient. Different combinations of electrodes could be used to deliver energy such that patterns of treatment are achieved. For example, one embodiment could contain three electrodes (A, B, C), Any or all three could deliver energy in a monopolar fashion and/or any combination of electrodes could also deliver energy in a bipolar fashion (e.g., A to B, B to C, A to C). Energy delivery could alternate in pulses (mono A, followed by mono B, followed by mono C, followed by bipolar A to B, bipolar B to C, etc,). Or, different frequencies of energy could be delivered simultaneously or sequentially (e.g., mono at 465 kHz and bipolar at >1 MHz). These combinations may also be used for tissue mapping prior to or during the delivery of therapy. A monopolar application of energy would have the effect of generating a treatment area adjacent to the electrode and may be used to generate larger lesions at higher power in shorter time, relative to a bipolar application. A bipolar application of energy would have the effect of generating a treatment area adjacent to each electrode with the potential to create a continuous lesion spanning the volume between the electrodes via either resistive or conductive heating. A bipolar application of energy may also allow for lower power and smaller lesions. In addition, a bipolar application of energy may also allow for tissue characteristics (e.g., impedance, temperature) to be monitored at each electrode and adjustments made either before (e.g., user or system selected based on tissue characteristics, such as impedance, or based on electrode position) or during treatment (e.g., switching which electrode is active versus the return). A combined application of both monopolar- and bipolar-energy would also have the effect of generating a treatment area based upon tissue characteristics monitored at each electrode or between pairs of electrodes (e.g., impedance, temperature) with the added ability to use a single electrode, if appropriate. In this instance, the return electrode may be outside the ovary or on the skin of the patient. A continuous application of energy may have the effect of generating a lesion via a combination of both resistive and conductive heating. Application of energy in a pulsed fashion would limit the amount of conductive heating and may allow for additional measurements to be made between pulses, when energy is turned off or reduced to a lower power. These additional measurements may then be used to alter or cease the application of energy and/or to provide additional feedback to the user. The use of different frequencies may allow for reduced or increased electrical coupling between multiple conductors (e.g., wiring) or electrodes. In the case of tissue mapping, the use of different frequencies may elicit different responses from different types of tissues and/or different states of tissues (e.g., ablated tissue or unablated tissue). Furthermore, in the case of ablation creation, the use of different frequencies may create different lesion characteristics.

A generator is generally included in the systems described herein to create energy to be delivered through the therapeutic element(s). The systems may include sensing elements on either the therapeutic element and/or on the guiding/docking device to detect parameters such as temperature, impedance, or other parameters that could guide therapy delivery. A feedback control system may use detected parameters within software algorithms such that treatment is delivered automatically and could be automatically stopped when certain temperature, time, power and/or impedance thresholds have been crossed. The system could also deliver two or more different sets of energy parameters. For example, to the system, could be configured to deliver lower energy or temperature for a longer time (e.g., to ablate and/or otherwise affect a larger volume of tissue) and higher energy or temperature for a short time (e.g., to control bleeding and/or desiccate/char tissue to enhance visualization). The parameters of the therapeutic element or the pattern of the targeting within the ovary could be configured to preferentially target certain regions and/or tissues and spare others. The sensing elements could also be used before treatment is applied to characterize or map the target tissue; for instance, impedance measures could be used to sense if the docking/guiding device and/or therapeutic element is adjacent or within cysts, to sense if portions the docking/guiding device and/or therapeutic element are within the ovary or outside the ovary, or to sense where portions of the docking/guiding device and/or therapeutic element are relative to the vasculature or other important structures. The sensing elements could also be used during treatment to dynamically adjust treatment parameters. The sensing elements could be used to measure temperature and/or impedance. For example, a temperature-sensing element could be located on each of a plurality of electrodes. In some variations, two temperature-sensing elements could be located on a single electrode. Power could be adjusted based on the hottest temperature-sensing element or could be adjusted based on some combination of the multiple sensing elements, such as an average or weighted average. In another example comprised of bipolar electrodes and temperature sensing elements on each electrode, the active electrode (the electrode delivering the energy) could be interchanged with the return electrode before or during energy delivery based on the measured temperatures and/or impedances.

Furthermore, the sensing elements could also be used to detect if the device moves inappropriately during the treatment delivery. For example, device movement could be inferred by sensing sudden changes in temperature, impedance, and/or power. In one variation, the sudden changes could be based on an instantaneous measurement exceeding some predetermined threshold away from an averaged measurement. In another variation, the variance of a signal, such as power, could be tracked during treatment and movement could be inferred when the variance deviates by a predetermined threshold, such as a percentage difference. If movement is inferred, then the generator could automatically terminate energy delivery and/or inform the user that the device has moved.

When radiofrequency energy is employed, the generator may deliver the energy at a power of 30 watts or less, and for a duration of 60 seconds or less. In some variations, the generator may deliver the energy at a power ranging from 4 to 15 watts, and for a duration of 10 to 45 seconds. The radiofrequency energy may be supplied in a pulsed or continuous fashion. In other variations, the generator may deliver the energy at a first power range (e.g., 0 to 30 watts or 4 to 15 watts) for a first duration (e.g., 10 to 45 seconds) followed by a second, higher power range for a second, shorter duration (e.g., less than 10 seconds). The specific power settings may be pre-determined or may be determined based on current or previously acquired system feedback, such as temperature, impedance, power, and/or time. One example of using previously acquired system feedback is to adjust the second, higher power range based on the maximum power utilized during the first duration. Applying higher power ranges or temperatures towards the end of the energy delivery can create different lesion characteristics including, but not limited to, increased volume of tissue necrosis, cauterization of blood vessels, and enhanced echogenicity via increased tissue desiccation, tissue contraction, and/or formation of steam or microbubbles. To prevent or minimize the amount of tissue deposition on the therapeutic element due to the ablations (which could lead to sticking when retracting or deploying the therapeutic element), coatings or surface treatments may be optionally applied to the any of the therapeutic elements described herein. Examples of coatings include Parylene, PTFE, hydrogels, silicone oil, and oxidation. If the coating is not electrically conductive, then additional surface treatments such as acid etching or laser etching, could be selectively applied to the coating to allow electrical energy to pass through.

Figure 32:
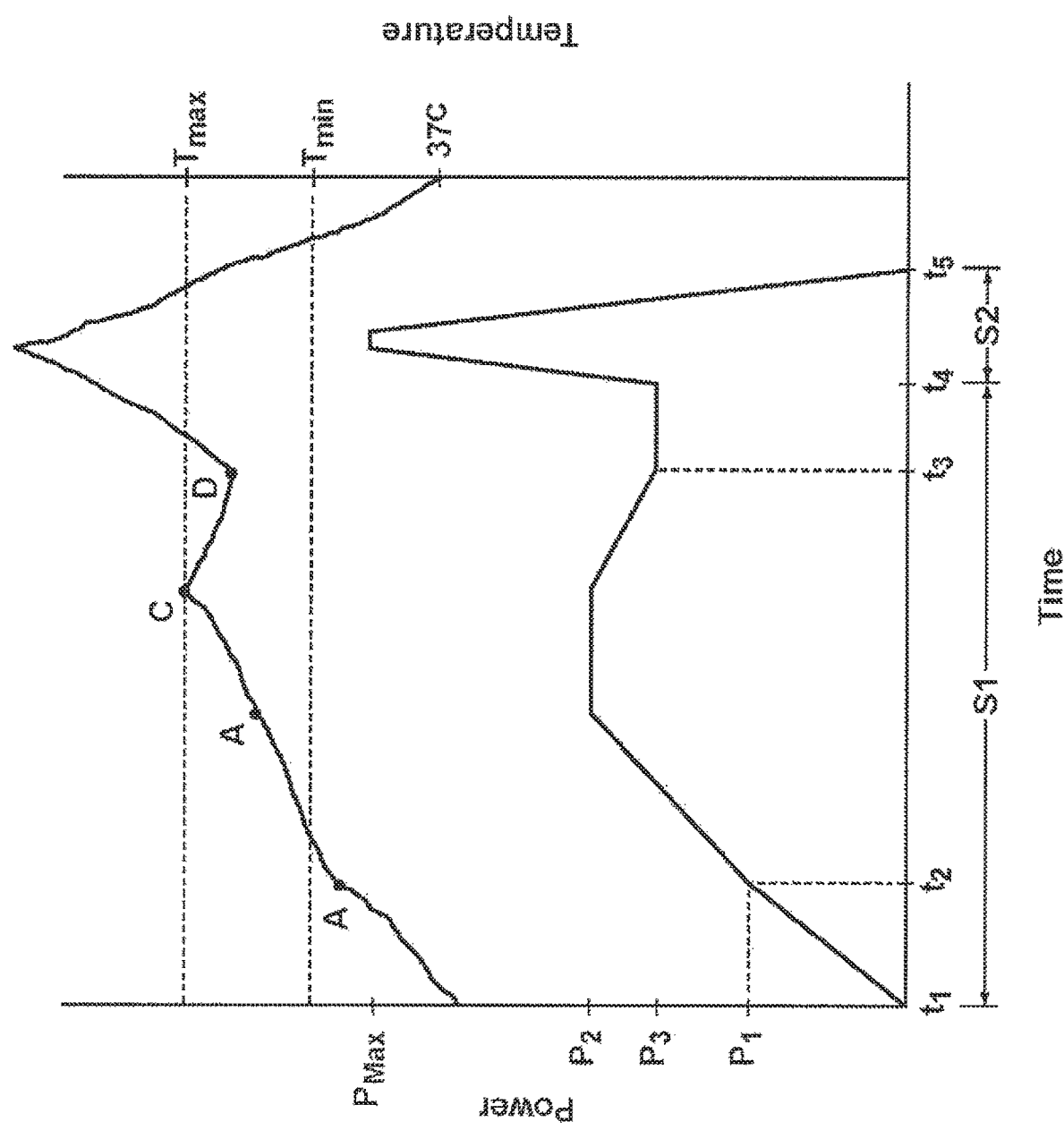
FIG. 32 depicts an exemplary Power/Temperature Curve.

FIG. 32 depicts an exemplary Power/Temperature Curve wherein energy is delivered in a two-phased approach such that the first stage (S1) is designed to heat the tissue and a second stage (S2) is designed to char/desiccate the tissue and/or cause steam and/or microbubble formation. At the start of the energy delivery (t1) power is linearly ramped to a pre-set power (P1) over time, t2. Shortly after t2, temperature (A) is compared to a pre-determined target range (Tmin-Tmax) (e.g., 65 to 85 degrees C.). If temperature (A) is less than Tmin, power may step or ramp up until the temperature is greater than Tmin. This is depicted by power (P2) and temperature (B). As a safety feature, a maximum power may be set. As the tissue heats and changes its characteristics, temperature may also increase. Should the temperature (C) reach or exceed a pre-set maximum temperature (Tmax), either the treatment could be terminated (not shown) or power could be reduced over time (P3) until the temperature (D) once again falls below Tmax at time (t3). At the end of first stage (SI), the algorithm then enters the second stage (S2), where power ramps in a linear or step-wise fashion to a maximum power, Pmax and hold until time (t5), upon which energy delivery is terminated. The period defined by (t5-t4) may, for example, be between 3 to 10 seconds in order to char/dessicate/coagulate the tissue or cause steam and/or microbubble formation.

Figure 33:
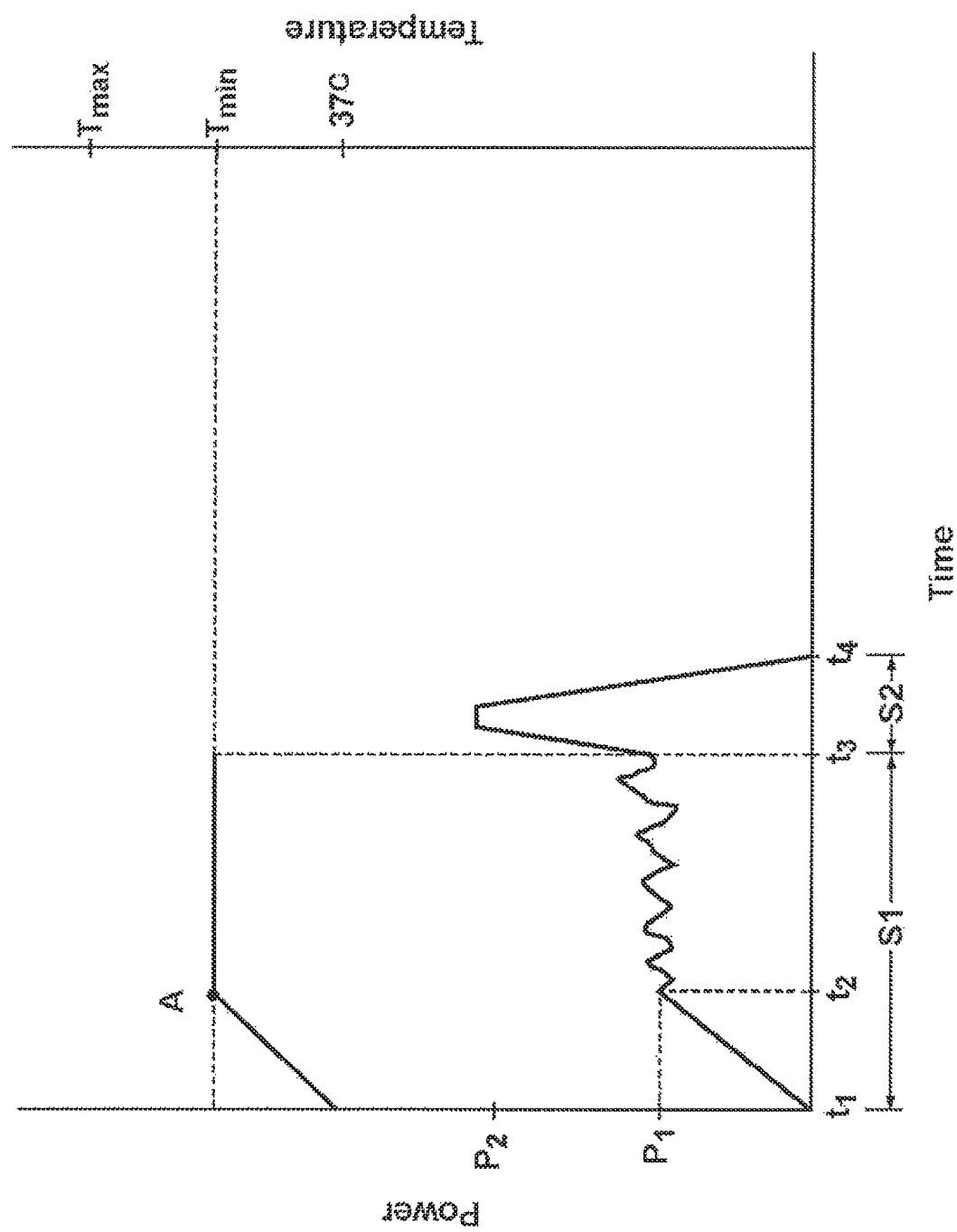
FIG. 33 depicts another exemplary Power/Temperature Curve.
Figure 34:
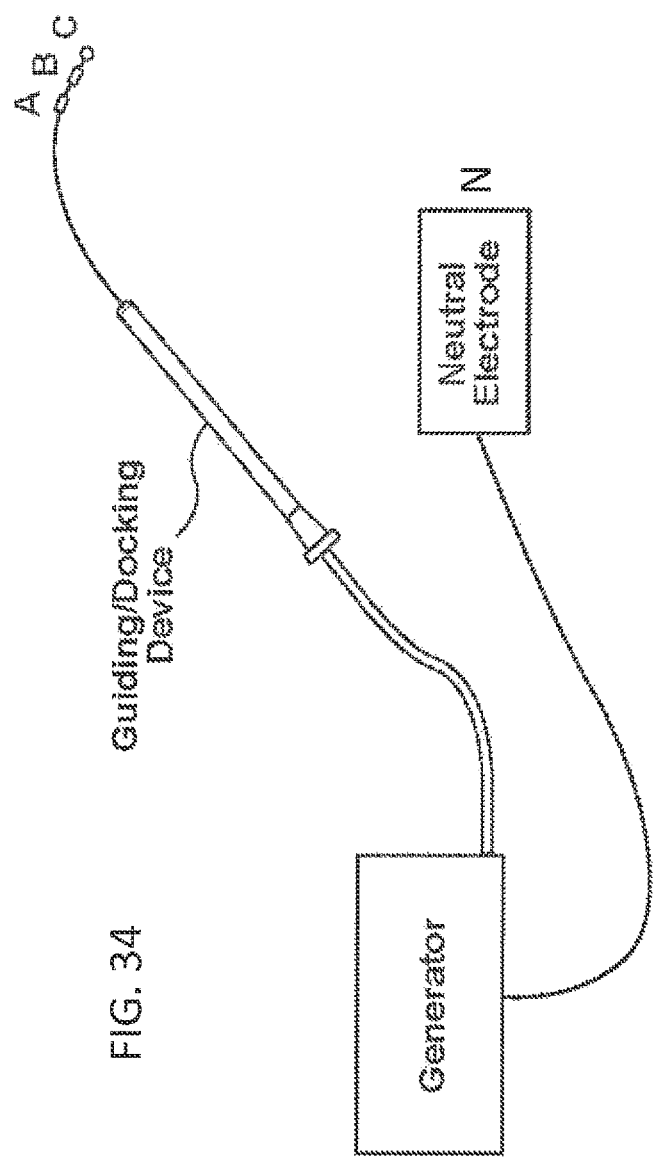
FIG. 34 depicts an embodiment of a system including a neutral electrode for measurement of impedance.

Alternatively, the generator may deliver power in a manner to achieve a desired target temperature but limit the power to some maximum power (e.g., 30 watts or less) in the event the target temperature cannot be achieved. FIG. 33 depicts an exemplary Power/Temperature Curve wherein energy is delivered in a two-phased approach such that the first stage (S1) is designed to heat the tissue and a second stage (S2) is designed to char/dessicate the tissue or cause steam and/or microbubble formation. At the start of the energy delivery (t1), power is linearly ramped until a minimum target temperature (Tmin) (e.g., 65 to 85 degrees C.) is reached. This event is denoted by power (P1) and temperature (A) at time (t2). As a safety feature, a maximum power may be set. The generator then continually adjusts power in an effort to maintain the minimum temperature (Tmin) without exceeding a pre-set maximum temperature (Tmax). As the tissue heats and changes characteristics, a sudden increase in temperature may occur (not shown). Should the temperature reach or exceed the maximum temperature (Tmax), the generator will adjust power down or terminate the treatment. At the end of the first stage (S1) which occurs at time (t3), the algorithm then enters the second stage (S2), where power is ramped in a linear or step-wise fashion to a second power, P2, and holds until time (t4), upon which energy delivery is terminated. The period defined by (t4–t3) may, for example, be between 3 to 10 seconds in order to char/desiccate/coagulate the tissue or cause steam and/or microbubble formation.

Figure 23:
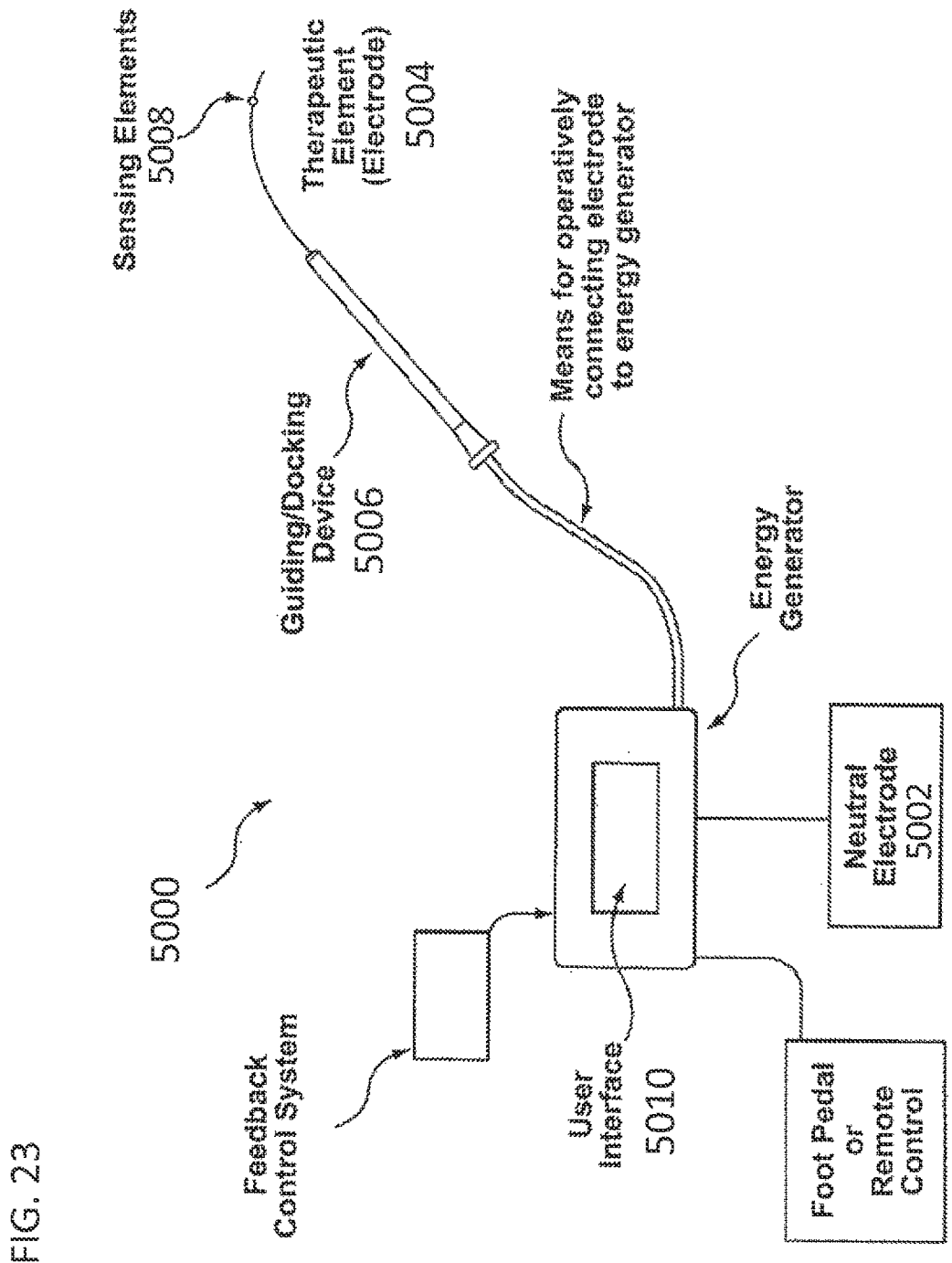
FIG. 23 depicts an embodiment of a system for energy delivery via a transvaginal, laparoscopic, percutaneous, or surgical procedure.

An exemplary system. (5000) is illustrated in FIG. 23. In this embodiment, the system is configured for monopolar energy delivery using a neutral electrode (5002), which would be affixed to the skin of the patient, Bipolar configurations would eliminate the need for an externally-placed neutral electrode. For example, the therapeutic element (5004) may be configured to have two or more electrodes of approximately the same size and spaced apart to deliver energy in a bipolar or multi-polar fashion (not shown). Alternatively, the neutral electrode (5002) may be incorporated into the docking/guiding device (5006). In a further-variation, the neutral electrode may be incorporated into a cover placed over the transducer of the ultrasound probe or incorporated into the needle guide. In these cases, the neutral electrode may be larger than the electrode located on the therapeutic element such that only the electrode located on the therapeutic element heats significantly. Furthermore, the sensing elements (5008) may be used to measure parameters either intra-procedurally or post-procedurally to assess for technical success of the procedure. For instance, impedance changes could accompany desirable changes in tissue characteristics in successful treatment delivery.

Some variations of the system could be configured with bipolar electrodes to deliver therapeutic doses of energy. Here a neutral electrode (affixed to the skin of the patient, incorporated into the docking/guiding device, or incorporated elsewhere away from the distal end of the device) could be utilized to measure, impedance values from one or each of the therapeutic electrodes before or during energy delivery. The impedance values between the therapeutic bipolar electrodes and/or between a therapeutic electrode and the neutral electrode could be used to determine the relative location of the therapeutic elements within the ovary. An example is shown in FIGS. 34 and 35A-35C. Therapeutic elements, such as electrodes, A and B could be configured in a bipolar manner such that energy is delivered from A and returned to B (or vice versa) to generate a therapeutic effect. Impedance could also be measured between A and B. A neutral electrode, N, could be used to measure impedance from A to N and from B to N by applying low, non-therapeutic levels of energy. Optionally or additionally, a sensing element, C, could be located at the tip of the device to measure the impedance between C and N, A and C, and/or B and C. Comparing these different impedance measurements could provide feedback for the relative locations of A, B, and C.

Figure 35C:
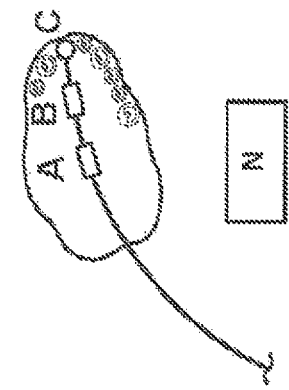
FIGS. 35A-35C depict the system of FIG. 34 in varying portions of the ovary.
Figure 35B:
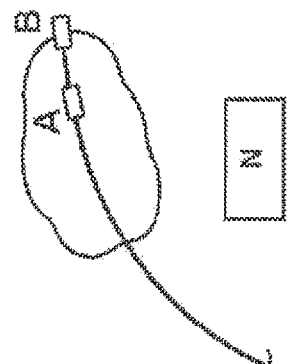
Figure 35A:
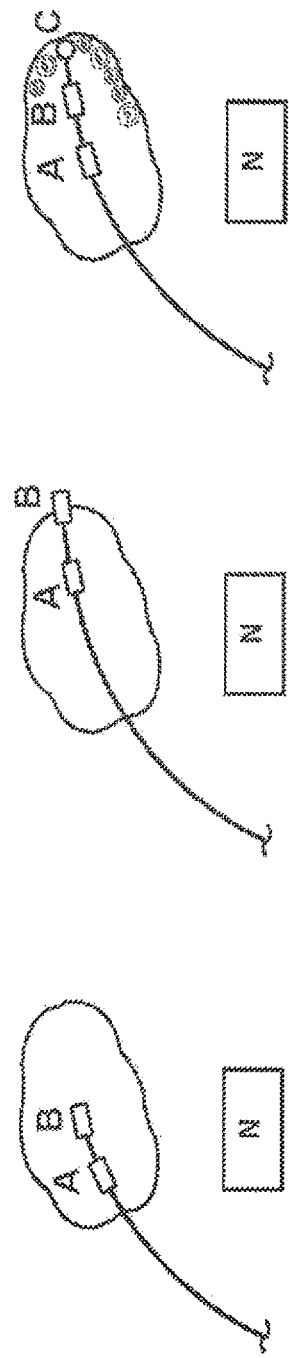

FIGS. 35A-35C provide examples where electrode A and electrode B are both inside the ovary. In FIG. 35B, electrode A is inside the ovary and electrode B is partially outside the ovary. In FIG. 35A, the impedances of A-to-N and B-to-N are similar since the electrical paths are similar. However, in FIG. 35B, the impedances of A-to-N and B-to-N could be measurably different depending on the composition of the non-ovarian tissue-contacting electrode B. In one variation, the non-ovarian tissue could be bowel filled with gas and result in higher impedance. Other tissues adjacent to the ovary that could result in higher impedance are fat deposits. In another variation, the non-ovarian tissue could be bowel, muscle, or a blood supply such that the impedance of B-to-N is lower than the impedance of A-to-N. Based on these impedance measurements, the generator could provide the operator with different feedback regarding the relative location of the device. Similarly, FIG. 35C depicts electrodes A and B within stromal tissue of the ovary and sensing element C within a follicle or cyst. Impedance measurements A-to-B, A-to-C, and/or B-to-C (or optionally A-to-N, B-to-N, C-to-N), could be used to impute that the sensing element at the tip of the device is within a follicle and thus closer to the outer surface of the ovary. Therefore, the generator could provide feedback to the operator to stop advancing the device in order to prevent the tip from unintentionally exiting the ovary. Additionally, if sensing element C did exit the ovary, the impedance measurements from A-to-B, A-to-C, and/or B-to-C (or optionally A-to-N, B-to-N, C-to-N) could be used to detect this condition.

Figure 24:
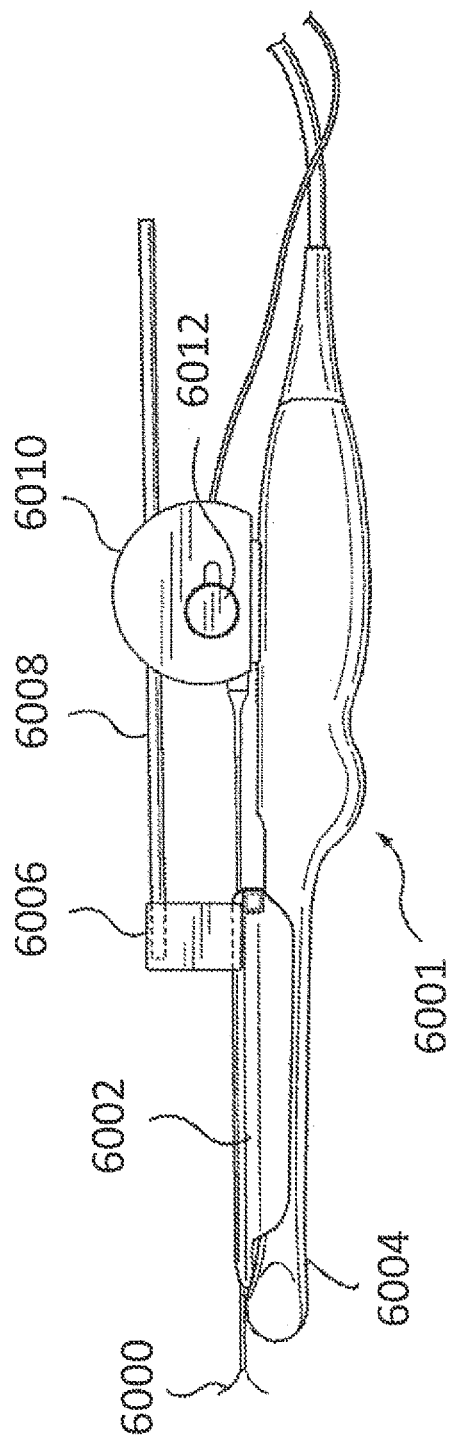
FIG. 24 depicts an embodiment of a device for providing planar orientation of therapeutic element(s) during transvaginal ultrasound-guided procedures.

According to embodiments described herein, which may partially or as a whole combine with other embodiments, it may be useful for the systems to include features configured to maintain the orientation of the energy delivery elements, e.g., radiofrequency energy elements, in a single plane, which may be desirable for visualization optimization. The features for maintaining planar orientation may include the use of ribbon and/or use of side ports on the guide/docking device to better guide deployment. In other variations, orienting a planar therapeutic element such that it is in plane with a 2-dimensional ultrasound field may be accomplished by placing visual cues or identifiers (e.g., markers comprised of an echogenic material; markers comprising echogenic bands, rings, arcs, or other geometric structures, etc.) or tactile cues or identifiers (e.g., a wing-like structure) on a portion of the device, e.g., the proximal end of the device that deploys the therapeutic element into the ovary. For transvaginal procedures, providing features for maintaining the rotational orientation between the ultrasound probe/transducer, the guiding/docking device and/or the therapeutic element may also be employed. FIG. 24 shows an exemplary system (6001) for maintaining therapeutic elements (6000) in the two-dimensional plane with the ultrasound visualization field/plane. For needle-guided transvaginal procedures, a needle guide (6002) is affixed to the shaft of the probe to ensure that the tip of the needle is always within the field of view of the probe (6004). The needle guide (6002) may also ensure that the needle enters the field of view from the. same location and travels along the same angle with respect to the head of the ultrasound probe/transducer (6004). However, when therapeutic elements with a curvilinear shape (6000) need to be deployed, planar orientation must be maintained in order to see them as the probe (6004) or other system elements are manipulated. In one instance, the needle guide may incorporate a unique geometry that mates with a guide on the docking device. In this instance, 'an offset coupler (6006) may be affixed to the needle guide (6002). The offset coupler (6006) may include a guide rod (6008), which can slide through an advancing handle (6010) by sliding an advancing mechanism (6012) forward to force the therapeutic elements (6000) into the tissue. The advancing mechanism (6012) may then be pulled back to recapture the therapeutic elements (6000) when finished.

Figure 26:
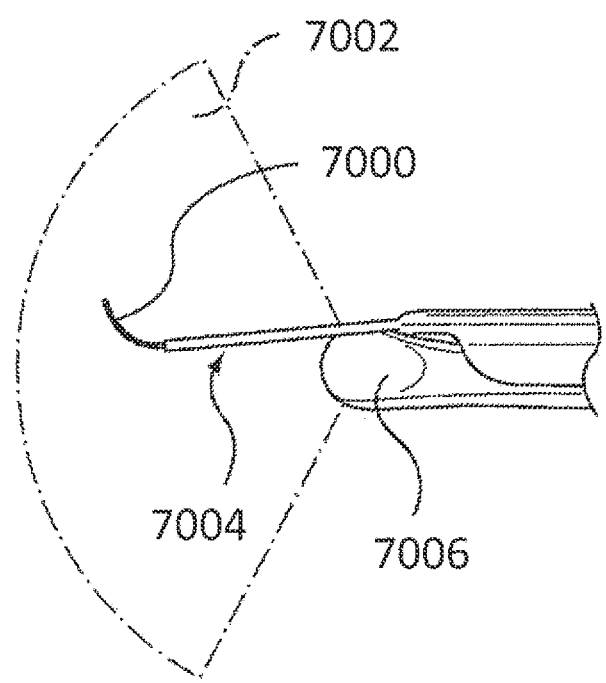
FIG. 26 illustrates an exemplary method for providing planar orientation of a curvilinear therapeutic element.

Referring to the embodiment shown in FIG. 26, a curvilinear therapeutic element (7000) is shown within the ultrasound field of view (7002). If the docking/guiding device (7004) and/or curvilinear element (7000) are rotated a few degrees with respect to the ultrasound transducer (7006), then the curvilinear element (7000) would no longer exist within the same plane as the ultrasound visualization plane and the curvilinear element would no longer appear on the ultrasound display. Therefore, the operator would need to rotate the docking/guiding device (7004) and/or curvilinear element (7000) until the curvilinear element reappeared on the ultrasound display. This could increase procedure time and increase the risk of patient injury by requiring additional manipulation of the device. It may also be beneficial to have an alignment feature that orients or aligns the curvilinear element to the ultrasound visualization plane in a manner that ensures the curvilinear element is visible as it deploys. Visualizing the entire element as it deploys may allow the operator to more precisely position the element in the desired location. In other embodiments, it may only be necessary to see the distal tip of the curvilinear element (7000), to ensure that it is still within the target tissue. Visualization of the distal tip of the curvilinear element (7000), optionally combined with visualization of the distal tip of the docking/guiding device (7004), may provide adequate visualization for precise positioning.

Figure 25:
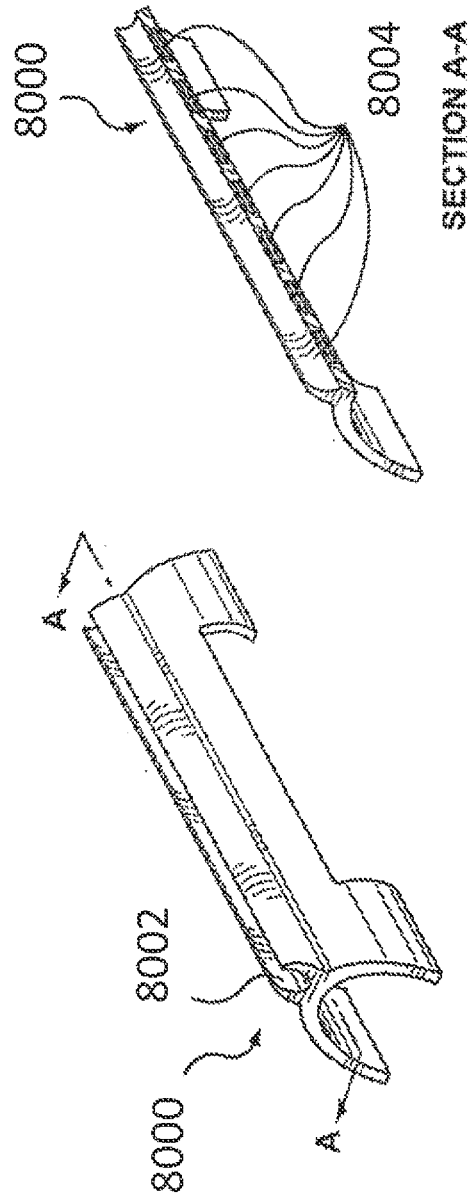
FIG. 25 shows various views of an embodiment of a magnetic needle guide.

In some cases, it may be desirable to have the ability to decouple and re-couple the docking/guiding device from the needle guide in situ. FIG. 25 depicts an exemplary magnetic detachable needle guide (8000), which may be combined with other embodiments described herein. For example, the needle guide (8000) may incorporate a trough (8002) with embedded neodymium magnets (8004) underneath it that may be used to position and hold a metallic docking/guiding device in place, while also making it removable.

Alternative mechanisms for maintaining planar alignment are provided in FIGS. 27A to 27F. For example, an alignment adapter (9000) may be attached to a handle (9002) of a transvaginal ultrasound probe (9004). Alignment adapter (9000) may be removably attached to the ultrasound probe handle (9002) by snapping on, strapping, clamping circumferentially via a two-piece or hinged clamshell, or other suitable ways. In order to be adaptable to a variety of ultrasound probes, the mating surface (9006, shown in the cross-sectional view of FIG. 27B) may include features such as a low durometer or other suitably conformable polymer (e.g., neoprene, polyurethane, silicone, etc.). These features may be molded into alignment adapter (9000) or provided as separate insert pieces. The alignment adapter (9000) may further comprise a receiving lumen or cavity (9008) between the main body of the alignment adapter and a guide (9010) of the guiding/docking device (9012). The alignment adapter (9000) may also include an adjustable element (e.g., a mechanical lock) (9014) that may be used to fix or hold steady the guiding/docking device (9012) or allow it to be moved. For example, when the adjustable element (9014) is in a locked (down) position (FIG. 27C), it aids in aligning the guiding/docking device (9012) and/or therapeutic elements (9016) within the ultrasound visualization plane. In the unlocked (up) position (FIG. 27D), the guiding/docking device (9012) may be freely rotated (or rotation may be limited to, for example, about 90 degrees in a clockwise or counter-clockwise direction). Additionally, the alignment adapter could allow some limited rotation, such as plus or minus up to 20 degrees of rotation, even in the locked position. For example, the opening in the mechanical lock (9014) could be enlarged such that the guide (9010) could rotate about 10 degrees in the locked position. The limited rotation can be useful in maintaining the therapeutic elements within the ultrasound visualization plane while allowing the operator to quickly rotate the device back and forth to enhance visualization due to the motion. Similarly, subtle motion (for the purpose of enhanced visibility) could be achieved by allowing the operator to easily shift the therapeutic elements a small distance distally and proximally, such as plus or minus up to 0.25 mm. The adjustable clement may comprise a notch configured to mate with the docking device to help effect locking. The docking/guiding device (9012) may be introduced while the adjustable element (9014) is in the unlocked position (FIG. 27D) or in a partially-locked position (FIG. 27E) where the guide (9010) need not be perfectly straight and will aid in aligning the docking/guiding device (9012) as it is lowered. The geometry of the adjustable element (9014) may also be tapered such that the docking/guiding device (9012) may rest in proper alignment but still be free to rotate easily, if desired, If rotation or translation of the docking/guiding device (9012) is desired, it may further incorporate a hub (9020) to make manipulation easier. Furthermore, the alignment adapter (9014) may further comprise sliders, knobs, and/or levers, which can be used to advance/withdraw the docking/ guiding device, deploy/retract therapeutic elements, engage/ disengage the alignment mechanism, etc. Due to the alignment feature, the therapeutic elements can be maintained within the visualization plane of the ultrasound probe during an ovarian procedure.

Figure 27F:
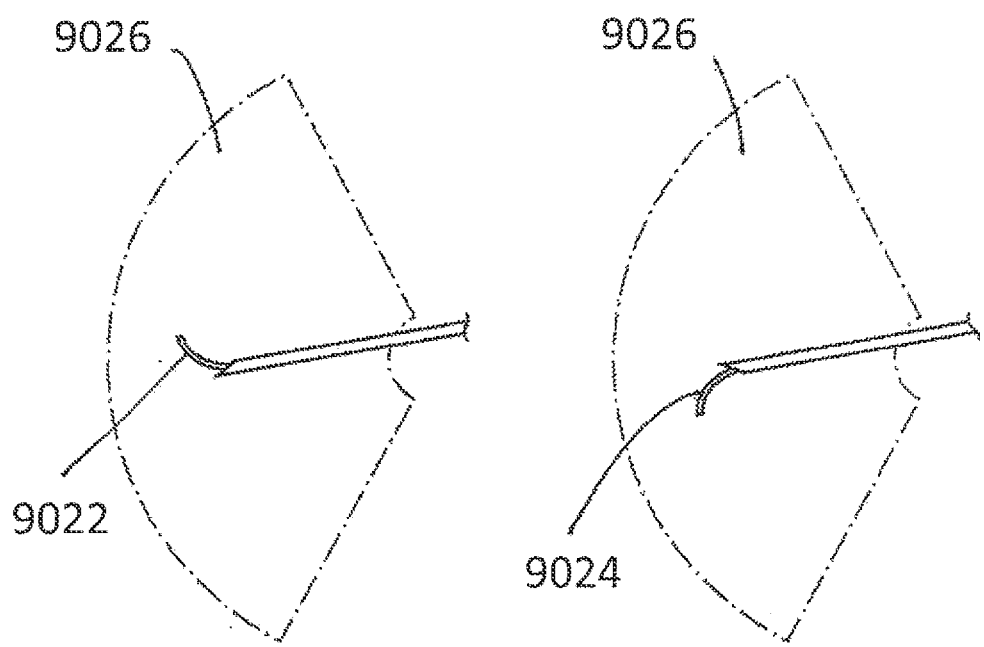

For example, as illustrated in FIG. 27F, mechanical lock (not shown) may be used to orient a curvilinear element in a first planar orientation (9022) followed by retraction and redeployment in a second planar orientation (9024), allowing for two treatments to be applied within the same visualization plane (9026) of the ultrasound probe.

Figure 28:
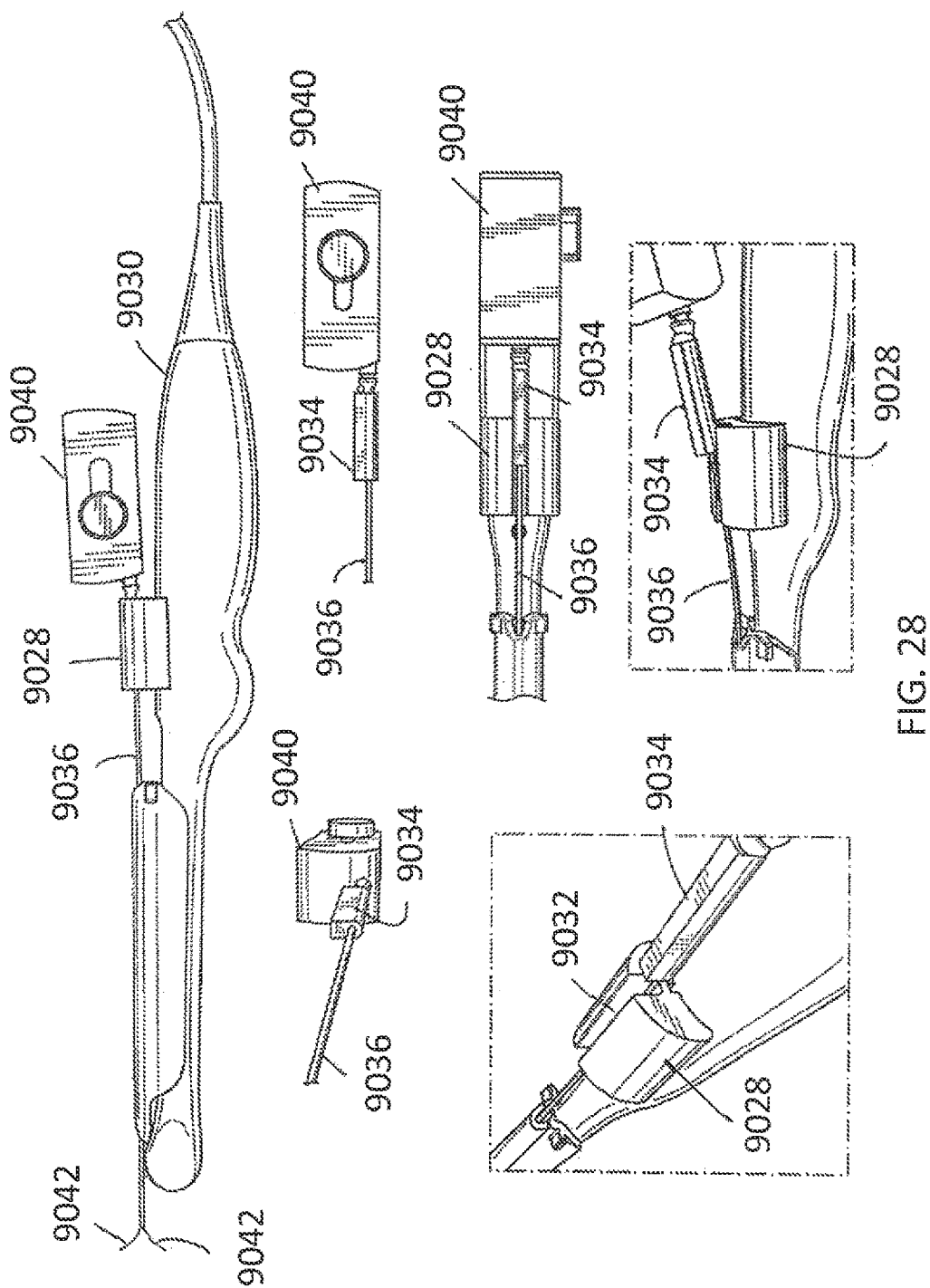
FIG. 28 depicts a further embodiment of a device for providing planar orientation of therapeutic element(s) during transvaginal ultrasound-guided procedures.

In the embodiment shown in FIG. 28, the alignment adapter (9028) can be a lock that is removably affixed to the handle of the ultrasound probe (9030) via a temporary adhesive located at the interface between the alignment adapter (9020) and ultrasound probe (9030). The adapter could also be attached with a conformable strap or clamp. Here alignment adapter (9028) includes a receiving alignment channel (9032) with a geometry that prevents or limits rotation once engaged (e.g., square or rectangular). The proximal end of a guiding/docking device (9036) incorporates an alignment element (9034), which mates with the receiving alignment channel (9032) to maintain the planar orientation of the therapeutic elements (9042) and the visualization plane of the ultrasound probe. As described previously, the alignment mechanism could allow some limited rotational or translational motion to enhance visualization. For example, the alignment channel (9032) could be larger than the alignment element (9034) by 0.025 cm which would allow some rotation but still maintain the therapeutic element within the ultrasound visualization plane. The guiding/ docking device (9036) further comprises a handle (9040), which may be used to manipulate the device and/or may further incorporate features for deploying the therapeutic elements (9042). Such deploying features may include a slider, knob, wheel, crank, and/or levers, which can be used to deploy/retract therapeutic elements (9042).

Figure 36A:
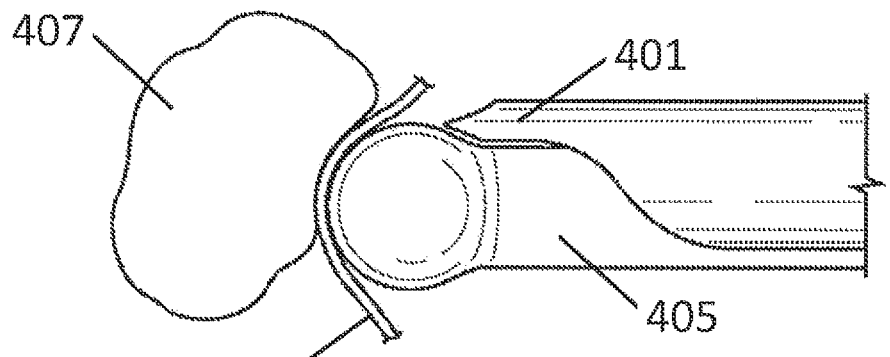
FIGS. 36A-36C illustrates an exemplary method of limiting travel of a therapeutic clement into the ovary.
Figure 36B:
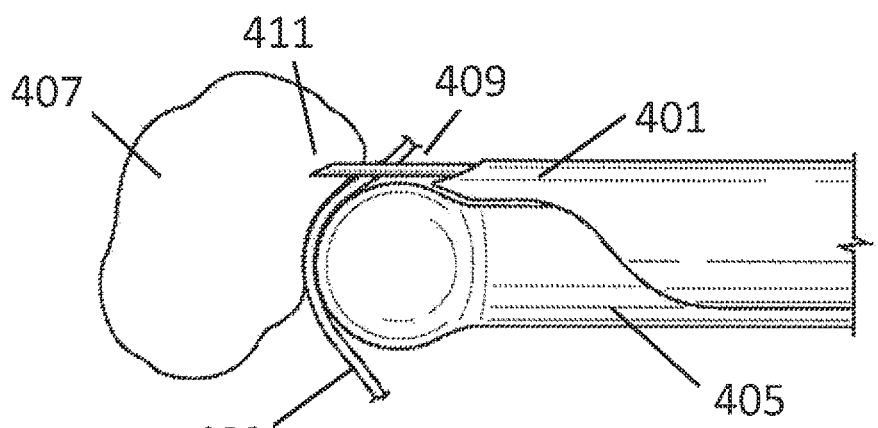
Figure 36C:
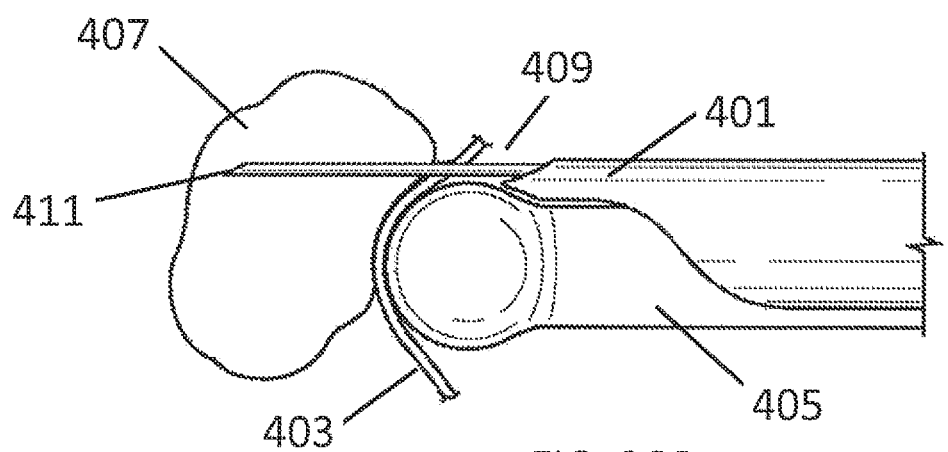

According to embodiments described herein, which may partially or as a whole combine with other embodiments, the guiding/docking device may comprise a handle, which may be used to manipulate the device and/or may further incorporate features for deploying the therapeutic elements as well as incorporating features to limit the travel of the guiding/docking device. Since the distal tip of the guiding/docking device may contain a needle (or otherwise sharp) point to pierce through the vaginal wall and capsule of the ovary, it may be desirable to prevent the needle tip from traveling too far distally and causing unintentional injury. In one embodiment, as shown in FIG. 36A, the handle (not shown) could provide tactile and/or visual feedback to inform the operator that the needle tip (411) of the guiding/docking device (409) is located at the distal end of the needle guide (401). This point can be referred as the zero point. Maintaining the needle tip at the zero point can prevent the needle tip from contacting the vaginal wall (403) while the operator manipulates the ultrasound probe (405) for visualization and/or device placement. Furthermore, the handle could contain a limiting mechanism that limits the distal travel of the guiding/docking device to prevent the needle tip from exiting most ovaries during the initial needle puncture, e.g., a travel distance of about 3 cm (or e.g., about 1.5 to about 4 cm) from the zero point where the guiding/docking device can freely travel back and forth as long as the tip does not exceed the maximum travel distance. Once the operator inserts the docking/guiding device (409) into the ovary (407) (as shown in FIG. 36B), then the operator may release the limiting mechanism on the handle. Additionally or optionally, the handle may comprise a mechanism to allow the operator to adjust the maximum travel distance. This would allow the operator to insert the needle tip (411) more distally towards the capsule of the ovary (407) (as shown in FIG. 36C) and define a new maximum travel distance for the needle tip (411). This could prevent the operator from inadvertently advancing the needle tip beyond the ovary and could also prevent the needle tip from exiting the ovary in the event the ovary were to move due to patient respiration or other patient movement.

In other variations, the travel of the guiding/docking device may be controlled by increasing friction as it is advanced but can be retracted with less friction. Another variation could include a limiting mechanism such that the guiding/docking device and handle can only be advanced about 3 cm (or e.g., about 1.5 to about 4 cm) from the zero point. Then another mechanism in the handle, such as a wheel, lever, or slider, could be used to advance the guiding/docking device further into the ovary. This would prevent gross motions of the handle from advancing the needle tip beyond the ovary.

Figure 37:
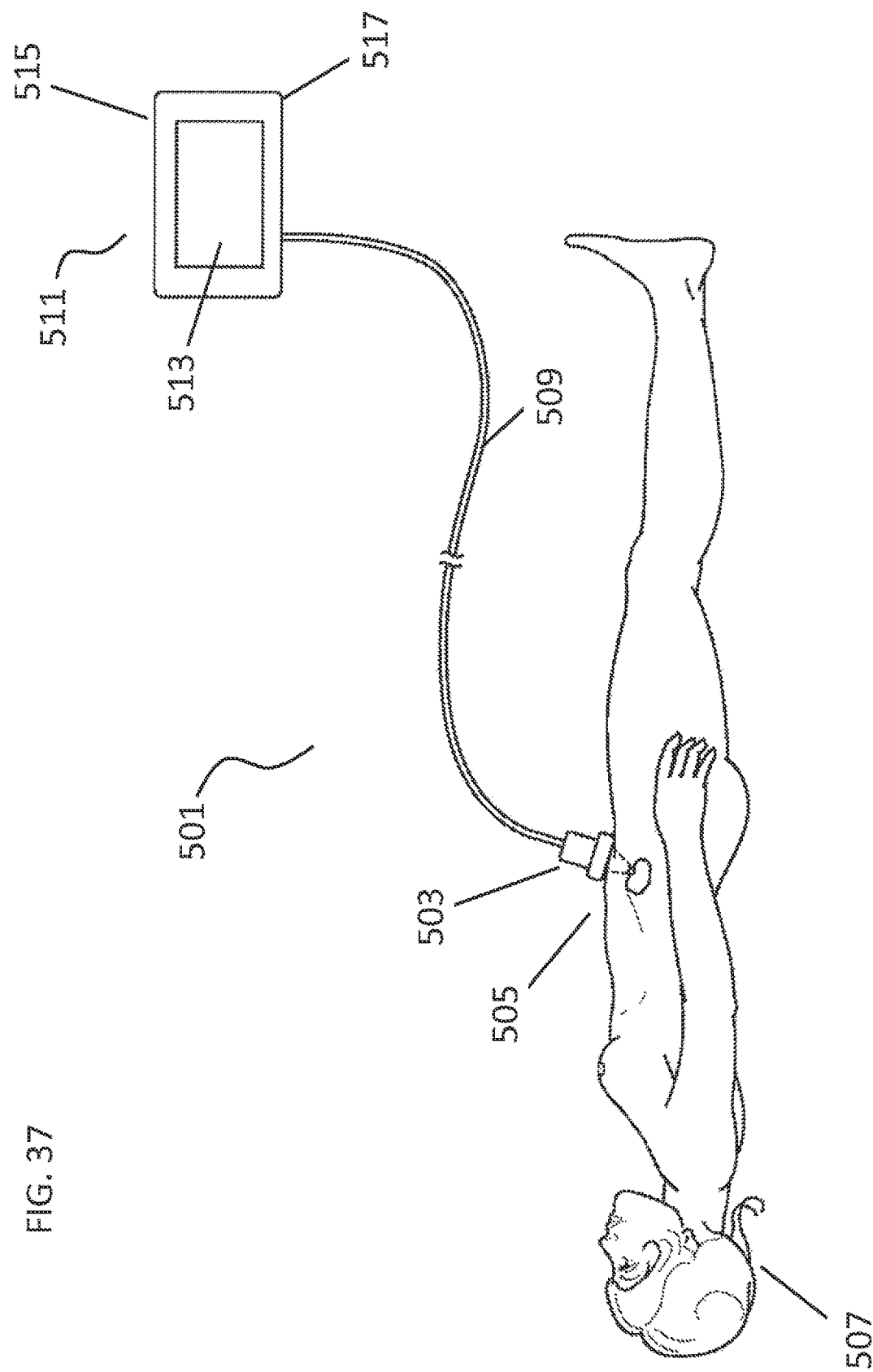
FIG. 37 depicts an embodiment of a non-invasive treatment system.

As previously stated, non-invasive treatment systems may be employed. FIG. 37 depicts an exemplary non-invasive treatment system. Referring to the figure, system (501) is comprised of an imaging and/or therapeutic element (503), configured for contact with the abdomen (505) of a patient (507); a connection (509) (e.g., cable) for connecting the imaging and/or therapeutic element (503); and a console (511), comprising a user interface (513), a feedback control system (515), one or more ultrasound sources (517) configured for imaging or application of energy to affect target tissue, and a mechanism for interpreting imaging data to enable targeting of desired target tissue.

Target tissues of an ovarian procedure may include the following: follicles, follicles of a particular size range (e.g., pre-antral follicles), stroma, thecal cells, stromal cells, granulosal cells, mesovarium, or nerves. In one instance, follicles, stroma, or thecal cells could be preferentially targeted and the vasculature could be relatively avoided. In another instance, the settings of the therapeutic element could be selected such that nerves are targeted and the vasculature could be relatively spared. In another instance, the cortex of the ovary could be targeted, and the stroma of the ovary could be relatively spared. In another instance, the stroma of the ovary could be targeted, and the ovarian cortex could be relatively spared. In another instance, the interface of the stroma and cortex could be preferentially targeted. In another instance, the mesovarium could be preferentially targeted. In another instance, the granulosal cells in antral and pre-antral cells may be preferentially targeted. In a further instance, the nerves in the pedicle of tissue connecting the ovary to surrounding tissues (i.e., mesovarium) could be targeted using treatment methods that spare the nearby vasculature (e.g., cryotherapy, selective heating/ablation, electroporation). Certain tissues (e.g., nerves) may be more susceptible to destruction at lower ablation thresholds, such that those tissues could be preferentially targeted. Some tissues may have particular acoustic or material properties (e.g., fluid-filled follicles) such that some forms of energy (e.g., ultrasound) could be used to specifically target those tissues. For example, in the case of HIFU, ultrasound imaging could be used to map the location of the follicles in the cortex of the ovary, and then energy could be directed to regions proximate to follicles clearly visible on ultrasound.

After or while delivering the therapeutic element, aspiration could be performed either through the guiding/docking device, through the therapeutic element, or through a device that contains both a docking and therapeutic element. The aspiration could be used to assist in reduction of cyst size, to assess if bleeding is controlled, to collect fluid for analysis, to remove any space created between tissues using fluid or gas, or for another purpose, The aspiration port could also be used to inject gas or other material, which might be used to change imaging characteristics of that region of the ovary; this could be used to label/mark portions of the ovary that had already been treated.

At the conclusion of the procedure, the docking element, the therapeutic element, or a combination thereof could be used to deliver materials, active agents, etc. to assist in the healing process and prevent the formation of adhesions. Some examples of these are the commercially available agents Interceed® Absorbable Adhesion Barrier (Ethicon, Somerville, NJ), Seprafilm® Adhesion Barrier (Genzyme, Bridgewater, NJ), and Adept® Adhesion Reduction Solution (Baxter, Deerfield, IL). These and other agents made of modified sugars, cellulose, fabrics, and colloids have been used in other surgical cases to minimize the frequency of surgical adhesions.

It is contemplated that in certain cases where the desired clinical effect was not achieved or where it was achieved but then subsequently the condition re-occurred, repeat procedures could be needed. In these cases, it might be necessary to target a different portion of the ovary, different cysts, or a different portion of the mesovarium. The inventors contemplate the need for using the system to specifically re-treat the same portion of tissue as the original treatment or a distinctly different potion of tissue from the first intervention.

III. Exemplary Combinations of Features

The following tables disclose various features of the methods and systems provided herein that can be combined to manipulate ovarian tissues and/or treat PCOS.

In Table 1, exemplary combinations of features for transvaginal, laparoscopic, percutaneous, or via a natural orifice route through the vagina-uterus-fallopian tubes approaches are provided.

dock on the ovary via any of the techniques in the 4th column, any of the tissue landmarks that could be used in aiding the procedure are listed in the 5th column, any of the therapeutic mechanisms that may employed by the device

TABLE 1

| Column 1 Access | Column 2 Visualization | Column 3 Tissue Separation | Column 4 Ovary docking | Column 5 Landmarks | Column 6 Therapeutic Mechanism | Column 7 Pattern of Therapeutic Delivery | Column 8 Aspiration/ Compression |
|---|---|---|---|---|---|---|---|
| Transvaginal | transvaginal ultrasound | fluid | suction/ aspiration/ vacuum | ovarian features cysts | Tissue Heat Ablation [FRY (monopolar, bipolar, multimodal), HIFU, Direct Heat, microwave, unfocused/partially focused ultrasound, laser, saline/water, steam] | Superior | aspiration at ovary interface |
| Laparoscopic | transabdominal ultrasound | air | concave surface | bony | Tissue Warning [RF (monopolar, bipolar, multimodal), HIFU, Direct Heat, microwave, unfocused/partially focused ultrasound, laser, saline/water, steam] | Near vasculature/ mesovarium | aspiration within ovary |
| Via a natural orifice route through the vagina-uterus-fallopian tubes | CT | mechanical scaffold | hook/needle | broad ligament/ ovary junction | non-thermal acoustic cavitation | away from vasculature/ mesovarium | aspiration to area surrounding ovary |
| Percutaneous | MR | mechanical balloon | abrasive surface | | Cryoablation (cooled element, liquid nitrogen, CO2, dry-ice) | Maximize interruption of cysts | ovary external compression |
| | endoscopic visualization | none | lasso | | Tissue Cooling (cooled element, saline/water) | preferential for cortical ovary | ovary internal compression |
| | OCT | | | | Mechanical disruption | preferential for medullary ovary | none |
| | virtual histology | | | | drug - Implant permanent or biodegradeable vs. no-implant, types of drugs: beta-blockers, anti-androgens, neurotoxins, or tissue toxins, 5-alpha-reductase inhibitors, or aromatase inhibitors | delivery to limit/ minimize disruption of ovarian capsule | |
| | ultrasound on guide or therapeutic element | | | | mechanical implant (permanent vs. biodegradeable), could be activated externally | delivery to maximize disruption of ovarian capsule | |

Notes:
specific embodiment may include none of features in a column or more than one feature in a column; oocyte harvesting may be done pre-procedure; either the guiding element or the treatment element or the combined guiding/treatment element may be steerable; optional anti-adhesive materials may be delivered to prevent adhesion formation, therapeutic element could be irrigated In Table 1 (transvaginal, laparoscopic, percutaneous, or via a natural orifice route through the vagina-uterus-fallopian tubes approaches), visualization of the procedure and/or tissues could be performed using any of the visualization techniques described in the 2nd column, tissue separation may be done via any of the techniques described in the 3rd column, the ovary could be engaged and the device could are described in the 6th column, possible patterns of therapy delivery are listed in column 7, and the various options for aspiration or ovarian compression that may be used in any of the embodiments are listed in column 8.

Table 2 provides exemplary combinations of features that could be used for open surgical approaches.

TABLE 2

| Column 1 Access | Column 2 Visualization | Column 3 Ovary docking | Column 4 Landmarks | Column 5 Therapeutic Mechanism | Column 6 Pattern of Therapeutic Delivery | Column 7 Aspiration/ Compression |
|---|---|---|---|---|---|---|
| surgical | transvaginal ultrasound | suction/ aspiration/ vacuum | ovarian features cysts | Tissue Heat Ablation [RF (monopolar, bipolar, multimodal), HIFU, Direct Heat, microwave, unfocused/partially focused ultrasound, laser, saline/water, steam] | Superior | aspiration at ovary interfere |
| | CT | concave surface | bony | Tissue Warning [RF (monopolar, bipolar, multimodal), HIFU, Direct Heat, microwave, unfocused/partially focused ultrasound, laser, saline/water, steam] | Near vasculature/ mesovarium | aspiration within ovary |
| | MR | hook/needle | broad ligament/ ovary junction | non-thermal acoustic cavitation | away from vasculature/ mesovarium | aspiration to area surrounding ovary |

TABLE 2-continued

| Column 1 Access | Column 2 Visualization | Column 3 Ovary docking | Column 4 Landmarks | Column 5 Therapeutic Mechanism | Column 6 Pattern of Therapeutic Delivery | Column 7 Aspiration/ Compression |
|---|---|---|---|---|---|---|
| | direct visualization endoscopic visualization OCT virtual histology ultrasound on guide or therapeutic element | abrasive surface lasso | | Cryoablation (cooled element, liquid nitrogen, $CO_2$, dry-ice) Tissue Cooling (cooled element, saline/water) Mechanical disruption<br><br>drug - implant permanent or biodegradeable vs. no-implant, types of drugs: beta-blockers, anti-androgens, neurotoxins or tissue toxins, 5-alpha-reductase inhibitors, or aromatase inhibitors mechanical implant (permanent vs. biodegradeable), could be activated externally | Maximize interruption of cysts preferential for cortical ovary preferential for medullary ovary delivery to limit/minimize disruption of ovarian capsule<br><br>delivery to maximize disruption of ovarian capsule | ovary external compression ovary internal compression none |

Notes:
specific embodiment may include none of features in a column or more than one feature in a column, oocyte harvesting may be done pre-procedure; either the guiding element or the treatment element or the combined guiding/treatment element may be steerable; optional anti-adhesive materials may be delivered to prevent adhesion formation, therapeutic element could be irrigated In Table 2 (surgical approaches), visualization of the procedure and/or tissues could be performed using any of the visualization techniques described in the 2nd column, the ovary could be engaged and the device could dock on the ovary via any of the techniques in the 3rd column, any of the tissue landmarks that could be used in aiding the procedure are listed in the 4th column, any of the therapeutic mechanisms that may employed by the device are described in the 5th column, possible patterns of therapy delivery are listed in column 6, and the various options for aspiration or ovarian compression which may be used in any of the embodiments are listed in column 7.

Other methods may include the non-invasive targeted delivery of energy to ovarian tissues. Table 3 provides exemplary combinations of elements that could be used to construct a system/device for such delivery of energy.

TABLE 3

| Column 1 Access | Column 2 Visualization | Column 3 Landmarks | Column 4 Therapeutic Element | Column 5 Pattern of Therapeutic Delivery | Column 6 Aspiration/ Compression |
|---|---|---|---|---|---|
| non-invasive (external) | transvaginal ultrasound | ovarian features cysts | Tissue Heat Ablation [RF (monopolar, bipolar, multimodal), HIFU, Direct Heat, microwave, unfocused/partially focused ultrasound, laser, saline/water, steam] | Superior | |
| | transabdominal ultrasound | bony | Tissue Warming [RF (monopolar, bipolar, multimodal), HIFU, Direct Heat, microwave, unfocused/partially focused ultrasound, laser, saline/water, steam] non-thermal acoustic cavitation | Near vasculature/ mesovarium | |
| | CT MR | broad ligament/ ovary junction | Cryoablation (cooled element, liquid nitrogen, $CO_2$, dry-ice) | away from vasculature/ mesovarium | ovary external compression |
| | | fiducial | Tissue Cooling (cooled element, saline/water) Mechanical disruption<br><br>drug - implant permanent or biodegradeable vs. no-implant, types of drugs: beta-blockers, anti-androgens, neurotoxins or tissue toxins, 5-alpha-reductase inhibitors, or aromatose inhibitors mechanical implant (permanent vs. biodegradeable), could be activated externally | Maximize interruption of cysts preferential for medullary ovary preferential for medullary ovary<br><br>delivery to limit/minimize disruption of ovarian capsule delivery to maximize disruption of ovarian capsule | |

Notes:
specific embodiment may include none of features in a column or more than one feature in a column In one variation, non-invasive imaging may also be employed to percutaneously or via a natural orifice route through the vagina-uterus-fallopian tubes place at least one fiducial within the patient, e.g., in the proximity of the target ovarian tissue, which may be used during the delivery of therapy to target treatment locations. Fiducials may be constructed of any material chosen for biocompatibility and compatibility with the desired imaging modality used during the therapeutic procedure. The fiducial may be placed either percutaneously or via a natural orifice route through the vagina-uterus-fallopian tubes via a needle, microcatheter, or other suitable delivery system through the abdominal wall, transvaginally, laparoscopically, or surgically.

In another variation, a device could be placed within the vagina. The device may be used with integrated imaging or use of a non-integrated imaging device (e.g., transvaginal ultrasound or abdominal ultrasound) to deliver either mechanical manipulation (e.g., sound, vibration, or other mechanical manipulation) or energy (e.g., electrical current) preferentially to the ovaries or portions of the ovaries. In the case of energy delivery, this could be either an ablative or non-ablative (e.g., energy similar to that used in transcutaneous electrical nerve stimulation) form of energy. This could be done repeatedly in a single session or temporally spaced as necessary.

IV. EXAMPLES

The following examples further illustrate embodiments of the systems and methods disclosed herein, and should not be construed in any way as limiting their scope.

Example 1: Ablation Volume with a Bipolar System Including a Straight Therapeutic Element and Using Max Power of 4 Watts An ovarian tissue apparatus having a bipolar electrode configuration was created using two Platinum-Iridium (90%/10%) bands mounted on a straight polymer shaft. The electrode outer diameters were 1.27 mm and the lengths were 3.0 mm. The electrodes were spaced 3.0 mm apart from each other and a temperature sensor was mounted on the inner diameter of each electrode. To evaluate lesion (ablated tissue) sizes, raw chicken breast was placed around the electrodes and a RF generator delivered energy to one electrode while the other electrode was used as part of the return path to the generator. RF energy was delivered for 30 seconds in order to achieve a target temperature of approximately 80° C. The maximum power observed was approximately 4 watts. A cross-section of the resulting lesion (cut lengthwise) showed apparent tissue necrosis measuring 3.8 mm wide and 10.4 mm long. Approximating the lesion volume as a cylinder (with diameter of 3.8 mm and length of 10.4 mm and volume=¼×π×D2×L), the lesion was calculated to have a volume of ablated tissue of 118 mm$^3$. While this experiment was conducted with a straight therapeutic element, similar results would be expected using a curved therapeutic element.

Example 2: Ablation Volume with a Bipolar System Including a Straight Therapeutic Element and Using Max Power of 10 Watts A similar experiment was conducted with the same electrode configuration described in Example 1. In this example, however, RF energy was delivered for a total of 15 seconds and targeted a maximum temperature of approximately 100° C. The maximum power utilized in this case was approximately 10 watts. A cross-section of the resulting lesion showed apparent tissue necrosis approximating an ellipse with a major axis, D1, of 4.5 mm and minor axis, D2, of 3.9 mm. Assuming a lesion length of 10 mm, the resulting lesion volume was calculated as 138 mm$^3$ (where volume=¼×π×D1×D2×L).

Example 3: Ablation Volume with a Bipolar System Including a Curved Therapeutic Element Experiments were conducted utilizing a similar bipolar electrode configuration as described in Example 1. However, the electrodes were mounted on a curved polymer shaft with an approximate radius of 7 mm. Both Platinum-Iridium (90%/10%) electrodes had outer diameters of 1.27 mm and lengths of 3.0 mm. The electrodes were spaced 3.0 mm apart from each other and a temperature sensor was mounted on the inner diameter of each electrode. In one experiment, RF energy was delivered for 30 seconds in order to achieve a target temperature of approximately 90° C. A cross-section of the resulting lesion (cut lengthwise) showed apparent tissue necrosis measuring 6.7 mm wide. In another experiment, RF energy was also delivered for 30 seconds in order to achieve a target temperature of approximately 90° C. A cross-section of the resulting lesion showed apparent tissue necrosis approximating an ellipse with a major axis, D1, of 6.0 mm and minor axis, D2, of 3.8 mm. Assuming a lesion length of 9 mm, the resulting lesion volume can be estimated as 161 mm$^3$ (where volume=¼×π×D1×D2×L).

V. Further Examples

Furthermore, the following examples, including any of the indicated combinations thereof, are disclosed herein and are comprised within the scope of the present disclosure.

1. A system for performing an ovarian procedure comprising:
   a) an ovarian tissue apparatus, the ovarian tissue apparatus comprising a docking device and a therapeutic element, the docking device comprising an elongate body and having a proximal end, a distal end, and defining a lumen therethrough, and the therapeutic element being slidable within and deployable from the lumen of the docking device;
   b) a transvaginal probe comprising a handle and an ultrasound transducer;
   c) a mechanical lock or a visual identifier on a part of the system; and
   d) a generator configured to supply energy to the therapeutic element,
wherein the mechanical lock or visual identifier is configured to maintain planar orientation of the therapeutic element relative to the ultrasound transducer and during a procedure on an ovary.

2. The system of example 1, wherein the therapeutic element comprises one or more curved structures, the curved structures comprising electrodes and having a straightened length and radius of curvature.

3. The system of example 1 or example 2, wherein the therapeutic element comprises two curved structures.

4. The system of example 2 or example 3, wherein the straightened length ranges between about 5.0 and about 40 mm.

5. The system of any of examples 2-4, wherein the radius of curvature ranges between about 3.0 and about 10 nun.

6. The system of example 1, wherein the therapeutic element comprises a curved electrode.

7. The system of any of the preceding examples, wherein the therapeutic element comprises an elongate body having a straightened length and a radius of curvature, an active electrode, and a return electrode.

8. The system of example 7, wherein the straightened length ranges between about 5.0 and about 40 mm.

9. The system of example 7 or example 8, wherein the radius of curvature ranges between about 3.0 and about 10 mm.

10. The system of any of examples 1-9, wherein the mechanical lock comprises an adjustable element having a locked position and an unlocked position.

11. The system of example 10, wherein the adjustable element comprises a notch configured to mate with the docking device when the alignment adapter is in the locked position.

12. The system of any of examples 1-11, wherein the generator is configured to supply radiofrequency energy at a power of 30 watts or less, and for a duration of 20 seconds or less.

13. The system of any of examples 1-12, wherein the generator is configured to supply continuous or pulsed radiofrequency energy.

14. The system of any of examples 1-13, wherein the distal end of the docking device comprises one or more attachment elements for releasably securing an ovary.

15. The system of example 14, wherein the one or more attachment elements comprise a hook, needle, or barb.

16. The system of any of examples 1-15, wherein the therapeutic element comprises an echogenic material.

17. The system of any of examples 1-15, wherein a portion of the therapeutic element comprises an echogenic material.

18. The system of any of examples 1-17, wherein a portion of the docking device comprises an echogenic material.

19. The system of any of example 1, wherein the therapeutic element comprises an electrode, a cryoablation element, a cooling element, a laser, or a combination thereof.

20. A method for treating polycystic ovary syndrome comprising:
 a) advancing a probe comprising a handle, an ultrasound transducer, and a needle guide into the vaginal canal;
 b) advancing an ovarian tissue apparatus into the needle guide, the ovarian tissue apparatus comprising a docking device and a therapeutic element;
 c) advancing the docking device through a vaginal wall;
 d) penetrating an ovary at a single entry point with the docking device or the therapeutic element;
 e) advancing the therapeutic element from the docking device into the ovary;
 f) delivering energy to affect a volume of tissue within the ovary using the therapeutic element to treat a symptom of polycystic ovary syndrome;
 g) retracting the therapeutic element into the docking device; and
 h) removing the ovarian tissue apparatus.

21. The method of example 20, further comprising repositioning the therapeutic element and repeating the step of energy delivery through the single entry point.

22. The method of example 20 or example 21, wherein the step of energy delivery comprises ablating a volume of tissue.

23. The method of any of examples 20-22, wherein advancement of the therapeutic element occurs in the same plane as the imaging plane.

24. The method of any of examples 20-23, wherein the affected volume of tissue ranges from about 240 mm$^3$ to about 3000 mm$^3$.

25. The method of any of examples 20-24, wherein the affected volume of tissue ranges from about 30 mm$^3$ to about 3000 mm$^3$.

26. The method of any of examples 20-23, wherein the affected volume of tissue ranges from about 3 to 20% of the ovary.

26. The method of any of examples 20-26, wherein the delivered energy is radiofrequency energy.

27. The method of example 26, wherein the radiofrequency energy is delivered for 15 to 45 seconds.

28. The method of example 26 or example 27, wherein the power of the radiofrequency energy is 30 watts or less.

29. The method of any of examples 26-28, wherein delivery of the radiofrequency energy is continuous or pulsed.

30. The method of any of examples 20-29, wherein the therapeutic element comprises one or more curved structures, the curved structures comprising electrodes and having a straightened length and radius of curvature.

31. The method of example 30, wherein the therapeutic element comprises two curved structures.

32. The method of example 30 or example 31, wherein the straightened length ranges between about 5.0 and about 40 mm.

33. The method of any of examples 30-32, wherein the radius of curvature ranges between about 3.0 and about 10 mm.

34. The method of example 20, wherein the therapeutic element comprises a curved electrode.

35. The method of example 20, wherein the therapeutic element comprises an elongate body having a straightened length and a radius of curvature, an active electrode, and a return electrode.

36. The method of example 35, wherein the straightened length ranges between about 5.0 and about 40 mm.

37. The method of example 35 or example 36, wherein the radius of curvature ranges between about 3.0 and about 10 mm.

38. The method of any of examples 20-37, wherein the symptom of polycystic ovary syndrome is infertility.

What is claimed:

1. A method for treating infertility associated with polycystic ovary syndrome in a patient in need thereof, the method comprising:
 advancing a docking device toward an ovary of the patient;
 penetrating an ovarian wall of the ovary via a distal tip of the docking device;
 advancing a therapeutic element from the docking device into the ovary; and
 delivering energy into tissue from inside the ovary using the therapeutic element positioned inside the ovary to ablate a volume of the tissue ranging from 30 mm$^3$ to 3000 mm$^3$ within the ovary to treat infertility associated with polycystic ovary syndrome (PCOS).

2. The method of claim 1, wherein penetrating the ovarian wall of the ovary comprises penetrating the ovarian wall at a single entry point.

3. The method of claim 1, wherein delivering energy comprises delivering radiofrequency energy.

4. The method of claim 1, wherein the tissue within the ovary comprises a polycystic ovary or ovarian cyst.

5. The method of claim 1, wherein delivering energy into the tissue within the ovary comprises delivering energy for 20 to 60 seconds.

6. The method of claim 1, wherein delivering energy into tissue reduces hormone levels to treat PCOS.

7. The method of claim 1, wherein the volume of the tissue ablated is from a single ablation.

8. The method of claim 1, wherein a total affected volume of the tissue ablated within the ovary is 240 mm$^3$ to 3000 mm$^3$.

9. The method of claim 1, wherein advancing the docking device comprises advancing the docking device into a vaginal canal, the method further comprising penetrating a vaginal wall via the distal tip of the docking device before penetrating the ovarian wall.

10. The method of claim 1, wherein delivering energy comprises delivering direct heating, cryoablation, cooling, laser, microwave, unfocused ultrasound, partially-focused ultrasound element, focused (HIFU) ultrasound, heated water/saline, steam, or chemical ablation energy.

11. The method of claim 1, further comprising imaging the ovary during an ablation procedure.

12. The method of claim 11, wherein imaging the ovary comprises imaging the ovary via an ultrasound transducer in a field of view of the ultrasound transducer.

13. The method of claim 1, further comprising, after delivering energy, reorienting the therapeutic element within the ovary, and then delivering additional energy within the ovary via the therapeutic element for one or more additional deliveries of energy within the ovary to ablate the tissue within the ovary.

14. The method of claim 1, further comprising removably coupling the docking device to a handle of a transvaginal ultrasound probe via an adapter configured to be removably coupled to the handle of the transvaginal ultrasound probe.

15. The method of claim 1, wherein the therapeutic element comprises an active electrode and a return electrode.

16. The method of claim 1, further comprising measuring temperature at the electrode during an ablation procedure.

17. The method of claim 1, further comprising measuring tissue temperature during an ablation procedure.

18. The method of claim 17, further comprising automatically terminating energy delivery if the measured tissue temperature exceeds a predetermined threshold.

19. The method of claim 1, further comprising measuring tissue impedance during an ablation procedure.

20. The method of claim 1, wherein the therapeutic element forms a curved configuration upon deployment from a lumen of the docking device within the ovary.

21. The method of claim 1, further comprising receiving user input comprising at least one of duration of energy emission, power, target temperature, or mode of operation.

* * * * *